US011828210B2

(12) United States Patent
Varughese et al.

(10) Patent No.: US 11,828,210 B2
(45) Date of Patent: Nov. 28, 2023

(54) DIAGNOSTIC SYSTEMS AND METHODS OF VEHICLES USING OLFACTION

(71) Applicant: DENSO International America, Inc., Southfield, MI (US)

(72) Inventors: Sibu Varughese, Sterling Heights, MI (US); Martín Nespolo, Grosse Pointe Woods, MI (US); Thomas Krzyzak, Livonia, MI (US); Gareth Webb, New Hudson, MI (US); Wilson Yim, Troy, MI (US); Matthew Johnson, Royal Oak, MI (US)

(73) Assignee: DENSO International America, Inc., Southfield, MI (US)

( * ) Notice: Subject to any disclaimer, the term of this patent is extended or adjusted under 35 U.S.C. 154(b) by 329 days.

(21) Appl. No.: 17/218,513

(22) Filed: Mar. 31, 2021

(65) Prior Publication Data

US 2022/0056824 A1 Feb. 24, 2022

Related U.S. Application Data

(60) Provisional application No. 63/067,922, filed on Aug. 20, 2020.

(51) Int. Cl.

*F01M 11/10* (2006.01)
*F01P 11/14* (2006.01)
*G01N 33/00* (2006.01)
*B60T 17/22* (2006.01)

(Continued)

(52) U.S. Cl.

CPC ............. *F01M 11/10* (2013.01); *B60T 17/22* (2013.01); *F01N 11/00* (2013.01); *F01P 11/14* (2013.01); *G01N 33/0047* (2013.01); *F01M 2011/14* (2013.01); *F01P 2031/18* (2013.01); *G01N 21/94* (2013.01); *Y02A 50/20* (2018.01)

(58) Field of Classification Search

None

See application file for complete search history.

(56) References Cited

U.S. PATENT DOCUMENTS 6,044,826 A 4/2000 Bayerle et al.
6,053,738 A 4/2000 Ivey, Jr.
6,072,398 A 6/2000 Hayes et al.

(Continued)

FOREIGN PATENT DOCUMENTS

CA 2341894 A1 3/2000
CA 2363251 A1 8/2000

(Continued)

*Primary Examiner* — Kevin R Steckbauer

(74) *Attorney, Agent, or Firm* — Harness, Dickey & Pierce, P.L.C.

(57) ABSTRACT

A vehicle system includes: at least one of: (a) a particulate matter sensor configured to measure an amount of particulate within a passenger cabin of a vehicle; and (b) a volatile organic compounds (VOC) sensor configured to measure an amount of VOCs within the passenger cabin of the vehicle; and a control module configured to, based on at least one of the amount of particulate and the amount of VOCs within the passenger cabin of the vehicle, diagnose at least one of: a characteristic of the vehicle; presence of a chemical in the passenger cabin of the vehicle; occurrence of an event within the passenger cabin of the vehicle; and a remaining life of engine oil of the vehicle.

13 Claims, 12 Drawing Sheets

| Measurement combination | Diagnosis |
|---|---|
| Smell (VOC) profile matches nitric oxide (PM may be irrelevant) | catalytic converter issue |
| Measured smell (VOC) matches profile of heated/vaporized ethyl glycol (PM may be irrelevant) | Engine coolant leak |
| Smell (VOC) profile matches profile of heated/vaporized engine oil. PM sensor sees increase in concentration of particles <1μm. | Engine oil leak |
| Measured smell (VOC) matches profile of overheated/melting EPDM/poly/etc. (PM may be irrelevant) | belt or hose rubbing |
| Measured smell (VOC) matches profile of overheated clutch (PM may be irrelevant) | Overheating clutch |
| Measured smell (VOC) matches profile of overheated brake pads/brake fluid/etc. (PM may be irrelevant) | Brake issue |
| Measured smell (VOC) matches profile of overheated overloaded vehicle, battery failure/fault. (PM may be irrelevant) | Overloaded vehicle, battery failure/fault |

(51) Int. Cl.
*F01N 11/00* (2006.01)
*G01N 21/94* (2006.01)

(56) References Cited

U.S. PATENT DOCUMENTS 6,081,195 A 6/2000 Lynch
6,082,415 A 7/2000 Rowland et al.
6,089,016 A 7/2000 Takaku
6,097,288 A 8/2000 Koeppe, Jr.
6,118,386 A 9/2000 Yousif
6,138,655 A 10/2000 Kerns et al.
6,144,310 A 11/2000 Morris
6,145,305 A 11/2000 Itou et al.
6,160,487 A 12/2000 DeLuca
6,166,647 A 12/2000 Wong
6,167,695 B1 1/2001 Itou et al.
6,181,250 B1 1/2001 Brooks, Jr.
6,182,497 B1 2/2001 Krajci
6,196,527 B1 3/2001 Huang
6,208,256 B1 3/2001 Fleming et al.
6,215,407 B1 4/2001 Winther
6,216,448 B1 4/2001 Schnaibel et al.
6,216,450 B1 4/2001 Takahashi et al.
6,220,229 B1 4/2001 Kawamura et al.
6,226,982 B1 5/2001 Poggio et al.
6,233,923 B1 5/2001 Itou et al.
6,237,397 B1 5/2001 Shinar et al.
6,240,908 B1 6/2001 Hyodo et al.
6,245,205 B1 6/2001 Schnaibel et al.
6,266,955 B1 7/2001 Liang et al.
6,272,938 B1 8/2001 Baghel et al.
6,281,797 B1 8/2001 Forster et al.
6,282,940 B1 9/2001 Hung et al.
6,287,519 B1 9/2001 Nordman et al.
6,288,643 B1 9/2001 Lerg et al.
6,290,829 B1 9/2001 Kato et al.
6,293,093 B1 9/2001 Goralski et al.
6,293,120 B1 9/2001 Hashimoto
6,294,075 B1 9/2001 Poggio et al.
6,301,881 B1 10/2001 Kumar
6,314,790 B1 11/2001 Sagisaka et al.
6,317,041 B1 11/2001 Singer et al.
6,320,388 B1 11/2001 Sun et al.
6,330,795 B1 12/2001 Takaku et al.
6,338,326 B1 1/2002 Ebeling et al.
6,338,977 B1 1/2002 Kunugi et al.
6,339,379 B1 1/2002 Argus et al.
6,340,447 B2 1/2002 Johnson
6,348,871 B1 2/2002 Tanguay et al.
6,353,386 B1 3/2002 Castonguay et al.
6,357,223 B1 3/2002 Caren et al.
6,357,224 B1 3/2002 Kawamoto et al.
6,357,726 B1 3/2002 Watkins
6,359,567 B1 3/2002 Park
6,363,713 B1 4/2002 Wu et al.
6,363,771 B1 4/2002 Liang et al.
6,374,662 B1 4/2002 Oda et al.
6,376,254 B1 4/2002 Bather et al.
6,378,298 B2 4/2002 Harima et al.
6,378,359 B1 4/2002 Dobson et al.
6,382,017 B1 5/2002 Majkowski et al.
6,386,246 B2 5/2002 Pope et al.
6,386,969 B1 5/2002 O'Brien
6,408,616 B1 6/2002 Mazur et al.
6,410,249 B1 6/2002 Ngai et al.
6,411,207 B2 6/2002 Shaffer
6,411,905 B1 6/2002 Guoliang et al.
6,416,479 B1 7/2002 Seidman
6,418,780 B1 7/2002 Chon
6,418,983 B1 7/2002 Payne et al.
6,420,973 B2 7/2002 Acevedo
6,422,226 B2 7/2002 Niki et al.
6,425,242 B2 7/2002 Booth et al.
6,425,384 B1 7/2002 Howarth et al.
6,429,019 B1 8/2002 Goldstein et al.
6,432,692 B1 8/2002 Bradfield et al.
6,433,696 B1 8/2002 Deiterman et al.
6,435,164 B1 8/2002 Kaiser et al.
6,436,712 B1 8/2002 Yurgil et al.
6,439,026 B2 8/2002 Nakano et al.
6,443,908 B2 9/2002 Stone
6,447,731 B1 9/2002 Sun et al.
6,448,888 B1 9/2002 Horner et al.
6,451,210 B1 9/2002 Sivavec et al.
6,452,510 B1 9/2002 Zysko
6,463,735 B2 10/2002 Morinaga et al.
6,463,967 B1 10/2002 Boyle
6,464,144 B1 10/2002 Swartz et al.
6,467,254 B1 10/2002 Cullen et al.
6,467,332 B1 10/2002 Bertschi et al.
6,471,193 B2 10/2002 Cole Warren
6,474,138 B1 11/2002 Chang et al.
6,484,559 B2 11/2002 Dodabalapur et al.
6,484,951 B1 11/2002 Mueller
6,485,688 B1 11/2002 Sivavec et al.
6,491,828 B1 12/2002 Sivavec et al.
6,492,907 B1 12/2002 McCracken
6,493,638 B1 12/2002 McLean et al.
6,494,077 B2 12/2002 Aoyama et al.
6,495,375 B2 12/2002 Ledig
6,497,092 B1 12/2002 Theis
6,497,227 B2 12/2002 Wang et al.
6,499,291 B2 12/2002 Lang et al.
6,499,516 B2 12/2002 Pope et al.
6,502,386 B1 1/2003 Mazur et al.
6,508,111 B2 1/2003 Osaki et al.
6,515,749 B2 2/2003 Pipino
6,518,878 B1 2/2003 Skoff
6,522,248 B1 2/2003 Andres et al.
6,525,662 B1 2/2003 Ford
6,528,191 B1 3/2003 Senner
6,529,808 B1 3/2003 Diem
6,532,734 B1 3/2003 Nader et al.
6,534,319 B1 3/2003 Liu
6,539,705 B2 4/2003 Beer et al.
6,539,707 B2 4/2003 Ikemoto et al.
6,541,052 B1 4/2003 Rohleder
6,544,971 B1 4/2003 Berliner et al.
6,545,608 B1 4/2003 Kaufman
6,550,310 B1 4/2003 Liu et al.
6,550,318 B2 4/2003 Isobe et al.
6,552,647 B1 4/2003 Thiessen et al.
6,562,208 B2 5/2003 Slater et al.
6,563,318 B2 5/2003 Kawakami et al.
6,564,154 B1 5/2003 Zimmerman et al.
6,564,543 B1 5/2003 Orzel et al.
6,571,550 B2 6/2003 Rosel et al.
6,575,013 B2 6/2003 Bao et al.
6,576,911 B1 6/2003 Potyrailo et al.
6,578,406 B2 6/2003 Kunugi et al.
6,578,715 B2 6/2003 Scranton, Jr. et al.
6,583,720 B1 6/2003 Quigley
6,588,251 B2 7/2003 Zhang et al.
6,589,476 B1 7/2003 Fencl
6,590,710 B2 7/2003 Hara et al.
6,594,562 B2 7/2003 Kaiser et al.
6,595,037 B2 7/2003 McGinley
6,596,236 B2 7/2003 DiMeo, Jr. et al.
6,598,468 B2 7/2003 Zur Loye et al.
6,598,470 B2 7/2003 Ludwig et al.
6,600,417 B2 7/2003 Lerg et al.
6,600,424 B1 7/2003 Morris
6,604,007 B2 8/2003 Leven et al.
6,604,405 B2 8/2003 Whynall et al.
6,606,566 B1 8/2003 Sunshine
6,607,700 B1 8/2003 Apte et al.
6,609,416 B2 8/2003 Brock
6,611,204 B2 8/2003 Schmurr
6,617,166 B2 9/2003 White Gray
6,619,107 B1 9/2003 Tsukamoto et al.
6,623,619 B2 9/2003 Saffell et al.
6,623,973 B2 9/2003 Levitsky et al.
6,631,333 B1 10/2003 Lewis et al.
6,631,611 B2 10/2003 Shi et al.

(56) References Cited

U.S. PATENT DOCUMENTS 6,632,268 B2 10/2003 Seeley
6,637,191 B1 10/2003 Ziemba et al.
6,640,608 B2 11/2003 Pepper et al.
6,640,620 B2 11/2003 Cook et al.
6,645,772 B1 11/2003 Kirby et al.
6,646,444 B2 11/2003 Dolgov et al.
6,651,422 B1 11/2003 LeGare
6,658,841 B2 12/2003 Beer et al.
6,659,095 B2 12/2003 Kotwicki et al.
6,661,299 B2 12/2003 Dodabalapur et al.
6,666,068 B2 12/2003 Boyd et al.
6,666,201 B1 12/2003 Mazur
6,668,616 B1 12/2003 Shoji et al.
6,672,164 B1 1/2004 Haanstra et al.
6,679,238 B2 1/2004 Nebiyeloul-Kifle et al.
6,682,638 B1 1/2004 Prohaska et al.
6,684,628 B2 2/2004 Gobel et al.
6,684,852 B2 2/2004 Wright et al.
6,685,955 B2 2/2004 Johnson
6,687,601 B2 2/2004 Bale et al.
6,689,322 B2 2/2004 Mills et al.
6,691,023 B2 2/2004 Fujino et al.
6,691,554 B2 2/2004 Eastman et al.
6,693,535 B2 2/2004 Van Bosch et al.
6,694,726 B2 2/2004 Sakai
6,696,296 B2 2/2004 Li et al.
6,698,187 B2 3/2004 Nishioka et al.
6,701,245 B2 3/2004 Birkner et al.
6,701,706 B2 3/2004 Bruck et al.
6,701,707 B1 3/2004 Upadhyay et al.
6,711,470 B1 3/2004 Hartenstein et al.
6,711,932 B2 3/2004 Iwazaki et al.
6,712,101 B1 3/2004 Nanaji
6,712,287 B1 3/2004 Le Pesant et al.
6,712,770 B2 3/2004 Lin et al.
6,713,020 B2 3/2004 Kato et al.
6,716,406 B2 4/2004 Reisfeld et al.
6,732,031 B1 5/2004 Lowrey et al.
6,736,120 B2 5/2004 Surnilla
6,736,121 B2 5/2004 Gopichandra
6,739,122 B2 5/2004 Kitajima et al.
6,739,176 B2 5/2004 Neuhausen et al.
6,739,177 B2 5/2004 Sato et al.
6,739,310 B2 5/2004 Esteghlal et al.
6,740,433 B2 5/2004 Senner
6,741,174 B2 5/2004 Rhoades et al.
6,741,181 B2 5/2004 Skaggs
6,744,373 B2 6/2004 Koyano et al.
6,744,503 B2 6/2004 Vo-Dinh et al.
6,745,747 B2 6/2004 Surnilla
6,753,786 B1 6/2004 Apperson et al.
6,754,366 B2 6/2004 Sansone
6,758,185 B2 7/2004 Surnilla et al.
6,761,023 B1 7/2004 Schnaibel et al.
6,763,708 B2 7/2004 Ting et al.
6,765,490 B2 7/2004 Lopez et al.
6,768,420 B2 7/2004 McCarthy et al.
6,770,873 B2 8/2004 Pusterla et al.
6,771,181 B1 8/2004 Hughen, Jr.
6,772,585 B2 8/2004 Iihoshi et al.
6,774,802 B2 8/2004 Bachinski et al.
6,775,602 B2 8/2004 Gordon, Jr. et al.
6,778,082 B2 8/2004 Goodwin
6,778,086 B2 8/2004 Morrone et al.
6,781,696 B1 8/2004 Rosenberger et al.
6,784,798 B2 8/2004 Morris
6,785,605 B2 8/2004 Huller et al.
6,788,197 B1 9/2004 Thuillard et al.
6,791,453 B1 9/2004 Andres et al.
6,792,339 B2 9/2004 Basson et al.
6,792,346 B2 9/2004 Takebayashi et al.
6,792,767 B1 9/2004 Pargeter et al.
6,793,881 B2 9/2004 Himes
6,801,132 B2 10/2004 Clauss et al.
6,803,236 B2 10/2004 Bailey et al.
6,804,951 B2 10/2004 Nader et al.
6,807,806 B2 10/2004 Takaku et al.
6,810,659 B1 11/2004 Bidner et al.
6,816,069 B2 11/2004 Quigley
6,817,225 B2 11/2004 Boyd et al.
6,819,257 B2 11/2004 Swieboda et al.
6,820,012 B2 11/2004 Sunshine
6,822,096 B2 11/2004 Kato
6,822,215 B2 11/2004 Hensel
6,822,555 B2 11/2004 Mansfield, Jr. et al.
6,824,513 B2 11/2004 Jansen
6,827,903 B2 12/2004 Guerra
6,828,156 B2 12/2004 Ohsuga et al.
6,830,027 B1 12/2004 Segawa et al.
6,830,043 B2 12/2004 Morinaga et al.
6,831,471 B2 12/2004 Gertiser et al.
6,834,497 B2 12/2004 Miyoshi et al.
6,834,530 B2 12/2004 Kita et al.
6,836,210 B2 12/2004 Tanguay
6,836,722 B2 12/2004 Yook
6,837,987 B1 1/2005 King
6,838,067 B2 1/2005 Salisbury et al.
6,843,240 B1 1/2005 Hahn et al.
6,843,835 B2 1/2005 Fornai et al.
6,848,418 B1 2/2005 Summers et al.
6,848,439 B2 2/2005 Ohkuma
6,850,172 B2 2/2005 Becka
6,860,100 B1 3/2005 Bidner et al.
6,862,535 B2 3/2005 Binder
6,873,254 B2 3/2005 Andres et al.
6,873,764 B2 3/2005 Maisenholder et al.
6,874,490 B2 4/2005 Surnilla
6,877,498 B1 4/2005 Matsushima et al.
6,879,894 B1 4/2005 Lightner et al.
6,879,936 B2 4/2005 Dilger
6,880,380 B2 4/2005 Nagashima et al.
6,881,382 B2 4/2005 Goldstein et al.
6,882,927 B2 4/2005 Suzuki
6,882,928 B2 4/2005 Yurgil
6,885,279 B2 4/2005 Tseung et al.
6,887,069 B1 5/2005 Thornton et al.
6,891,470 B2 5/2005 Bohinc, Jr.
6,893,632 B2 5/2005 Johnson
6,896,781 B1 5/2005 Shen et al.
6,898,927 B2 5/2005 Morinaga et al.
6,901,741 B2 6/2005 Kobayashi et al.
6,902,701 B1 6/2005 Hughes et al.
6,912,840 B2 7/2005 Posselt et al.
6,912,924 B2 7/2005 Loomis et al.
6,915,203 B2 7/2005 Maegawa et al.
6,920,282 B2 7/2005 He et al.
6,921,604 B2 7/2005 Kato et al.
6,922,149 B1 7/2005 Ford
6,922,639 B2 7/2005 Kawase et al.
6,925,796 B2 8/2005 Nieuwstadt et al.
6,926,601 B2 8/2005 Aoki et al.
6,928,348 B1 8/2005 Lightner et al.
6,930,586 B2 8/2005 Tseung et al.
6,933,151 B2 8/2005 Bailey et al.
6,933,491 B2 8/2005 Maida, Jr.
6,936,147 B2 8/2005 Prohaska et al.
6,938,832 B2 9/2005 Sada
6,940,410 B2 9/2005 Deacy
6,940,411 B2 9/2005 Smith et al.
6,941,193 B2 9/2005 Frecska et al.
6,947,132 B1 9/2005 Boss et al.
6,947,817 B2 9/2005 Diem
6,948,352 B2 9/2005 Rabbett et al.
6,952,945 B2 10/2005 O'Brien
6,957,562 B2 10/2005 Anilovich et al.
6,958,689 B2 10/2005 Anderson et al.
6,961,653 B2 11/2005 Maki
6,962,082 B2 11/2005 Hashimoto et al.
6,964,742 B2 11/2005 Myers
6,965,314 B2 11/2005 Bohinc, Jr.
6,965,344 B1 11/2005 Halsey et al.
6,968,677 B2 11/2005 Tamura
6,968,833 B2 11/2005 Yu et al.
6,975,944 B1 12/2005 Zenhausern

(56) References Cited

U.S. PATENT DOCUMENTS 6,976,382 B2 12/2005 Kadowaki et al.
6,978,212 B1 12/2005 Sunshine
6,979,260 B2 12/2005 Liu
6,979,363 B2 12/2005 Boyd et al.
6,981,368 B2 1/2006 van Nieuwstadt et al.
6,985,082 B1 1/2006 Dutta et al.
6,986,294 B2 1/2006 Fromme et al.
6,989,757 B2 1/2006 Geoffrey J. et al.
6,990,799 B2 1/2006 Bidner et al.
6,995,664 B1 2/2006 Darling
6,998,991 B1 2/2006 Goldstein et al.
7,002,481 B1 2/2006 Crane et al.
7,003,943 B2 2/2006 Ketterer et al.
7,005,994 B2 2/2006 King
7,007,458 B2 3/2006 Mazur et al.
7,007,542 B2 3/2006 Wang et al.
7,008,913 B2 3/2006 Hei et al.
7,012,544 B2 3/2006 Cunningham et al.
7,013,214 B2 3/2006 Ohsaki
7,015,943 B2 3/2006 Chiang
7,019,626 B1 3/2006 Funk
7,019,655 B2 3/2006 Lopez et al.
7,021,300 B2 4/2006 Maki et al.
7,024,869 B2 4/2006 Puri et al.
7,026,945 B2 4/2006 Hill
7,028,534 B2 4/2006 Watanabe et al.
7,030,748 B2 4/2006 Tanguay
7,040,307 B2 5/2006 Nagashima et al.
7,048,199 B2 5/2006 Melink
7,051,573 B2 5/2006 Bresciani et al.
7,051,689 B2 5/2006 Tamura et al.
7,053,822 B2 5/2006 Rickerson, Jr.
7,056,474 B2 6/2006 Dumas et al.
7,057,517 B1 6/2006 Convery
7,059,112 B2 6/2006 Bidner et al.
7,064,664 B2 6/2006 Lerg et al.
7,064,670 B2 6/2006 Galperin et al.
7,067,319 B2 6/2006 Wills et al.
7,069,142 B2 6/2006 Keller et al.
7,073,465 B2 7/2006 Woll et al.
7,076,371 B2 7/2006 Fu
7,077,741 B2 7/2006 Brenner et al.
7,080,544 B2 7/2006 Stepanik et al.
7,082,752 B2 8/2006 Plote et al.
7,083,110 B2 8/2006 Kim et al.
7,084,963 B2 8/2006 Leipertz
7,096,715 B2 8/2006 Kita et al.
7,100,420 B2 9/2006 Read et al.
7,100,586 B2 9/2006 Matsumoto
7,102,504 B2 9/2006 Kates
7,102,505 B2 9/2006 Kates
7,105,037 B2 9/2006 Olander et al.
7,107,758 B2 9/2006 Hirooka
7,108,774 B1 9/2006 Laitinen-Vellonen
7,109,874 B2 9/2006 Pilkington
7,109,879 B2 9/2006 Stults et al.
7,111,451 B2 9/2006 Dou et al.
7,112,443 B2 9/2006 Hajduk et al.
7,114,329 B2 10/2006 Rosel et al.
7,116,750 B1 10/2006 Iaquinta et al.
7,117,664 B2 10/2006 Takaku et al.
7,124,018 B2 10/2006 Hassdenteufel et al.
7,127,935 B2 10/2006 Bonne et al.
7,131,261 B2 11/2006 Wackerow et al.
7,131,262 B2 11/2006 Sealy et al.
7,131,322 B2 11/2006 Booms et al.
7,131,344 B2 11/2006 Tarumi
7,134,273 B2 11/2006 Mazur et al.
7,139,072 B1 11/2006 Boss et al.
7,140,230 B2 11/2006 Kita et al.
7,142,105 B2 11/2006 Chen
7,142,107 B2 11/2006 Kates
7,146,851 B2 12/2006 Wakahara et al.
7,151,787 B2 12/2006 Kulp et al.
7,154,579 B2 12/2006 Selander et al.
7,156,968 B2 1/2007 Tsapakh et al.
7,158,040 B2 1/2007 Morris
7,159,384 B2 1/2007 Otake et al.
7,160,732 B2 1/2007 Lippard et al.
7,161,678 B2 1/2007 Schultz
7,162,860 B2 1/2007 Shirakawa et al.
7,162,862 B2 1/2007 Nagai et al.
7,167,815 B2 1/2007 Labreche et al.
7,170,418 B2 1/2007 Rose-Pehrsson et al.
7,178,381 B2 2/2007 Tajima et al.
7,179,355 B2 2/2007 Harper
7,179,422 B2 2/2007 Kirby et al.
7,182,845 B2 2/2007 Kaiser
7,183,933 B2 2/2007 Dzurko et al.
7,189,373 B2 3/2007 Taniguchi et al.
7,190,171 B2 3/2007 Kawakami et al.
7,190,265 B1 3/2007 Bohinc, Jr.
7,190,276 B2 3/2007 Lopez et al.
7,192,459 B2 3/2007 Puri et al.
7,194,890 B2 3/2007 Tanaka et al.
7,199,724 B2 4/2007 Danvir et al.
7,200,348 B2 4/2007 Brenner
7,201,787 B2 4/2007 Choi et al.
7,202,795 B2 4/2007 Karamanian et al.
7,204,237 B2 4/2007 Booms et al.
7,210,289 B2 5/2007 Sugano et al.
7,212,734 B2 5/2007 Pepper et al.
7,216,478 B2 5/2007 Brown et al.
7,216,527 B2 5/2007 Imoto
7,217,354 B2 5/2007 Mahurin et al.
7,219,009 B1 5/2007 Sager et al.
7,221,171 B2 5/2007 Sohl, III et al.
7,222,615 B2 5/2007 Buck et al.
7,227,136 B2 6/2007 Walte et al.
7,229,831 B2 6/2007 Puri
7,229,833 B1 6/2007 Andersson
7,230,528 B2 6/2007 Kates
7,236,095 B2 6/2007 Smith et al.
7,237,504 B2 7/2007 Davis et al.
7,240,479 B1 7/2007 Fujimoto
7,240,668 B1 7/2007 DeMinco
7,241,881 B2 7/2007 Vosshall et al.
7,242,310 B2 7/2007 Hotton et al.
7,243,527 B2 7/2007 Kim
7,244,345 B1 7/2007 Filanovsky
7,246,604 B2 7/2007 Cullen
7,248,156 B2 7/2007 Wisniewski et al.
H2197 H 8/2007 Gord
7,254,474 B2 8/2007 Lihoshi et al.
7,257,481 B2 8/2007 Shimura et al.
7,257,941 B1 8/2007 Reuter
7,259,670 B2 8/2007 Cunningham et al.
7,262,060 B2 8/2007 Hirowatari et al.
7,264,778 B2 9/2007 McDaniel et al.
7,265,662 B2 9/2007 Belanger
7,268,683 B2 9/2007 Andres et al.
7,269,996 B2 9/2007 Schnaibel et al.
7,270,600 B2 9/2007 Kim et al.
7,278,304 B2 10/2007 Zanini-Fisher et al.
7,278,414 B2 10/2007 Diem
7,279,080 B2 10/2007 Chapples et al.
7,280,214 B2 10/2007 DiFoggio et al.
7,281,369 B2 10/2007 Emi et al.
7,281,439 B2 10/2007 Schmitt et al.
7,289,786 B2 10/2007 Krasner
7,296,459 B2 11/2007 Son et al.
7,298,252 B1 11/2007 Sutardja et al.
7,299,625 B2 11/2007 Uchida et al.
7,302,959 B2 12/2007 Gonia
7,310,047 B2 12/2007 Al-Wehebi
7,314,165 B2 1/2008 Bonalle et al.
7,314,723 B2 1/2008 Zwiebel
7,317,927 B2 1/2008 Staton et al.
7,319,402 B1 1/2008 Sudderth
7,319,403 B2 1/2008 Woodard et al.
7,325,393 B2 2/2008 Miura
7,325,748 B2 2/2008 Acker, Jr.
7,333,129 B2 2/2008 Miller et al.
7,334,401 B2 2/2008 Cheng

(56) References Cited

U.S. PATENT DOCUMENTS 7,336,168 B2 2/2008 Kates
7,342,504 B2 3/2008 Crane et al.
7,343,734 B2 3/2008 Aliakbarzadeh et al.
H2215 H 4/2008 Allen et al.
7,351,591 B2 4/2008 Koo et al.
7,357,015 B2 4/2008 Taguchi et al.
7,365,539 B2 4/2008 Szyperski et al.
7,372,370 B2 5/2008 Stults et al.
7,374,878 B2 5/2008 Stryer et al.
7,378,954 B2 5/2008 Wendt
7,384,524 B2 6/2008 Kirby et al.
7,387,011 B2 6/2008 Fujiki et al.
7,388,383 B2 6/2008 Kawakami et al.
7,389,158 B2 6/2008 Desrochers et al.
7,390,664 B2 6/2008 Fung et al.
7,390,670 B2 6/2008 Akhavan-Tafti et al.
7,391,316 B2 6/2008 Albert et al.
7,401,503 B2 7/2008 Binnig
7,403,128 B2 7/2008 Scuka et al.
7,403,850 B1 7/2008 Boutin et al.
7,404,397 B2 7/2008 Dobeck
7,404,882 B2 7/2008 Prohaska et al.
7,406,871 B2 8/2008 Sugiura
7,407,650 B2 8/2008 Heltovics et al.
7,408,473 B2 8/2008 Adkins et al.
7,410,616 B2 8/2008 Santini, Jr. et al.
7,411,494 B2 8/2008 Kates
7,411,671 B2 8/2008 De Vandiere et al.
7,413,731 B2 8/2008 Heltovics et al.
7,414,726 B1 8/2008 Bambeck
7,415,343 B2 8/2008 Zushi et al.
7,415,901 B2 8/2008 Desrochers et al.
7,417,540 B2 8/2008 Johnston et al.
7,420,473 B2 9/2008 Eicken et al.
7,420,662 B2 9/2008 Yalin et al.
7,421,836 B2 9/2008 Pallett et al.
7,421,911 B2 9/2008 Desrochers et al.
7,422,646 B2 9/2008 Prohaska et al.
7,423,543 B2 9/2008 Cartwright et al.
7,425,307 B2 9/2008 Sohl, III et al.
7,425,445 B2 9/2008 Matsunami et al.
7,432,113 B2 10/2008 Koo et al.
7,433,777 B2 10/2008 Ikari et al.
7,433,778 B2 10/2008 Mehnert
7,434,744 B2 10/2008 Garozzo et al.
7,442,343 B2 10/2008 Salisbury et al.
7,444,235 B2 10/2008 Anilovich et al.
7,449,990 B2 11/2008 Andres et al.
7,454,895 B2 11/2008 Hoard et al.
7,455,444 B2 11/2008 Chien
7,461,536 B2 12/2008 Schnaibel et al.
7,462,218 B2 12/2008 Ducrocq
7,464,580 B2 12/2008 Zeng et al.
7,477,983 B2 1/2009 Shimura et al.
7,479,893 B2 1/2009 Weston et al.
7,480,044 B2 1/2009 Leipertz
7,483,781 B2 1/2009 Wakahara et al.
7,485,169 B2 2/2009 Olander et al.
7,487,035 B2 2/2009 Nozawa et al.
7,487,662 B2 2/2009 Schabron et al.
7,492,255 B1 2/2009 Morris
7,499,792 B2 3/2009 Rosel et al.
7,502,115 B2 3/2009 Patel et al.
7,503,899 B2 3/2009 Caillouette
7,504,235 B2 3/2009 Song
7,508,314 B2 3/2009 Andres et al.
7,510,470 B2 3/2009 Arts
7,515,058 B2 4/2009 Normand
7,519,467 B2 4/2009 Katoh
7,521,018 B2 4/2009 Niemann et al.
7,522,039 B2 4/2009 Sutardja et al.
7,523,653 B2 4/2009 Smith et al.
7,525,445 B2 4/2009 DeLuca et al.
7,526,950 B2 5/2009 Van Nieuwstadt et al.
7,528,732 B2 5/2009 Tajima et al.
7,531,007 B2 5/2009 Sharma
7,531,137 B2 5/2009 Uluyol
7,531,349 B1 5/2009 Shepard et al.
7,536,244 B2 5/2009 Kunihiro et al.
RE40,767 E 6/2009 Peterson et al.
7,546,761 B2 6/2009 He et al.
7,552,005 B2 6/2009 Kim et al.
7,556,774 B2 7/2009 Rakow et al.
7,557,092 B2 7/2009 Lucero et al.
7,558,667 B2 7/2009 Kida
7,559,193 B2 7/2009 Iihoshi et al.
7,564,362 B2 7/2009 Cole et al.
7,565,273 B2 7/2009 Hengerer
7,567,174 B2 7/2009 Woodard et al.
7,568,376 B2 8/2009 Strohmaier et al.
7,568,377 B2 8/2009 Bhethanabotla et al.
7,571,640 B2 8/2009 Andrews
7,574,195 B2 8/2009 Krasner et al.
7,574,246 B2 8/2009 Krebs et al.
7,574,893 B2 8/2009 Mitachi et al.
7,574,905 B2 8/2009 Toya
7,575,709 B2 8/2009 Mukundan et al.
7,576,659 B2 8/2009 Lax
7,579,587 B2 8/2009 Krogh et al.
7,579,956 B2 8/2009 Chapman, Jr. et al.
7,580,137 B2 8/2009 Wilson et al.
7,580,772 B2 8/2009 Stolyar et al.
7,582,480 B2 9/2009 Audoin et al.
7,582,485 B2 9/2009 Boga et al.
7,586,409 B2 9/2009 Armstrong et al.
7,587,331 B2 9/2009 Pelletier
7,587,926 B2 9/2009 Ackerman
7,588,368 B2 9/2009 Hagen et al.
7,592,916 B2 9/2009 Staples
7,592,923 B2 9/2009 Lax
7,596,993 B2 10/2009 Fukagai et al.
7,601,250 B2 10/2009 Prohaska et al.
7,602,283 B2 10/2009 John
7,608,459 B2 10/2009 Yabuki et al.
7,611,671 B2 11/2009 Anvar et al.
7,613,554 B2 11/2009 Rollinger et al.
7,615,377 B2 11/2009 Lippard et al.
7,617,674 B2 11/2009 Gerlach
7,623,028 B2 11/2009 Kates
7,628,007 B2 12/2009 Kittelson et al.
7,628,063 B2 12/2009 Yezerets et al.
7,630,826 B2 12/2009 Wang et al.
7,631,568 B2 12/2009 Kilps et al.
7,632,178 B2 12/2009 Meneely, Jr.
7,633,386 B2 12/2009 Bennett
7,633,397 B2 12/2009 Dugan
7,642,924 B2 1/2010 Andres et al.
7,647,765 B2 1/2010 Sealy et al.
7,648,954 B2 1/2010 Saudan et al.
7,649,472 B1 1/2010 Paterno
7,651,597 B2 1/2010 Saffell et al.
7,657,384 B1 2/2010 Moses
7,659,825 B2 2/2010 Kim et al.
7,661,298 B2 2/2010 Hartmann et al.
7,665,670 B2 2/2010 Ahmed
7,670,843 B2 3/2010 Schechter et al.
7,675,423 B2 3/2010 Boling et al.
7,679,879 B2 3/2010 Furuhashi et al.
7,681,565 B2 3/2010 Fujiki
7,683,792 B2 3/2010 Araiza-Boys
7,683,794 B2 3/2010 Contreras
7,687,252 B2 3/2010 Ghosh
7,687,744 B2 3/2010 Walter et al.
7,687,770 B2 3/2010 Indo et al.
7,687,776 B2 3/2010 Baliga et al.
RE41,190 E 4/2010 Darling
7,691,592 B2 4/2010 Matsunami et al.
7,694,506 B2 4/2010 Berger et al.
7,694,547 B2 4/2010 Dutta et al.
7,696,891 B2 4/2010 Whitney
7,704,751 B2 4/2010 Palazzotto et al.
7,705,988 B2 4/2010 Richman
7,707,821 B1 5/2010 Legare
7,710,284 B2 5/2010 Dzurko et al.

(56) References Cited

U.S. PATENT DOCUMENTS 7,717,095 B2 5/2010 Liu
7,721,591 B2 5/2010 Maegawa
7,735,312 B2 6/2010 Votsmeier et al.
7,743,738 B2 6/2010 Rainear et al.
7,746,240 B2 6/2010 Vij
7,746,241 B2 6/2010 Feight et al.
7,748,213 B2 7/2010 I et al.
7,751,966 B2 7/2010 Iwazaki
7,752,837 B2 7/2010 Lihoshi et al.
7,752,901 B1 7/2010 Holmen
7,754,491 B2 7/2010 Park et al.
7,755,481 B2 7/2010 Gayden
7,755,494 B2 7/2010 Melker et al.
7,759,924 B2 7/2010 Shekhawat et al.
7,763,154 B2 7/2010 Schumann et al.
7,768,391 B2 8/2010 Koyama et al.
7,768,413 B2 8/2010 Kosuge et al.
7,768,647 B2 8/2010 Reeve et al.
7,769,534 B1 8/2010 Xu et al.
7,770,326 B2 8/2010 Al-Qassem
7,770,476 B2 8/2010 Davis et al.
7,771,113 B2 8/2010 Corbet et al.
7,774,038 B2 8/2010 Wang et al.
7,778,766 B1 8/2010 Cowgill et al.
7,779,669 B2 8/2010 Fukagai et al.
7,780,092 B2 8/2010 Ahmed
7,781,218 B2 8/2010 Furton et al.
7,782,191 B2 8/2010 Flores
7,786,879 B2 8/2010 Lax
7,786,889 B2 8/2010 Van Der Poel et al.
7,793,538 B2 9/2010 Kariya et al.
7,801,666 B2 9/2010 Mitsuda et al.
7,802,563 B2 9/2010 Behr et al.
7,805,974 B2 10/2010 Scheffler et al.
7,806,008 B2 10/2010 Binnig
7,810,313 B2 10/2010 Stewart et al.
7,815,327 B2 10/2010 Shamshoian
7,817,499 B2 10/2010 Solhjoo et al.
7,820,108 B2 10/2010 Lampotang et al.
7,821,392 B2 10/2010 Brown
7,823,377 B2 11/2010 Griard
7,829,714 B2 11/2010 Whateley et al.
7,832,260 B2 11/2010 Tanaka
7,833,397 B2 11/2010 Kimura
7,835,005 B2 11/2010 Appel et al.
7,836,758 B2 11/2010 Aono et al.
7,837,663 B2 11/2010 MacDonald et al.
7,838,288 B2 11/2010 Matsunami et al.
7,838,297 B2 11/2010 Widmer et al.
7,838,799 B2 11/2010 Freedman
7,840,366 B1 11/2010 Moses et al.
7,841,173 B2 11/2010 Clever
7,842,284 B2 11/2010 Johnson
7,843,324 B2 11/2010 Penney et al.
7,846,742 B2 12/2010 Sapir et al.
7,848,732 B2 12/2010 Thomas
7,849,672 B2 12/2010 Shibata et al.
7,849,844 B2 12/2010 Rosel
7,851,225 B2 12/2010 Colvin, Jr. et al.
7,854,161 B2 12/2010 Hjorsberg et al.
7,858,378 B2 12/2010 Yabuki et al.
7,861,515 B2 1/2011 Brahma
7,864,322 B2 1/2011 Carpenter et al.
7,866,202 B2 1/2011 Chen et al.
7,874,285 B2 1/2011 Barnikow et al.
7,879,565 B2 2/2011 Matsunami et al.
7,880,468 B2 2/2011 Szyperski et al.
7,881,858 B2 2/2011 Kress et al.
7,886,523 B1 2/2011 Legare
7,886,577 B2 2/2011 Zeng
7,889,088 B1 2/2011 Billman
RE42,192 E 3/2011 Schabron et al.
7,897,400 B2 3/2011 Timmins et al.
7,900,439 B2 3/2011 Genslak et al.
7,900,500 B2 3/2011 Krafthefer
7,900,616 B2 3/2011 Saunders
7,904,053 B2 3/2011 Krasner et al.
7,905,154 B2 3/2011 Jones, Jr.
7,907,052 B2 3/2011 Delaney, Jr.
7,908,991 B2 3/2011 Woods et al.
7,913,540 B2 3/2011 Brasfield
7,913,550 B2 3/2011 Schoenthaler et al.
7,915,047 B2 3/2011 Thorn et al.
7,919,304 B2 4/2011 Egan et al.
7,920,842 B2 4/2011 Martin et al.
7,920,972 B2 4/2011 Szyperski et al.
7,921,706 B2 4/2011 Sumitani
7,926,483 B2 4/2011 Lundeen
7,926,734 B2 4/2011 Dobler et al.
7,930,876 B2 4/2011 Thouvenel et al.
7,930,923 B2 4/2011 Patel et al.
7,930,924 B2 4/2011 Krogh et al.
7,932,482 B2 4/2011 Norwood et al.
7,933,710 B2 4/2011 Tanaka et al.
7,937,216 B2 5/2011 Humphrey
7,944,352 B2 5/2011 Drake et al.
7,945,301 B2 5/2011 Krebs et al.
H2256 H 6/2011 Rayms-Keller
7,954,364 B2 6/2011 Shoda
7,957,919 B2 6/2011 Marconi
7,963,453 B2 6/2011 Peterson et al.
7,963,460 B2 6/2011 Jorgensen
7,968,516 B2 6/2011 Stracher et al.
7,969,296 B1 6/2011 Stell
7,972,277 B2 7/2011 Oki et al.
7,972,488 B2 7/2011 Oya et al.
7,973,669 B2 7/2011 Pham et al.
7,977,955 B2 7/2011 Katsuyama et al.
7,978,083 B2 7/2011 Melker et al.
7,987,039 B2 7/2011 Takagawa
7,987,695 B2 8/2011 Kilps et al.
7,988,771 B2 8/2011 Anikhindi et al.
7,993,587 B2 8/2011 Mayer et al.
7,997,064 B2 8/2011 Arlt et al.
7,998,419 B2 8/2011 Furuhashi et al.
8,003,399 B2 8/2011 Song et al.
8,005,603 B2 8/2011 Fisher et al.
8,006,542 B2 8/2011 Jones, Jr.
8,006,670 B2 8/2011 Rollinger et al.
8,016,205 B2 9/2011 Drew
8,019,525 B2 9/2011 DeBastos et al.
8,024,103 B2 9/2011 Kassner
8,026,103 B2 9/2011 Van Herpen
8,026,804 B2 9/2011 Wu et al.
8,026,825 B2 9/2011 Santos
8,029,153 B2 10/2011 Jorgensen
8,031,335 B2 10/2011 Wang et al.
8,034,290 B1 10/2011 Skiba et al.
8,036,814 B2 10/2011 Weber et al.
8,038,778 B2 10/2011 Chan et al.
8,038,946 B1 10/2011 Harper et al.
8,041,516 B2 10/2011 Angell et al.
8,042,385 B2 10/2011 Brennan et al.
8,042,528 B2 10/2011 Gates et al.
8,047,163 B2 11/2011 Tian et al.
8,049,619 B2 11/2011 Armstrong et al.
8,054,188 B2 11/2011 Harkins et al.
8,056,540 B2 11/2011 DeBastos et al.
8,059,150 B2 11/2011 Gal
8,065,871 B1 11/2011 Fraser
8,066,859 B2 11/2011 Johnston et al.
8,066,939 B2 11/2011 Elrod
8,073,405 B2 12/2011 Tougou
8,075,759 B2 12/2011 Schnaibel et al.
8,077,046 B1 12/2011 Wong
8,077,048 B2 12/2011 Almiman
8,078,388 B2 12/2011 Powell
8,079,351 B2 12/2011 Uhrich et al.
8,080,206 B2 12/2011 Leddy et al.
8,083,575 B2 12/2011 Kim
8,085,152 B2 12/2011 Liu
8,086,266 B2 12/2011 Kotidis
8,087,290 B2 1/2012 Wickert et al.
8,091,404 B2 1/2012 Sawada et al.

(56) References Cited

U.S. PATENT DOCUMENTS 8,091,416 B2 1/2012 Wang et al.
8,091,538 B2 1/2012 Hartmann et al.
8,095,296 B2 1/2012 Kirstaetter et al.
8,099,946 B2 1/2012 Hinz et al.
8,099,947 B2 1/2012 Makki et al.
8,103,430 B2 1/2012 Aliakbarzadeh
8,104,334 B2 1/2012 Wang et al.
8,105,584 B2 1/2012 Fallon
8,107,920 B2 1/2012 Ben Ayed
8,109,452 B2 2/2012 Akisada et al.
8,112,984 B2 2/2012 Dietl et al.
8,114,904 B2 2/2012 Yang et al.
8,120,501 B2 2/2012 Mancini
8,122,753 B2 2/2012 Tryfonos et al.
8,123,923 B2 2/2012 Prohaska et al.
8,127,593 B2 3/2012 Moularat
8,130,105 B2 3/2012 Al-Ali et al.
8,132,450 B2 3/2012 Shibata et al.
8,133,434 B2 3/2012 Bankers et al.
8,134,458 B2 3/2012 Lund
8,134,470 B2 3/2012 Agurs
8,137,979 B2 3/2012 Combes et al.
8,143,068 B2 3/2012 Colvin, Jr. et al.
8,146,346 B2 4/2012 Ishibashi
8,146,352 B2 4/2012 Parnin
8,146,562 B2 4/2012 Yezerets et al.
8,148,995 B2 4/2012 Hashimoto et al.
8,152,992 B2 4/2012 Smela et al.
8,153,065 B2 4/2012 Zang et al.
8,153,439 B2 4/2012 Zamborini et al.
8,154,093 B2 4/2012 Bradley et al.
8,156,728 B2 4/2012 Hinz et al.
8,161,808 B2 4/2012 Crawford et al.
8,165,719 B2 4/2012 Kinney et al.
8,166,749 B2 5/2012 Gady
8,171,720 B2 5/2012 Wang et al.
8,171,721 B2 5/2012 Boddy et al.
8,171,781 B2 5/2012 Shibata et al.
8,173,430 B2 5/2012 Cohen-Arazi et al.
8,175,884 B1 5/2012 Morris
8,186,205 B2 5/2012 Wehmeier et al.
8,187,887 B2 5/2012 Swager et al.
8,190,223 B2 5/2012 Al-Ali et al.
8,190,352 B2 5/2012 Brandt et al.
8,190,397 B2 5/2012 Kurokawa
8,195,354 B2 6/2012 Kariya et al.
8,196,903 B2 6/2012 Jorgensen
8,200,411 B2 6/2012 DeBastos et al.
8,201,444 B2 6/2012 Wang et al.
8,203,445 B2 6/2012 Recker et al.
8,203,458 B2 6/2012 Kaneblei et al.
8,205,436 B2 6/2012 Berke et al.
8,205,437 B2 6/2012 Arnold et al.
8,209,110 B2 6/2012 Weber et al.
8,209,964 B2 7/2012 Kesse
8,211,035 B2 7/2012 Melker et al.
8,211,208 B2 7/2012 Chan et al.
8,214,176 B2 7/2012 Iwazaki et al.
8,215,291 B2 7/2012 DeBastos et al.
8,219,278 B2 7/2012 Sawada et al.
8,224,282 B2 7/2012 Songkakul et al.
8,225,647 B2 7/2012 Mukai
8,230,677 B2 7/2012 Devarakonda et al.
8,230,716 B2 7/2012 Nelson et al.
8,232,072 B2 7/2012 Kalnik et al.
8,232,884 B2 7/2012 Pattok et al.
8,234,030 B2 7/2012 Sugimoto
8,240,129 B2 8/2012 Yezerets et al.
8,240,130 B2 8/2012 Sawada et al.
8,240,193 B2 8/2012 Frauhammer et al.
8,242,899 B2 8/2012 Albert et al.
8,245,497 B2 8/2012 Yoda et al.
8,245,566 B2 8/2012 Wehmeier et al.
8,245,567 B2 8/2012 Wang et al.
8,246,549 B2 8/2012 Janski et al.
8,249,510 B2 8/2012 Chabin et al.
8,249,827 B2 8/2012 Nelson et al.
8,252,099 B2 8/2012 Worrilow
8,253,553 B2 8/2012 Wedig et al.
8,253,558 B2 8/2012 Emerson et al.
8,256,208 B2 9/2012 Wills et al.
8,256,264 B2 9/2012 Bosi et al.
8,258,969 B1 9/2012 Billman
8,260,576 B2 9/2012 Iwazaki et al.
8,261,540 B2 9/2012 Konstandopoulos et al.
8,264,326 B2 9/2012 Hayashi et al.
8,268,241 B1 9/2012 Cooper
8,269,625 B2 9/2012 Hoy et al.
8,272,250 B2 9/2012 Wang et al.
8,273,298 B2 9/2012 Newell
8,274,393 B2 9/2012 Ales et al.
8,281,576 B2 10/2012 Parnin
8,286,417 B2 10/2012 Allmer et al.
8,286,603 B2 10/2012 Sid
8,286,610 B2 10/2012 Moriya
8,287,811 B1 10/2012 Harper et al.
8,290,688 B2 10/2012 Watson
8,294,567 B1 10/2012 Stell
8,297,040 B2 10/2012 Rosel
8,302,378 B2 11/2012 Miyoshi et al.
8,303,174 B2 11/2012 Kasahara
8,303,697 B2 11/2012 Chan et al.
8,307,699 B2 11/2012 Sawada et al.
8,309,310 B2 11/2012 Enderle et al.
8,310,016 B2 11/2012 Stetter
8,311,721 B2 11/2012 Whitney et al.
8,320,751 B2 11/2012 Porchia et al.
8,327,628 B2 12/2012 Ruona et al.
8,327,696 B2 12/2012 Baars et al.
8,329,099 B1 12/2012 Skiba et al.
8,333,125 B2 12/2012 Tsai et al.
8,333,816 B2 12/2012 Kummer et al.
8,334,387 B2 12/2012 Whateley et al.
8,334,505 B2 12/2012 Robinson et al.
8,336,291 B2 12/2012 Hanari et al.
8,336,525 B2 12/2012 Runde et al.
8,341,937 B2 1/2013 I et al.
8,341,938 B2 1/2013 Votsmeier et al.
8,350,710 B2 1/2013 Logan et al.
8,354,935 B2 1/2013 Rauworth
8,357,304 B2 1/2013 Reich et al.
8,359,826 B2 1/2013 Kitazawa
8,366,630 B2 2/2013 Haick et al.
8,368,754 B2 2/2013 Flores et al.
8,371,547 B2 2/2013 Wilkowske
8,374,586 B2 2/2013 Bentkovski et al.
8,375,913 B2 2/2013 Kwiecinski et al.
8,377,706 B2 2/2013 Hong et al.
8,378,817 B2 2/2013 Fox
8,384,397 B2 2/2013 Bromberg et al.
8,392,029 B2 3/2013 Nakamoto et al.
8,393,141 B2 3/2013 Sebestyen et al.
8,400,317 B2 3/2013 Johnson, Jr. et al.
8,401,727 B2 3/2013 Arlt et al.
8,407,983 B2 4/2013 Mukai
8,407,986 B2 4/2013 Hahn
8,410,935 B2 4/2013 Jackson
8,413,421 B2 4/2013 Fujimoto
8,413,422 B2 4/2013 Kasahara
8,413,497 B2 4/2013 Kayama et al.
8,418,438 B2 4/2013 Shimomura et al.
8,418,942 B2 4/2013 Suda et al.
8,423,192 B2 4/2013 Liu
8,423,243 B2 4/2013 Harima
8,424,288 B2 4/2013 De Tricaud et al.
8,426,208 B2 4/2013 Swager et al.
8,426,215 B2 4/2013 Mueller et al.
8,426,932 B2 4/2013 Stetter
8,428,954 B2 4/2013 Morris
8,430,096 B2 4/2013 Chambers
8,432,451 B2 4/2013 Cetin et al.
RE44,214 E 5/2013 Peterson et al.
8,434,349 B2 5/2013 Blomberg et al.
8,435,448 B2 5/2013 Park et al.

(56) References Cited

U.S. PATENT DOCUMENTS 8,437,965 B2 5/2013 Sjong
8,440,068 B2 5/2013 Kimura
8,441,357 B2 5/2013 Ohya
8,442,611 B2 5/2013 Santini, Jr. et al.
8,447,495 B2 5/2013 Pearce et al.
8,447,528 B2 5/2013 Gentala et al.
8,448,739 B2 5/2013 Kolich
8,451,132 B1 5/2013 Van Vleet
8,459,005 B2 6/2013 Zhang
8,461,354 B2 6/2013 Babudri et al.
8,464,663 B2 6/2013 Kodat
8,468,799 B2 6/2013 Post et al.
8,469,010 B2 6/2013 Inoue
8,469,244 B2 6/2013 Helf et al.
8,470,933 B2 6/2013 Thorn et al.
8,476,023 B2 7/2013 Lazarus et al.
8,481,270 B2 7/2013 Gniewek et al.
8,481,324 B2 7/2013 Haick et al.
8,481,470 B2 7/2013 Jones, Jr.
8,484,949 B2 7/2013 Sebestyen et al.
8,487,240 B2 7/2013 Koehl
8,489,361 B2 7/2013 Umehara
8,490,385 B2 7/2013 Miyoshi et al.
8,490,465 B2 7/2013 Ante et al.
8,490,476 B2 7/2013 Hopka et al.
8,495,860 B2 7/2013 Gresens
8,496,737 B2 7/2013 Kim et al.
8,499,545 B2 8/2013 Busch et al.
8,499,613 B2 8/2013 Ziglioli et al.
8,500,442 B2 8/2013 Knittel et al.
8,505,370 B2 8/2013 Miller
8,505,371 B2 8/2013 Zimmerman et al.
8,515,710 B2 8/2013 Wang et al.
8,518,663 B2 8/2013 Trevejo et al.
8,518,703 B1 8/2013 Wright
8,519,182 B2 8/2013 Salisbury et al.
8,521,354 B2 8/2013 Sasaki
8,521,405 B2 8/2013 Maruyama
8,525,665 B1 9/2013 Trundle et al.
8,525,666 B2 9/2013 Melker et al.
8,528,319 B2 9/2013 Wilhelm et al.
8,529,846 B1 9/2013 Wright
8,534,258 B2 9/2013 Cristoforo
8,539,757 B2 9/2013 Hirota et al.
8,539,914 B2 9/2013 Kerns et al.
8,542,107 B2 9/2013 Dolan
8,542,115 B2 9/2013 Karim et al.
8,543,288 B2 9/2013 Bligard et al.
8,544,258 B2 10/2013 Brown et al.
8,547,237 B2 10/2013 Adebimpe
8,550,368 B2 10/2013 Butler et al.
8,551,214 B2 10/2013 Dudar et al.
8,555,613 B2 10/2013 Wang et al.
8,555,618 B2 10/2013 Bauer et al.
8,555,700 B2 10/2013 Dikken
8,556,505 B2 10/2013 Akins et al.
8,558,696 B2 10/2013 Baumann et al.
8,561,387 B2 10/2013 Fokkelman
8,566,023 B2 10/2013 Riggins et al.
8,572,952 B2 11/2013 Parnin
8,577,645 B2 11/2013 Turin et al.
8,583,349 B2 11/2013 Anilovich et al.
8,584,189 B2 11/2013 Emerson et al.
8,586,383 B2 11/2013 Walte et al.
8,590,289 B2 11/2013 Maki
8,596,045 B2 12/2013 Tuomivaara et al.
8,597,956 B2 12/2013 Willner et al.
8,602,854 B1 12/2013 Moore
8,608,835 B2 12/2013 Busch
8,613,219 B2 12/2013 Kitaura et al.
8,617,498 B2 12/2013 Geveci et al.
8,618,939 B2 12/2013 Nabata et al.
8,618,942 B1 12/2013 Billman
8,621,849 B2 1/2014 Vernassa et al.
8,621,911 B2 1/2014 McFaul
8,631,690 B2 1/2014 Kowalkowski et al.
8,632,666 B2 1/2014 Schlichte et al.
8,635,900 B2 1/2014 Ante et al.
8,638,215 B2 1/2014 Kates
8,638,453 B2 1/2014 Kessler
8,641,611 B2 2/2014 Urushihata et al.
8,641,878 B2 2/2014 Nemes
8,646,253 B2 2/2014 Gloeckle et al.
8,646,324 B2 2/2014 Plonka et al.
8,646,341 B2 2/2014 Schulten et al.
8,648,731 B2 2/2014 Su et al.
8,649,840 B2 2/2014 Sheppard, Jr. et al.
8,649,961 B2 2/2014 Hawkins et al.
8,650,942 B2 2/2014 Klenk et al.
8,652,040 B2 2/2014 LeBoeuf et al.
8,653,439 B2 2/2014 Nauka et al.
8,659,416 B1 2/2014 Higgins
8,661,791 B2 3/2014 Furness
8,666,588 B2 3/2014 Geilen et al.
8,668,874 B2 3/2014 Tao et al.
8,668,884 B2 3/2014 Kim et al.
8,669,878 B1 3/2014 Vantilburg
8,671,737 B2 3/2014 Brasfield
8,674,813 B2 3/2014 Alexander et al.
8,674,842 B2 3/2014 Zishaan
8,683,786 B2 4/2014 Ruona et al.
8,683,856 B2 4/2014 Kitaura
8,687,188 B2 4/2014 Long et al.
8,689,536 B2 4/2014 Kopacek et al.
8,691,066 B2 4/2014 Collins
8,691,390 B2 4/2014 Ramamurthy
8,694,197 B2 4/2014 Rajagopalan et al.
8,699,029 B2 4/2014 Steel et al.
8,701,463 B2 4/2014 Brasfield
8,702,618 B2 4/2014 MacDonald et al.
8,703,067 B2 4/2014 Woolley
8,704,171 B2 4/2014 Robinson et al.
8,707,677 B2 4/2014 Kowalkowski et al.
8,707,807 B2 4/2014 Yadav et al.
8,709,721 B2 4/2014 Abe et al.
8,715,587 B1 5/2014 Downs
8,716,027 B2 5/2014 Bronchetti
8,720,251 B2 5/2014 Henshaw et al.
8,742,897 B2 6/2014 Jackson
8,742,932 B2 6/2014 Casares
8,745,971 B2 6/2014 Yezerets et al.
8,748,111 B2 6/2014 Mershin et al.
8,749,392 B2 6/2014 Wedig et al.
8,752,368 B2 6/2014 Ante et al.
8,755,942 B2 6/2014 Bonilla et al.
8,759,111 B2 6/2014 Crunaire et al.
8,759,791 B1 6/2014 Hug et al.
8,760,304 B2 6/2014 Pincu
8,760,508 B2 6/2014 Brantley et al.
8,765,481 B2 7/2014 Waldvogel et al.
8,769,928 B2 7/2014 Yeager et al.
8,769,937 B2 7/2014 Yanakiev et al.
8,770,008 B2 7/2014 Carlson et al.
8,770,771 B2 7/2014 Preta et al.
8,771,489 B2 7/2014 Xiao et al.
8,783,019 B2 7/2014 Bedford et al.
8,786,454 B2 7/2014 Siddall
8,791,828 B2 7/2014 Harkins et al.
8,793,849 B1 8/2014 Bhethanabotla et al.
8,794,057 B2 8/2014 Ardanese et al.
8,795,978 B2 8/2014 Steyn et al.
8,803,677 B1 8/2014 Miller
8,803,696 B1 8/2014 Dunyan
8,806,914 B2 8/2014 Brasfield
8,810,426 B1 8/2014 Morris
8,813,546 B2 8/2014 Takahashi et al.
8,818,713 B2 8/2014 Kumar et al.
8,820,051 B2 9/2014 Barasa et al.
8,820,054 B2 9/2014 Bisaiji et al.
8,823,400 B2 9/2014 Hocken et al.
8,826,723 B2 9/2014 Henry
8,826,730 B2 9/2014 Koizumi et al.
8,830,057 B1 9/2014 Poursohi et al.
8,838,396 B2 9/2014 Gentala et al.

(56) References Cited

U.S. PATENT DOCUMENTS 8,843,263 B2 9/2014 Willard
8,844,337 B2 9/2014 Kountotsis et al.
8,844,343 B2 9/2014 Kim
8,846,406 B1 9/2014 Martin et al.
8,847,773 B2 9/2014 Rauworth et al.
8,852,513 B1 10/2014 Speer et al.
8,852,945 B2 10/2014 Lee et al.
8,852,946 B2 10/2014 Lee et al.
8,854,362 B1 10/2014 Poursohi et al.
8,857,463 B1 10/2014 Carruth et al.
8,857,662 B2 10/2014 Hoppe et al.
8,859,995 B2 10/2014 Liu et al.
8,863,497 B1 10/2014 Legare
8,863,499 B2 10/2014 Kowalkowski et al.
8,868,378 B2 10/2014 Batzler et al.
8,869,607 B2 10/2014 Levijoki et al.
8,871,148 B2 10/2014 Wendland et al.
8,881,508 B2 11/2014 Geveci
8,884,751 B2 11/2014 Baldocchi et al.
8,887,490 B2 11/2014 Wentz et al.
8,888,979 B2 11/2014 Nemes
8,890,701 B2 11/2014 Mahajan et al.
8,893,475 B2 11/2014 Geveci et al.
8,899,098 B2 12/2014 Senft et al.
8,907,803 B2 12/2014 Martin
8,910,466 B2 12/2014 Kowalkowski et al.
8,910,508 B2 12/2014 Liwa
8,912,003 B2 12/2014 Monk
8,912,909 B2 12/2014 Al-Ali et al.
8,914,221 B2 12/2014 Peters et al.
8,915,022 B2 12/2014 Klink et al.
8,915,645 B2 12/2014 Genssle et al.
8,916,037 B1 12/2014 Mayer et al.
8,917,078 B2 12/2014 Kondo et al.
8,917,186 B1 12/2014 Grant
8,920,627 B2 12/2014 Fleischer et al.
8,922,219 B2 12/2014 Li et al.
8,922,335 B2 12/2014 Deweese et al.
8,924,131 B2 12/2014 Kowalkowski et al.
8,928,338 B2 1/2015 Nelson et al.
8,930,121 B2 1/2015 Rajagopalan et al.
8,931,327 B2 1/2015 Pearce et al.
8,931,712 B2 1/2015 Nagano et al.
8,932,533 B2 1/2015 Kruglick
8,935,084 B2 1/2015 Lin et al.
8,947,230 B1 2/2015 Gettings et al.
8,947,249 B1 2/2015 Dore et al.
8,950,238 B2 2/2015 Shaw et al.
8,951,396 B2 2/2015 Nemes
8,951,503 B2 2/2015 Singaram et al.
8,955,307 B2 2/2015 Yahata et al.
8,955,515 B2 2/2015 Rakow et al.
8,955,765 B2 2/2015 Porchia et al.
8,956,571 B2 2/2015 Goldstein et al.
8,959,904 B2 2/2015 Porras et al.
8,959,982 B2 2/2015 Pearce et al.
8,962,334 B2 2/2015 Lee et al.
8,963,730 B1 2/2015 Dickerman
8,966,882 B2 3/2015 Tylutki et al.
8,968,646 B2 3/2015 Matheis et al.
8,969,069 B2 3/2015 Ahn et al.
8,969,083 B2 3/2015 Lee et al.
8,969,084 B2 3/2015 Lee et al.
8,969,096 B2 3/2015 Hicks et al.
8,970,383 B2 3/2015 Liou et al.
8,973,430 B2 3/2015 Nagaoka et al.
8,981,498 B2 3/2015 Ziglioli
8,984,867 B2 3/2015 Anilovich et al.
8,986,998 B2 3/2015 Lee et al.
8,992,770 B2 3/2015 Gong et al.
8,997,726 B2 4/2015 Eser et al.
9,007,222 B2 4/2015 Mittleman et al.
9,007,224 B1 4/2015 Fadell et al.
9,010,087 B1 4/2015 Upadhyay et al.
9,010,172 B2 4/2015 Xia et al.
9,012,169 B2 4/2015 Schilling
9,013,297 B1 4/2015 Dey et al.
9,014,859 B2 4/2015 Isaksson et al.
9,018,016 B2 4/2015 Crunaire et al.
9,019,109 B2 4/2015 Warmack et al.
9,019,111 B1 4/2015 Sloo et al.
9,020,764 B2 4/2015 Walte et al.
9,021,789 B2 5/2015 Sawada et al.
9,021,860 B2 5/2015 Nelson
9,026,386 B2 5/2015 Jiang
9,027,539 B2 5/2015 Miyashita
9,028,570 B2 5/2015 Suematsu et al.
9,028,615 B2 5/2015 Eglmeier et al.
9,028,751 B2 5/2015 Page et al.
9,030,319 B1 5/2015 Haynes
9,030,329 B2 5/2015 Rutherford et al.
9,030,330 B1 5/2015 Nichols, Jr.
9,033,553 B2 5/2015 Li
9,038,369 B2 5/2015 Khaled et al.
9,046,021 B2 6/2015 DeGeorge
9,047,754 B2 6/2015 Kim
9,050,561 B1 6/2015 Shetney et al.
9,051,866 B2 6/2015 Yanakiev et al.
9,051,867 B2 6/2015 Fontana
9,051,868 B2 6/2015 Scherer et al.
9,052,280 B2 6/2015 Katsurahara et al.
9,053,626 B2 6/2015 Cristoforo
9,057,338 B2 6/2015 Levijoki et al.
9,057,669 B2 6/2015 van Straaten et al.
9,062,623 B2 6/2015 Verdier et al.
9,062,637 B2 6/2015 Sager et al.
9,068,226 B2 6/2015 Matsunami et al.
9,068,491 B2 6/2015 Cavataio et al.
9,068,493 B2 6/2015 Tanioka
9,068,937 B2 6/2015 Kilinc et al.
9,070,272 B2 6/2015 Gettings et al.
9,074,045 B2 7/2015 Fernandez et al.
9,074,507 B2 7/2015 Tylutki et al.
9,074,539 B2 7/2015 Yahata et al.
9,080,782 B1 7/2015 Sheikh
9,082,274 B2 7/2015 Goto et al.
9,082,275 B2 7/2015 Baker
9,086,391 B2 7/2015 Lee et al.
9,091,226 B2 7/2015 Zimmerschied et al.
9,097,165 B2 8/2015 Kim
9,100,368 B2 8/2015 Rezvani et al.
9,102,417 B1 8/2015 Young
9,103,775 B2 8/2015 Bradley et al.
9,103,796 B2 8/2015 Song
9,104,538 B2 8/2015 Garrett et al.
9,109,480 B2 8/2015 Kowalkowski et al.
9,109,481 B2 8/2015 Martin et al.
9,109,493 B2 8/2015 Lin et al.
9,109,527 B2 8/2015 Barnikow et al.
9,110,007 B2 8/2015 Birecki et al.
9,110,041 B2 8/2015 Flanders
9,111,426 B2 8/2015 Engelmann et al.
9,113,052 B1 8/2015 Scalisi et al.
9,113,836 B2 8/2015 Bernstein et al.
9,115,629 B2 8/2015 Hopka et al.
9,115,630 B1 8/2015 Geveci et al.
9,121,323 B2 9/2015 Feldmann et al.
9,123,244 B2 9/2015 Daman et al.
9,124,955 B2 9/2015 Geva et al.
9,125,255 B2 9/2015 Ramer et al.
9,125,590 B2 9/2015 Tang et al.
9,125,607 B2 9/2015 Wang et al.
9,125,625 B2 9/2015 Wang et al.
9,127,301 B2 9/2015 Krebs et al.
9,128,139 B2 9/2015 Carbonaro et al.
9,129,496 B1 9/2015 Jackson
9,135,794 B1 9/2015 Anderson et al.
9,137,108 B2 9/2015 Rezvani et al.
9,138,524 B2 9/2015 Bluchel et al.
9,140,677 B2 9/2015 Mershin et al.
9,142,118 B2 9/2015 Patenaude et al.
9,142,119 B1 9/2015 Grant
9,144,396 B2 9/2015 Choe et al.
9,144,772 B2 9/2015 Pfister et al.

(56) References Cited

U.S. PATENT DOCUMENTS 9,145,842 B2 9/2015 Takahashi et al.
9,145,851 B2 9/2015 Bossmeyer et al.
9,146,222 B2 9/2015 Su et al.
9,147,329 B2 9/2015 Bugg, Jr.
9,151,729 B2 10/2015 Rabbett
9,151,767 B2 10/2015 Yang
9,153,107 B2 10/2015 Austin
9,157,390 B2 10/2015 Song et al.
9,159,218 B2 10/2015 Simoncic et al.
9,160,987 B1 10/2015 Kasmir et al.
9,163,575 B2 10/2015 Pursifull
9,164,071 B2 10/2015 McFaul
9,167,100 B2 10/2015 Bang
9,169,795 B2 10/2015 Jammoussi et al.
9,170,144 B2 10/2015 Qi
9,170,228 B2 10/2015 Takulapalli
9,170,229 B2 10/2015 Paggel et al.
9,170,243 B2 10/2015 Yabuki et al.
9,170,258 B2 10/2015 Withrow, III et al.
9,171,453 B2 10/2015 Warmack et al.
9,172,606 B2 10/2015 Rezvani et al.
9,172,742 B2 10/2015 Rezvani et al.
RE45,804 E 11/2015 Mancini
9,175,415 B2 11/2015 Hong et al.
9,175,625 B2 11/2015 Kumar et al.
9,179,220 B2 11/2015 Morris
9,181,843 B2 11/2015 Kim et al.
9,181,878 B2 11/2015 Moeckly et al.
9,182,366 B2 11/2015 Izawa et al.
9,183,731 B1 11/2015 Bokhary
9,183,733 B2 11/2015 Kates
9,183,736 B2 11/2015 Sloo et al.
9,183,737 B1 11/2015 Billman
9,186,090 B2 11/2015 Chu et al.
9,188,073 B2 11/2015 Chen et al.
9,188,075 B2 11/2015 Varney
9,188,568 B2 11/2015 Ebeler et al.
9,191,277 B2 11/2015 Rezvani et al.
9,191,909 B2 11/2015 Rezvani et al.
9,194,268 B2 11/2015 Kowalkowski et al.
9,194,273 B2 11/2015 Janssen et al.
9,194,358 B1 11/2015 Avramidis
9,194,807 B2 11/2015 Song
9,196,146 B1 11/2015 Vicente
9,202,363 B1 12/2015 Grant
9,203,695 B2 12/2015 Rezvani et al.
9,206,727 B2 12/2015 Liu et al.
9,208,676 B2 12/2015 Fadell et al.
9,211,356 B2 12/2015 Gruenbacher et al.
9,212,610 B2 12/2015 Chen et al.
9,217,737 B2 12/2015 Boyd et al.
9,224,278 B2 12/2015 Bernal et al.
9,226,481 B1 1/2016 Paripati
9,228,523 B2 1/2016 Varney
9,228,923 B2 1/2016 Zimmerman et al.
9,230,371 B2 1/2016 Jecks et al.
9,233,082 B2 1/2016 Kato et al.
9,234,871 B2 1/2016 Fleischer et al.
9,235,976 B2 1/2016 Sloo et al.
9,244,474 B2 1/2016 Smith et al.
9,247,215 B1 1/2016 Athan
9,248,707 B2 2/2016 Zhou et al.
9,249,453 B2 2/2016 Kato et al.
9,249,737 B2 2/2016 Fitzgerald et al.
9,250,222 B2 2/2016 Furton et al.
9,250,667 B2 2/2016 Liwa
9,251,687 B2 2/2016 Thompson et al.
9,251,696 B2 2/2016 Sloo et al.
9,255,435 B2 2/2016 Weidenbacher
9,255,536 B2 2/2016 Eser et al.
9,255,873 B2 2/2016 Sakamoto et al.
9,259,498 B2 2/2016 Shen
9,260,738 B2 2/2016 Moularat et al.
9,261,006 B2 2/2016 Mitchell et al.
9,261,033 B2 2/2016 Sealy et al.
9,261,481 B2 2/2016 Mintah et al.
9,261,885 B2 2/2016 Tryfonos et al.
9,262,901 B1 2/2016 Mona
9,262,902 B2 2/2016 Costa
9,262,906 B2 2/2016 Poder et al.
9,262,909 B1 2/2016 Grant
9,265,235 B2 2/2016 Inoue et al.
9,266,072 B2 2/2016 Ingledew et al.
9,267,866 B2 2/2016 Almirall et al.
9,273,587 B2 3/2016 Khaled et al.
9,279,382 B2 3/2016 Genko
9,279,791 B2 3/2016 Fukui et al.
9,280,884 B1 3/2016 Schultz et al.
9,291,610 B2 3/2016 Zelepouga et al.
9,296,390 B2 3/2016 Martin et al.
9,297,286 B2 3/2016 Kruer et al.
9,297,843 B2 3/2016 Gibson et al.
9,310,347 B2 4/2016 Xu et al.
9,310,781 B2 4/2016 Lee et al.
9,311,807 B2 4/2016 Schultz et al.
9,311,811 B1 4/2016 Szewczyk et al.
9,313,761 B2 4/2016 Rezvani et al.
9,315,848 B2 4/2016 Haick et al.
9,315,852 B2 4/2016 Swartz
9,316,565 B2 4/2016 Kappaganthu et al.
9,316,574 B2 4/2016 Sakamoto et al.
9,316,626 B2 4/2016 Reinhardt et al.
9,318,015 B2 4/2016 Kates
9,327,148 B2 5/2016 Holoch et al.
9,328,645 B2 5/2016 Tylutki et al.
9,329,191 B2 5/2016 Chang et al.
9,330,550 B2 5/2016 Zribi et al.
9,332,057 B2 5/2016 Rezvani et al.
9,332,322 B2 5/2016 Niemeyer et al.
9,335,310 B2 5/2016 Lee et al.
9,347,356 B2 5/2016 Qi
9,347,678 B2 5/2016 Stakutis et al.
9,347,916 B2 5/2016 Moularat et al.
9,351,675 B2 5/2016 Al-Ali et al.
9,352,065 B2 5/2016 Habbel
9,353,966 B2 5/2016 Finkam
9,356,215 B2 5/2016 Iriyama
9,357,490 B2 5/2016 Kates
9,360,181 B2 6/2016 Li
9,360,394 B2 6/2016 Walter et al.
9,366,192 B2 6/2016 Byrd et al.
9,371,972 B2 6/2016 Li
9,376,435 B2 6/2016 George et al.
9,376,952 B2 6/2016 Kowalkowski et al.
9,376,976 B2 6/2016 Baumann et al.
9,376,991 B2 6/2016 Dudar et al.
9,377,447 B2 6/2016 Mershin et al.
9,382,861 B2 7/2016 Jankovic et al.
9,388,728 B2 7/2016 Chandrasekaran et al.
9,390,565 B2 7/2016 Thompson et al.
9,395,324 B2 7/2016 Zribi et al.
9,396,623 B2 7/2016 Lasker
9,399,912 B2 7/2016 McAlary et al.
9,399,958 B2 7/2016 Sano et al.
9,399,961 B2 7/2016 Lehmen et al.
9,401,950 B2 7/2016 Rezvani et al.
9,404,832 B2 8/2016 Kimura et al.
9,407,684 B2 8/2016 Rezvani et al.
9,407,685 B2 8/2016 Rezvani et al.
9,408,556 B2 8/2016 Wang et al.
9,410,896 B2 8/2016 Sajdak et al.
9,412,258 B2 8/2016 Matsuoka et al.
9,412,260 B2 8/2016 Kates
9,413,810 B2 8/2016 Rezvani et al.
9,415,345 B2 8/2016 Holbert et al.
9,416,708 B2 8/2016 Schroeder et al.
9,416,735 B2 8/2016 Varney
9,416,755 B2 8/2016 Dudar
9,417,226 B2 8/2016 Amisar
9,418,828 B2 8/2016 Mennito et al.
9,421,294 B2 8/2016 Yamada et al.
9,422,847 B2 8/2016 Osburn et al.
9,429,062 B2 8/2016 Osburn et al.
9,429,090 B2 8/2016 Kennie et al.

(56) References Cited

U.S. PATENT DOCUMENTS 9,429,537 B2 8/2016 Kang et al.
9,429,551 B2 8/2016 Podgorney
9,430,927 B2 8/2016 Yu et al.
9,430,933 B2 8/2016 Fadell et al.
9,437,092 B2 9/2016 Warmack et al.
9,437,097 B2 9/2016 Poursohi et al.
9,441,564 B2 9/2016 Surnilla et al.
9,442,073 B2 9/2016 Joly et al.
9,444,244 B2 9/2016 Hooper et al.
9,448,218 B2 9/2016 Lee et al.
9,449,491 B2 9/2016 Sager et al.
9,449,492 B2 9/2016 Dixon et al.
9,453,450 B2 9/2016 Sun et al.
9,453,451 B2 9/2016 Matsumoto et al.
9,453,472 B2 9/2016 Levijoki et al.
9,458,776 B2 10/2016 Haehara et al.
9,459,235 B2 10/2016 Soundarrajan et al.
9,460,595 B2 10/2016 Chen
9,460,596 B1 10/2016 Moses
9,460,611 B2 10/2016 Emerson et al.
9,466,194 B1 10/2016 Kraz et al.
9,470,168 B2 10/2016 Yoon
9,472,070 B2 10/2016 Chen
9,472,092 B1 10/2016 Grant
9,473,559 B2 10/2016 Rezvani et al.
9,474,023 B1 10/2016 Kates
9,474,824 B2 10/2016 Conroy et al.
9,476,341 B2 10/2016 Whitt et al.
9,476,387 B2 10/2016 Kim et al.
9,476,862 B2 10/2016 Motayed et al.
9,482,124 B2 11/2016 Dong et al.
9,482,136 B2 11/2016 Ancimer et al.
9,482,137 B2 11/2016 Liu et al.
9,482,172 B2 11/2016 Pursifull et al.
9,489,807 B2 11/2016 Morris
9,489,829 B2 11/2016 Sloo et al.
9,491,224 B2 11/2016 Rezvani et al.
9,492,788 B2 11/2016 Gaudin
9,495,853 B2 11/2016 Jackson
9,499,572 B2 11/2016 Wensbo Posaric et al.
9,499,584 B2 11/2016 Paz Rojas et al.
9,500,580 B1 11/2016 Mitra et al.
9,501,452 B2 11/2016 Kowalkowski et al.
9,503,539 B1 11/2016 Trundle et al.
9,506,414 B2 11/2016 Melby et al.
9,506,649 B2 11/2016 Rennie et al.
9,506,863 B2 11/2016 Hicks et al.
9,506,901 B2 11/2016 Lewis
9,509,754 B2 11/2016 Rezvani et al.
9,513,007 B2 12/2016 Kuchta
9,513,191 B2 12/2016 Schankula et al.
9,513,210 B2 12/2016 Kharrat et al.
9,513,898 B2 12/2016 Solnit et al.
9,514,631 B2 12/2016 Matsuoka et al.
9,518,710 B2 12/2016 Li
9,518,960 B2 12/2016 Nema et al.
9,520,042 B2 12/2016 Eck
9,520,046 B2 12/2016 Call et al.
9,520,054 B2 12/2016 Rossi et al.
9,522,209 B2 12/2016 Meier et al.
9,522,210 B2 12/2016 Worrilow
9,527,498 B2 12/2016 Martin et al.
9,528,422 B2 12/2016 Li et al.
9,528,424 B2 12/2016 Aoki et al.
9,528,462 B2 12/2016 Ardanese et al.
9,528,473 B2 12/2016 Dudar et al.
9,528,476 B2 12/2016 Surnilla et al.
9,528,979 B2 12/2016 Haick et al.
9,530,305 B2 12/2016 Burnette et al.
9,534,524 B1 1/2017 Hopka et al.
9,534,553 B2 1/2017 Chamarthi et al.
9,534,984 B2 1/2017 Glugla et al.
9,537,670 B2 1/2017 Cho et al.
9,540,589 B2 1/2017 Angel et al.
9,541,040 B2 1/2017 Karunaratne et al.
9,547,968 B2 1/2017 Adams et al.
9,551,260 B2 1/2017 Kakimoto
9,551,701 B2 1/2017 Marchand et al.
9,552,705 B2 1/2017 Morris
9,552,718 B2 1/2017 Fadell et al.
9,552,720 B2 1/2017 Moffa
9,553,971 B2 1/2017 Calabrese et al.
9,556,469 B2 1/2017 Marcoux et al.
9,556,812 B2 1/2017 Ozkan
9,560,712 B2 1/2017 Chen
9,562,470 B2 2/2017 Younkins et al.
9,562,841 B2 2/2017 Tylutki et al.
9,562,882 B2 2/2017 Crunaire et al.
9,565,657 B2 2/2017 Suresh et al.
9,568,456 B2 2/2017 Yi et al.
9,568,902 B2 2/2017 Dunn et al.
9,569,945 B2 2/2017 Zumsteg et al.
9,574,480 B2 2/2017 Matsumoto et al.
9,574,763 B2 2/2017 Chen
9,574,971 B2 2/2017 McKay et al.
9,575,038 B2 2/2017 Furton et al.
9,575,042 B2 2/2017 Okrut et al.
9,576,457 B1 2/2017 Mona
9,576,458 B2 2/2017 Calvert
9,576,466 B2 2/2017 Sager et al.
9,581,098 B2 2/2017 Chen et al.
9,581,099 B1 2/2017 Szailer et al.
9,581,561 B2 2/2017 Tao et al.
9,581,574 B2 2/2017 Murphy
9,581,575 B2 2/2017 Batayneh et al.
9,588,084 B2 3/2017 Delapierre et al.
9,589,440 B2 3/2017 Pan et al.
9,589,441 B2 3/2017 Shapiro et al.
9,593,617 B2 3/2017 Veldten et al.
9,594,006 B2 3/2017 Harner
9,598,848 B2 3/2017 Seibt et al.
9,599,004 B2 3/2017 Takaoka
9,599,005 B2 3/2017 Khaled et al.
9,600,998 B2 3/2017 Mumey
9,601,001 B2 3/2017 Matsuoka et al.
9,605,578 B1 3/2017 Qi
9,606,040 B2 3/2017 Sakamoto et al.
9,606,092 B2 3/2017 Brahma
9,607,494 B2 3/2017 Pattok et al.
9,609,399 B2 3/2017 Krishnamurthy et al.
9,611,308 B2 4/2017 Matsunami et al.
9,611,813 B2 4/2017 Dudar
9,612,174 B2 4/2017 Peters et al.
9,612,602 B2 4/2017 Smith et al.
9,613,516 B2 4/2017 Glasgow et al.
9,615,066 B1 4/2017 Tran et al.
9,617,899 B2 4/2017 Goodwin
9,617,940 B2 4/2017 Klingbeil et al.
9,624,525 B2 4/2017 Fallon
9,624,804 B2 4/2017 Matsumoto et al.
9,624,808 B2 4/2017 Miyamoto et al.
9,625,112 B2 4/2017 Li
9,625,374 B2 4/2017 Chang et al.
9,625,432 B2 4/2017 Villarreal Guerra et al.
9,626,858 B2 4/2017 Sloo et al.
9,631,585 B2 4/2017 Lombardo et al.
9,633,547 B2 4/2017 Farrand et al.
9,633,551 B2 4/2017 Aljadeff et al.
9,638,122 B2 5/2017 Smith et al.
9,642,340 B2 5/2017 Brown, Jr. et al.
9,644,974 B2 5/2017 Plocher et al.
9,645,068 B2 5/2017 Zhang
9,645,126 B2 5/2017 Dufour et al.
9,645,127 B2 5/2017 Amin et al.
9,646,476 B1 5/2017 Hansen
9,648,082 B2 5/2017 Rezvani et al.
9,650,981 B1 5/2017 Large et al.
9,652,976 B2 5/2017 Bruck et al.
9,657,326 B2 5/2017 Ruether et al.
9,657,627 B2 5/2017 Kogo et al.
9,657,630 B2 5/2017 Perrin et al.
9,662,626 B2 5/2017 Yates et al.
9,664,089 B2 5/2017 Kim et al.
9,664,095 B2 5/2017 Van Nieuwstadt et al.

(56) References Cited

U.S. PATENT DOCUMENTS 9,664,569 B2 5/2017 Mittleman et al.
9,664,570 B2 5/2017 Ademe et al.
9,666,006 B2 5/2017 Kramer et al.
9,667,907 B2 5/2017 Diaz
9,670,817 B2 6/2017 Yoo et al.
9,670,861 B2 6/2017 Jankovic et al.
9,671,380 B2 6/2017 Weber et al.
9,677,327 B1 6/2017 Nagel et al.
9,677,450 B2 6/2017 Lauer et al.
9,677,452 B2 6/2017 Kogo et al.
9,677,488 B2 6/2017 Nilsson
9,677,491 B2 6/2017 Jammoussi et al.
9,678,059 B2 6/2017 Haick et al.
9,682,610 B2 * 6/2017 Duan .................... B60H 1/008
9,683,507 B2 6/2017 Yezerets et al.
9,683,535 B2 6/2017 Glugla et al.
9,685,054 B2 6/2017 Simmons
9,689,335 B2 6/2017 Ge
9,689,542 B2 6/2017 Anderson et al.
9,689,826 B2 6/2017 Haick et al.
9,689,853 B2 6/2017 Mittleman et al.
9,691,254 B2 6/2017 Jeong
9,691,256 B2 6/2017 Wu et al.
9,691,257 B2 6/2017 Matsuoka et al.
9,691,261 B2 6/2017 Tuck et al.
9,693,512 B2 7/2017 Chen et al.
9,696,291 B2 7/2017 Gailius et al.
9,696,311 B2 7/2017 Haick et al.
9,697,713 B2 7/2017 Fadell et al.
9,701,243 B1 7/2017 Phatak et al.
9,702,293 B2 7/2017 Fujie et al.
9,702,315 B1 7/2017 Palmer
9,702,566 B2 7/2017 Robison et al.
9,704,095 B2 7/2017 Jacquot et al.
9,704,380 B2 7/2017 Matsuoka et al.
9,708,952 B2 7/2017 Akiyoshi
9,708,953 B1 7/2017 Szailer et al.
9,708,960 B2 7/2017 Hall et al.
9,709,540 B2 7/2017 Lee et al.
9,709,543 B2 7/2017 Sun et al.
9,709,544 B2 7/2017 Kozlow et al.
9,710,001 B2 7/2017 Smith et al.
9,714,614 B2 7/2017 Luehrsen et al.
9,714,941 B2 7/2017 Zhang et al.
9,715,818 B2 7/2017 Poder et al.
9,717,357 B2 8/2017 Johnson et al.
9,717,815 B2 8/2017 Peterson et al.
9,719,449 B2 8/2017 Miyamoto et al.
9,721,456 B2 8/2017 Thurlow et al.
9,721,457 B2 8/2017 Thompson et al.
9,726,633 B2 8/2017 Mett et al.
9,728,082 B2 8/2017 Fox
9,729,945 B2 8/2017 Schultz et al.
9,732,690 B2 8/2017 Rollinger et al.
9,733,155 B2 8/2017 Monros
9,733,225 B2 8/2017 Armstrong
9,737,627 B2 8/2017 Turner et al.
9,739,248 B2 8/2017 Dudar et al.
9,739,709 B2 8/2017 Lear et al.
9,739,761 B2 8/2017 Smith et al.
9,740,822 B2 8/2017 Jackson
9,746,154 B2 8/2017 Dong et al.
9,746,439 B2 8/2017 Porro et al.
9,747,637 B1 8/2017 Kalaboukis et al.
9,747,763 B1 8/2017 Scordato et al.
9,752,488 B2 9/2017 Zambrano et al.
9,752,740 B1 9/2017 Li
9,752,785 B2 9/2017 Corleoni
9,754,466 B2 9/2017 Simmons
9,756,169 B2 9/2017 Mehta et al.
9,758,016 B1 9/2017 Baron et al.
9,759,688 B2 9/2017 Naishadham et al.
9,760,853 B2 9/2017 Rose
9,761,096 B2 9/2017 McMahan et al.
9,761,124 B2 9/2017 Matsuoka et al.
9,763,426 B2 9/2017 Pearce et al.
9,764,623 B2 9/2017 Fruehsorger et al.
9,764,893 B1 9/2017 Westmoreland, III
9,765,668 B2 9/2017 Maus et al.
9,765,715 B2 9/2017 Hohner et al.
9,766,215 B2 9/2017 Hassan et al.
9,767,674 B2 9/2017 Matsuoka et al.
9,767,679 B2 9/2017 Piccolo, III et al.
9,769,420 B1 9/2017 Moses
9,776,725 B2 10/2017 Fox et al.
9,777,659 B2 10/2017 Aoyagi
9,777,697 B2 10/2017 Glugla et al.
9,778,173 B2 10/2017 Chang et al.
9,779,615 B2 10/2017 Davell et al.
9,782,744 B2 10/2017 Warner et al.
9,784,166 B2 10/2017 Osburn et al.
9,784,701 B2 10/2017 Wensbo Posaric et al.
9,784,721 B2 10/2017 Yacoub
9,786,158 B2 10/2017 Beaver et al.
9,790,878 B2 10/2017 Kumar et al.
9,791,425 B2 10/2017 Stollings
9,792,794 B2 10/2017 Morris
9,792,795 B2 10/2017 Warmack et al.
9,796,371 B2 10/2017 Soifer
9,797,344 B2 10/2017 Jeffrey
9,798,309 B2 10/2017 Tirpak
9,798,979 B2 10/2017 Fadell et al.
9,799,175 B2 10/2017 Stagg
9,803,909 B2 10/2017 Son et al.
9,808,021 B2 11/2017 Johnson et al.
9,808,812 B2 11/2017 Gruenbacher et al.
9,810,674 B2 11/2017 Mikami et al.
9,811,994 B1 11/2017 Salzer
9,812,001 B1 11/2017 Grant
9,816,415 B2 11/2017 Hokuto
9,817,492 B2 11/2017 Park
9,819,910 B2 11/2017 Huang et al.
9,819,911 B2 11/2017 K V et al.
9,821,082 B1 11/2017 Swartz et al.
9,823,236 B2 11/2017 Hao et al.
9,824,399 B2 11/2017 Bernard et al.
9,824,565 B1 11/2017 Patel
9,827,342 B2 11/2017 Morgan et al.
9,827,343 B2 11/2017 Lima et al.
9,829,473 B2 11/2017 Arias Espinoza et al.
9,830,790 B2 11/2017 Jones
9,830,804 B2 11/2017 Kreiner et al.
9,835,064 B2 12/2017 Cassani et al.
9,835,104 B2 12/2017 Okazaki et al.
9,835,602 B2 12/2017 Brasfield
9,836,953 B2 12/2017 Fadell et al.
9,841,400 B2 12/2017 Vingerhoets et al.
9,842,479 B1 12/2017 Black
9,844,339 B2 12/2017 Wang et al.
9,845,503 B2 12/2017 Swartz
9,846,110 B2 12/2017 Tylutki et al.
9,850,840 B2 12/2017 Miyamoto et al.
9,854,641 B2 12/2017 Chen
9,855,820 B2 1/2018 Baron, Jr. et al.
9,857,299 B2 1/2018 Lear et al.
9,858,784 B2 1/2018 Peeters et al.
9,858,794 B2 1/2018 McCleary et al.
9,860,839 B2 1/2018 Kates
9,861,126 B2 1/2018 Utley et al.
9,862,985 B2 1/2018 Lim et al.
9,863,354 B2 1/2018 Okazaki et al.
9,863,375 B2 1/2018 Takakura et al.
9,863,641 B2 1/2018 Boyd
9,863,656 B2 1/2018 Amerson
9,863,923 B2 1/2018 Abbott et al.
9,865,157 B2 1/2018 Hayek
9,870,696 B2 1/2018 Aich et al.
9,874,167 B2 1/2018 MacEwen et al.
9,874,171 B2 1/2018 Bleile et al.
9,874,334 B2 1/2018 Chen
9,875,631 B2 1/2018 Mittleman et al.
9,877,507 B2 1/2018 Xiang
9,877,519 B2 1/2018 Xiang
9,879,580 B2 1/2018 Gupta et al.

(56) References Cited

U.S. PATENT DOCUMENTS 9,879,587 B2 1/2018 Kim et al.
9,879,628 B2 1/2018 Nishijima et al.
9,879,630 B2 1/2018 Guo et al.
9,880,083 B2 1/2018 Gaertner et al.
9,880,138 B1 1/2018 Hall et al.
9,881,130 B2 1/2018 Jackson
9,881,470 B2 1/2018 Baynes et al.
9,883,001 B2 1/2018 Verna et al.
9,884,269 B2 2/2018 Hunter et al.
9,890,678 B2 2/2018 Qi
9,890,685 B2 2/2018 Jang
9,890,969 B2 2/2018 Martin
9,891,139 B2 2/2018 Nakasone et al.
9,892,456 B1 2/2018 Kalaboukis et al.
9,892,615 B2 2/2018 Glasgow et al.
9,896,989 B2 2/2018 Kakimoto
9,897,028 B2 2/2018 Miyamoto et al.
9,897,592 B2 2/2018 Ray et al.
9,898,916 B2 2/2018 Valleru
9,903,292 B2 2/2018 Miyamoto et al.
9,903,634 B2 2/2018 Son et al.
9,903,846 B2 2/2018 Bright
9,905,122 B2 2/2018 Sloo et al.
9,909,473 B2 3/2018 Martin et al.
9,909,480 B2 3/2018 Mitchell et al.
9,909,482 B2 3/2018 Ardanese et al.
9,909,540 B2 3/2018 Heinrich et al.
9,909,541 B1 3/2018 Bevan et al.
9,913,124 B2 3/2018 Liu
9,914,341 B2 3/2018 Ono et al.
9,914,760 B2 3/2018 Pfister et al.
9,920,944 B2 3/2018 Chromy et al.
9,922,513 B1 3/2018 Hall et al.
9,922,517 B2 3/2018 Adams et al.
9,922,530 B2 3/2018 Wu et al.
9,927,413 B2 3/2018 Gong et al.
9,928,672 B2 3/2018 Jablokov et al.
9,929,494 B2 3/2018 Schmidt et al.
9,932,938 B2 4/2018 Surnilla et al.
9,939,307 B2 4/2018 Hall et al.
9,939,348 B2 4/2018 Nakasone et al.
9,939,412 B2 4/2018 Ichimura et al.
9,940,805 B1 4/2018 Mona
9,940,820 B2 4/2018 Watkins et al.
9,943,563 B2 4/2018 Wilson
9,943,806 B2 4/2018 Minezawa et al.
9,945,312 B2 4/2018 Tanaka
9,945,573 B2 4/2018 Balkhair
9,953,513 B2 4/2018 Chua
9,955,242 B1 4/2018 Manzella et al.
9,955,423 B2 4/2018 Kates
9,955,728 B2 5/2018 Liu
9,955,898 B2 5/2018 Ra et al.
9,957,872 B2 5/2018 Aoyama et al.
9,957,924 B2 5/2018 Dudar
9,958,168 B2 5/2018 Robison et al.
9,959,717 B2 5/2018 Thornton et al.
9,959,735 B2 5/2018 Patil et al.
9,964,530 B2 5/2018 Baldaccini
9,964,973 B2 5/2018 Smith et al.
9,970,372 B2 5/2018 Kumar et al.
9,970,916 B2 5/2018 Singer et al.
9,976,503 B2 5/2018 Surnilla et al.
9,976,521 B1 5/2018 Jentz et al.
9,976,717 B2 5/2018 Li
9,978,251 B2 5/2018 Gonia et al.
9,982,471 B2 5/2018 Ozkan
9,983,011 B2 5/2018 Mountain
9,983,124 B2 5/2018 Wang et al.
9,983,182 B2 5/2018 Chen et al.
9,983,183 B2 5/2018 Motayed et al.
9,984,555 B2 5/2018 Bieser
9,988,963 B2 6/2018 Maertens et al.
9,989,003 B2 6/2018 Karunaratne
9,989,018 B2 6/2018 Dudar
9,989,474 B2 6/2018 Song et al.
9,989,507 B2 6/2018 Benn
9,990,841 B2 6/2018 Moffa
9,994,569 B2 6/2018 George et al.
9,995,653 B2 6/2018 Stojicevic et al.
9,995,674 B2 6/2018 Prasad
9,997,046 B2 6/2018 Bermudez Rodriguez et al.
9,997,057 B2 6/2018 Pimentel
9,997,058 B2 6/2018 Sloo et al.
9,998,899 B1 6/2018 Tannenbaum
10,001,045 B2 6/2018 Kumar et al.
10,006,896 B2 6/2018 Fernstrom et al.
10,011,481 B2 7/2018 Haick
10,012,169 B2 7/2018 Rueger et al.
10,013,872 B1 7/2018 Seigler et al.
10,015,743 B2 7/2018 Kates
10,018,091 B2 7/2018 Hendrickson et al.
10,018,158 B2 7/2018 Dudar
10,026,304 B2 7/2018 Taylor et al.
10,031,125 B2 7/2018 Koo et al.
10,031,126 B2 7/2018 Blake et al.
10,032,363 B2 7/2018 Bruck et al.
10,034,979 B2 7/2018 Bechtel et al.
10,035,837 B2 7/2018 Zhang et al.
10,036,297 B2 7/2018 Khaled et al.
10,041,427 B2 8/2018 Hanawa et al.
10,041,908 B2 8/2018 Kim et al.
10,041,916 B2 8/2018 Michalske
10,041,917 B2 8/2018 Bardoni
10,041,935 B2 8/2018 Rinberg et al.
10,043,593 B2 8/2018 Jackson
10,046,262 B2 8/2018 Buckner
10,047,971 B2 8/2018 Nyamjav et al.
10,048,243 B2 8/2018 Yamamoto
10,052,045 B2 8/2018 Hao et al.
10,053,650 B2 8/2018 Angel et al.
10,054,070 B2 8/2018 Dudar et al.
10,054,096 B2 8/2018 Berkson
10,054,499 B2 8/2018 Karunaratne et al.
10,055,803 B2 8/2018 Orduna et al.
10,058,627 B2 8/2018 Kelsen
10,060,111 B2 8/2018 Hall et al.
10,060,259 B2 8/2018 McAlary et al.
10,060,346 B2 8/2018 Pfister et al.
10,060,829 B2 8/2018 Hanawa et al.
10,060,894 B2 8/2018 Michalske
10,062,261 B2 8/2018 Shaffer
10,063,814 B2 8/2018 Wood et al.
10,066,114 B2 9/2018 Jackson et al.
10,066,533 B2 9/2018 Kogo et al.
10,066,567 B2 9/2018 Kato
10,067,108 B2 9/2018 King-Smith et al.
10,072,542 B2 9/2018 Fujii et al.
10,078,054 B2 9/2018 Heywood et al.
10,087,395 B2 10/2018 Pelzer et al.
10,089,848 B2 10/2018 Albinger et al.
10,092,671 B2 10/2018 Duong et al.
10,094,264 B2 10/2018 Khaled et al.
10,094,310 B2 10/2018 Ulrey et al.
10,094,312 B2 10/2018 Brennan et al.
10,094,725 B2 10/2018 Reinmuth et al.
10,094,803 B2 10/2018 Reinhardt et al.
10,100,695 B2 10/2018 Anilovich et al.
10,100,698 B2 10/2018 Minezawa et al.
10,100,770 B2 10/2018 Dudar
10,100,782 B2 10/2018 Lucka et al.
10,101,291 B2 10/2018 Ho
10,101,298 B1 10/2018 Zhang et al.
10,101,314 B2 10/2018 Endou
10,101,319 B2 10/2018 Trowell et al.
10,102,728 B1 10/2018 Bajaj et al.
10,103,811 B2 10/2018 Stout et al.
10,107,233 B2 10/2018 Dudar et al.
10,107,665 B2 10/2018 Hall et al.
10,107,827 B1 10/2018 Agarwal et al.
10,109,176 B2 10/2018 Wright et al.
10,110,857 B2 10/2018 Qu et al.
10,113,953 B2 10/2018 Babin et al.
10,115,287 B2 10/2018 Rostami

(56) References Cited

U.S. PATENT DOCUMENTS 10,118,119 B2 11/2018 Sappok et al.
10,118,608 B1 11/2018 Dudar
10,119,448 B2 11/2018 Kidokoro et al.
10,119,489 B2 11/2018 Hasegawa et al.
10,119,847 B2 11/2018 Heffernan
10,120,105 B2 11/2018 Haupt et al.
10,121,075 B2 11/2018 Du et al.
10,122,784 B2 11/2018 Rezvani et al.
10,123,509 B2 11/2018 Pearce et al.
10,125,656 B2 11/2018 Monna et al.
10,125,657 B2 11/2018 Monna et al.
10,131,955 B2 11/2018 Darling et al.
10,132,250 B2 11/2018 Zhong et al.
10,132,727 B2 11/2018 Remondini
10,134,247 B2 11/2018 McMahan et al.
10,137,770 B2 11/2018 Yamashita et al.
10,138,827 B2 11/2018 Dudar
10,138,830 B1 11/2018 Glugla
10,138,846 B1 11/2018 Dudar
10,140,849 B2 11/2018 Sloo et al.
10,142,421 B2 11/2018 Mighdoll et al.
10,143,608 B2 12/2018 Kostic
10,145,285 B2 12/2018 Maillard
10,150,365 B2 12/2018 Dudar et al.
10,151,262 B2 12/2018 Miyamoto et al.
10,151,265 B2 12/2018 Dudar
10,152,866 B2 12/2018 Kraz et al.
10,156,176 B2 12/2018 Osburn et al.
10,156,200 B2 12/2018 Miyamoto
10,156,213 B2 12/2018 Pursifull et al.
10,161,284 B2 12/2018 Cunningham et al.
10,161,326 B2 12/2018 Glugla et al.
10,161,341 B2 12/2018 Taibi et al.
10,161,845 B2 12/2018 Bovi
10,161,896 B2 12/2018 Gryska et al.
10,161,920 B2 12/2018 Hassan et al.
10,167,823 B2 1/2019 Dudar
10,168,315 B2 1/2019 Haick et al.
10,168,331 B2 1/2019 Ruddock et al.
10,169,962 B1 1/2019 Walker et al.
10,176,705 B1 1/2019 Grant
10,176,706 B2 1/2019 Beaver et al.
10,176,805 B2 1/2019 Carlin et al.
10,179,184 B2 1/2019 Belz et al.
10,180,101 B1 1/2019 Park et al.
10,180,112 B2 1/2019 Hayashita et al.
10,180,673 B2 1/2019 Sinha et al.
10,184,382 B2 1/2019 Hagiwara et al.
10,184,913 B2 1/2019 Aoki et al.
10,186,331 B2 1/2019 Jackson
10,188,767 B2 1/2019 Okada et al.
10,190,413 B2 1/2019 Smith
10,191,004 B2 1/2019 Koley et al.
10,191,008 B2 1/2019 Chapples et al.
10,192,426 B2 1/2019 Nold
10,196,958 B2 2/2019 Nakasone et al.
10,197,000 B1 2/2019 Dudar
10,197,243 B2 2/2019 Dong et al.
10,197,532 B1 2/2019 Manginell et al.
10,202,915 B2 2/2019 Mueller et al.
10,209,213 B2 2/2019 Kang et al.
10,210,745 B2 2/2019 Tung et al.
10,213,038 B2 2/2019 Wei et al.
10,217,090 B2 2/2019 Warren et al.
10,217,344 B2 2/2019 Gage et al.
10,221,746 B2 3/2019 Kidokoro et al.
10,223,844 B1 3/2019 Schwie et al.
10,223,889 B2 3/2019 Park et al.
10,226,472 B2 3/2019 Goodenow et al.
10,227,628 B2 3/2019 Moularat et al.
10,227,629 B2 3/2019 Koo et al.
10,228,704 B2 3/2019 Cohen et al.
10,229,583 B2 3/2019 Matsuoka et al.
10,229,584 B2 3/2019 Davell et al.
10,232,296 B2 3/2019 Takaoka et al.
10,232,771 B2 3/2019 Zehr
10,233,856 B2 3/2019 Dudar
10,234,388 B2 3/2019 Ebata et al.
10,234,418 B2 3/2019 Nakata et al.
10,234,420 B2 3/2019 Kayama et al.
10,234,437 B2 3/2019 Bright
10,237,237 B2 3/2019 Dawes et al.
10,237,358 B2 3/2019 Haupt et al.
10,238,149 B2 3/2019 Hon
10,240,484 B2 3/2019 Zhang et al.
10,240,502 B2 3/2019 De Smet et al.
10,241,078 B2 3/2019 Mohanty et al.
10,241,105 B2 3/2019 Kwak et al.
10,242,550 B2 3/2019 Glasgow et al.
10,247,114 B2 4/2019 Nakamura et al.
10,247,714 B2 4/2019 Stokes
10,253,716 B2 4/2019 Mentele
10,253,728 B2 4/2019 Dudar et al.
10,254,199 B2 4/2019 Pilon
10,254,260 B2 4/2019 Amin et al.
10,254,261 B2 4/2019 Le Neel et al.
10,255,800 B2 4/2019 Fox
10,258,295 B2 4/2019 Fountaine
10,259,927 B2 4/2019 Bercx et al.
10,261,071 B2 4/2019 Hall et al.
10,262,507 B2 4/2019 Sloo et al.
10,262,508 B2 4/2019 Fadell et al.
10,262,525 B2 4/2019 Carlin et al.
10,267,778 B2 4/2019 Gong et al.
10,271,738 B2 4/2019 Peeters
10,274,390 B2 4/2019 Sieber et al.
10,274,467 B2 4/2019 Kim et al.
10,274,469 B2 4/2019 Brasfield
10,274,470 B2 4/2019 Hunter
10,276,018 B2 4/2019 Brillaud
10,276,022 B2 4/2019 Goodson
10,280,682 B1 5/2019 Nagel et al.
10,280,821 B2 5/2019 Crawford et al.
10,280,863 B2 5/2019 Dudar
10,281,167 B2 5/2019 Martin
10,281,364 B1 5/2019 Kallhoff et al.
10,282,960 B2 5/2019 Verna et al.
10,282,975 B2 5/2019 King et al.
10,288,277 B2 5/2019 Chen
10,288,592 B2 5/2019 Takaoka et al.
10,294,252 B2 5/2019 Braddock-Wilking et al.
10,295,457 B1 5/2019 Ocheltree
10,295,515 B2 5/2019 Shao et al.
10,301,991 B1 5/2019 Dudar
10,302,321 B2 5/2019 Sakai et al.
10,304,319 B2 5/2019 Sager et al.
10,306,922 B2 6/2019 Utley et al.
10,309,942 B2 6/2019 Yoo
10,309,944 B2 6/2019 Hopka et al.
10,309,953 B2 6/2019 Sappok et al.
10,314,251 B2 6/2019 Gagne et al.
10,316,767 B2 6/2019 Park
10,316,770 B2 6/2019 Veldten et al.
10,316,779 B2 6/2019 Miyamoto et al.
10,319,207 B1 6/2019 Janscha et al.
10,323,562 B2 6/2019 Van Nieuwstadt et al.
10,329,982 B2 6/2019 Smith et al.
10,329,986 B2 6/2019 Wang et al.
10,330,051 B2 6/2019 Dudar et al.
10,330,617 B2 6/2019 Hur et al.
10,332,383 B1 6/2019 Giles
10,337,377 B2 7/2019 Latrofa et al.
10,337,384 B2 7/2019 Martin et al.
10,337,422 B2 7/2019 Hosoya et al.
10,338,026 B2 7/2019 Reinhardt et al.
10,338,046 B2 7/2019 Ando et al.
10,339,791 B2 7/2019 Baum et al.
10,344,313 B2 7/2019 Moularat et al.
10,345,016 B2 7/2019 Garing et al.
10,348,575 B2 7/2019 Sundermeyer et al.
10,351,796 B2 7/2019 Sturgis et al.
10,352,223 B2 7/2019 York et al.
10,352,225 B2 7/2019 Takita et al.
10,354,351 B2 7/2019 Orduna et al.

(56) References Cited

U.S. PATENT DOCUMENTS 10,357,587 B2 7/2019 Li
10,358,994 B1 7/2019 Dudar
10,363,514 B2 7/2019 Kelly et al.
10,364,717 B2 7/2019 Kubinski
10,364,926 B2 7/2019 Taft et al.
10,365,183 B2 7/2019 Miyamoto et al.
10,365,260 B2 7/2019 Amaravadi
10,365,810 B2 7/2019 Sundermeyer et al.
10,366,588 B2 7/2019 Slavin et al.
10,366,590 B2 7/2019 Bajaj et al.
10,369,509 B2 8/2019 Vo
10,371,600 B2 8/2019 Varney
10,371,677 B2 8/2019 Nakada et al.
10,373,472 B2 8/2019 Johnston
10,378,404 B2 8/2019 De Smet et al.
10,378,415 B2 8/2019 Cole et al.
10,378,472 B2 8/2019 Dudar et al.
10,379,072 B2 8/2019 Blease et al.
10,379,092 B2 8/2019 Gafsou
10,379,093 B2 8/2019 Murphy et al.
10,379,096 B2 8/2019 Wang et al.
10,380,875 B1 8/2019 Roberts et al.
10,383,174 B2 8/2019 Louveau et al.
10,385,752 B2 8/2019 Matsumoto et al.
10,385,753 B2 8/2019 Nobukawa et al.
10,386,325 B2 8/2019 Xiao et al.
10,386,348 B2 8/2019 Kim et al.
10,386,349 B2 8/2019 Zaripov et al.
10,391,193 B2 8/2019 Peterson et al.
10,393,713 B2 8/2019 Lemire et al.
10,393,763 B2 8/2019 Kita et al.
10,400,654 B2 9/2019 Wiebenga et al.
10,401,336 B2 9/2019 Spartz et al.
10,401,340 B2 9/2019 Soundarrajan et al.
10,405,072 B1 9/2019 Manzella et al.
10,408,111 B2 9/2019 Hall et al.
10,408,114 B2 9/2019 Rollinger et al.
10,408,143 B2 9/2019 Dudar
10,408,154 B2 9/2019 Dudar
10,408,158 B2 9/2019 Klingbeil
10,408,471 B1 9/2019 Lanouette
10,408,809 B1 9/2019 Emanuel et al.
10,412,985 B2 9/2019 Byron et al.
10,416,138 B2 9/2019 Byron et al.
10,416,142 B2 9/2019 Mazzillo et al.
10,417,899 B2 9/2019 Kim
10,422,292 B2 9/2019 Glugla
10,422,771 B2 9/2019 Kuroki et al.
10,424,412 B2 9/2019 Huang
10,428,717 B2 10/2019 Monna et al.
10,429,330 B2 10/2019 Le Neel et al.
10,429,335 B2 10/2019 Porro et al.
10,429,367 B2 10/2019 Crescini et al.
10,431,055 B2 10/2019 Palmer et al.
10,431,060 B2 10/2019 Saidi
10,436,138 B2 10/2019 Dudar
10,438,457 B2 10/2019 Kramer et al.
10,438,472 B2 10/2019 Haynes et al.
10,441,178 B2 10/2019 Campo et al.
10,443,471 B2 10/2019 Funk et al.
10,443,517 B2 10/2019 Glugla
10,444,123 B2 10/2019 Koo et al.
10,450,733 B2 10/2019 Luettgen et al.
10,450,932 B2 10/2019 Tsutsumi
10,450,933 B2 10/2019 Quigley et al.
10,450,983 B2 10/2019 Glugla et al.
10,450,985 B2 10/2019 Nagar et al.
10,451,010 B2 10/2019 Dudar
10,453,321 B2 10/2019 Adams et al.
10,455,395 B2 10/2019 Gharabegian
10,455,817 B2 10/2019 Hall et al.
10,457,200 B2 10/2019 Gage et al.
10,458,306 B2 10/2019 Takaoka et al.
10,458,372 B2 10/2019 Michalske et al.
10,458,627 B2 10/2019 Perez-Bolivar et al.
10,459,227 B2 10/2019 Norrell
10,462,876 B2 10/2019 Nicholas et al.
10,465,961 B2 11/2019 Kujak
10,467,879 B2 11/2019 Stefanski et al.
10,467,885 B2 11/2019 Trundle et al.
10,467,887 B2 11/2019 Herman et al.
10,471,804 B1 11/2019 Wengreen et al.
10,473,635 B2 11/2019 Wang
10,475,318 B2 11/2019 Peeters et al.
10,475,319 B2 11/2019 Janscha et al.
10,476,294 B2 11/2019 Wang et al.
10,479,213 B2 11/2019 Lee et al.
10,480,368 B2 11/2019 Santillo et al.
10,480,375 B2 11/2019 Khaled
10,480,384 B2 11/2019 Khaled et al.
10,482,698 B2 11/2019 Caterino et al.
10,482,759 B2 11/2019 Sayavong et al.
10,487,782 B2 11/2019 Bevan et al.
10,488,064 B1 11/2019 Crowder et al.
10,488,315 B2 11/2019 Weber et al.
10,488,837 B2 11/2019 Cirino
10,492,967 B2 12/2019 Kostic
10,494,972 B2 12/2019 Collins et al.
10,494,976 B2 12/2019 Qi et al.
10,502,723 B2 12/2019 Cai et al.
10,508,582 B2 12/2019 Hall et al.
10,508,822 B1 12/2019 Sheikh et al.
10,508,984 B2 12/2019 Alessi et al.
10,509,377 B2 12/2019 Willette et al.
10,511,404 B2 12/2019 Trundle et al.
10,513,961 B2 12/2019 Yoo et al.
10,513,997 B2 12/2019 Dudar
10,514,368 B2 12/2019 Sugar
10,517,329 B2 12/2019 Batista
10,517,530 B2 12/2019 Cohen
10,519,841 B2 12/2019 Bokelund et al.
10,520,203 B2 12/2019 O'Hayer
10,520,465 B2 12/2019 Perry et al.
10,522,026 B2 12/2019 Sundermeyer et al.
10,526,942 B2 1/2020 Higashiyama
10,527,305 B2 1/2020 Lin et al.
10,529,195 B2 1/2020 Sloo et al.
10,529,196 B2 1/2020 Sloo et al.
10,529,223 B2 1/2020 Kalagani et al.
10,533,930 B2 1/2020 Chrin
10,533,964 B2 1/2020 Snelders et al.
10,537,135 B2 1/2020 Smith et al.
10,537,653 B2 1/2020 Kelsen
10,539,060 B2 1/2020 Moos et al.
10,539,087 B2 1/2020 Brahma et al.
10,539,088 B2 1/2020 Rausing et al.
10,540,864 B2 1/2020 Sloo et al.
10,540,871 B2 1/2020 Wedig et al.
10,544,743 B2 1/2020 Lundstrom
10,545,072 B2 1/2020 Monna et al.
10,545,120 B2 1/2020 Meck et al.
10,546,469 B2 1/2020 Peterson et al.
10,550,749 B2 2/2020 Guo
11,214,119 B2 * 1/2022 MacNeille ......... B60H 1/00771
11,636,870 B2 * 4/2023 Varughese .............. G10L 15/22
704/251
2001/0017056 A1 8/2001 Nakagawa et al.
2001/0042371 A1 11/2001 Topfer-Hartung et al.
2001/0045895 A1 11/2001 Ellis et al.
2002/0010090 A1 1/2002 Ono
2002/0011069 A1 1/2002 Maus et al.
2002/0023430 A1 2/2002 Takaku et al.
2002/0041860 A1 4/2002 Requejo
2002/0074000 A1 6/2002 Benda
2002/0114744 A1 8/2002 Chiao et al.
2002/0120386 A1 8/2002 Shi et al.
2002/0129599 A1 9/2002 Nakagawa et al.
2002/0146361 A1 10/2002 Gardner et al.
2002/0155622 A1 10/2002 Slater et al.
2002/0157483 A1 10/2002 Lo et al.
2002/0177168 A1 11/2002 Ikematsu
2002/0182739 A1 12/2002 Sadik et al.
2002/0183001 A1 12/2002 Holter et al.
2002/0193554 A1 12/2002 Hirata et al.

(56) References Cited

U.S. PATENT DOCUMENTS

2003/0000207 A1 1/2003 Nakagawa et al.
2003/0012696 A1 1/2003 Millancourt
2003/0017618 A1 1/2003 Ikematsu
2003/0020618 A1 1/2003 Hemmer et al.
2003/0090374 A1 5/2003 Quigley
2003/0106367 A1 6/2003 Osaki et al.
2003/0106368 A1 6/2003 Osaki et al.
2003/0116711 A1 6/2003 Hara et al.
2003/0127105 A1 7/2003 Fontana
2003/0129757 A1 7/2003 Rohleder
2003/0129936 A1 7/2003 Shaikh
2003/0153088 A1 8/2003 DiMeo et al.
2003/0157006 A1 8/2003 Hei et al.
2003/0164024 A1 9/2003 Mitsubayashi et al.
2003/0165879 A1 9/2003 Woods et al.
2003/0170904 A1 9/2003 Hibbert et al.
2003/0171090 A1 9/2003 Shaikh
2003/0186641 A1 10/2003 Shaikh
2003/0192305 A1 10/2003 Iihoshi et al.
2003/0198572 A1 10/2003 Carnahan
2003/0206834 A1 11/2003 Chiao et al.
2003/0214394 A1 11/2003 Behrendsen
2003/0223068 A1 12/2003 DiFoggio et al.
2004/0002160 A1 1/2004 Shih et al.
2004/0006435 A1 1/2004 Blumenthal et al.
2004/0009605 A1 1/2004 Brown et al.
2004/0016287 A1 1/2004 Fu
2004/0028967 A1 2/2004 Katsuki et al.
2004/0032335 A1 2/2004 Parrish
2004/0033067 A1 2/2004 He et al.
2004/0050137 A1 3/2004 Hoppenworth
2004/0050188 A1 3/2004 Richards et al.
2004/0052683 A1 3/2004 Fudali et al.
2004/0054921 A1 3/2004 Land
2004/0077424 A1 4/2004 Murphy et al.
2004/0081582 A1 4/2004 Brooke
2004/0099233 A1 5/2004 Fujimoto et al.
2004/0110299 A1 6/2004 Sivavec
2004/0115319 A1 6/2004 Morris et al.
2004/0115818 A1 6/2004 Puri et al.
2004/0124989 A1 7/2004 Bachinski et al.
2004/0126888 A1 7/2004 Puri
2004/0133453 A1 7/2004 Jomini et al.
2004/0141919 A1 7/2004 Robertson
2004/0145466 A1 7/2004 Anthony et al.
2004/0146435 A1 7/2004 Goldstein et al.
2004/0149007 A1 8/2004 Staphanos
2004/0156742 A1 8/2004 Milan et al.
2004/0160329 A1 8/2004 Flanc
2004/0179970 A1 9/2004 Matsubara et al.
2004/0189982 A1 9/2004 Galarneau et al.
2004/0196465 A1 10/2004 Arnold et al.
2004/0197919 A1 10/2004 Herman et al.
2004/0203379 A1 10/2004 Witkowski et al.
2004/0235430 A1 11/2004 Ma et al.
2004/0238378 A1 12/2004 Kumazawa et al.
2004/0260454 A1 12/2004 Basir
2005/0024493 A1 2/2005 Nam
2005/0029102 A1 2/2005 Breuer et al.
2005/0042214 A1 2/2005 Gershwin et al.
2005/0045734 A1 3/2005 Peng et al.
2005/0054942 A1 3/2005 Melker et al.
2005/0056002 A1 3/2005 Nakagawa et al.
2005/0069304 A1 3/2005 He et al.
2005/0069307 A1 3/2005 He et al.
2005/0075552 A1 4/2005 Schmidt et al.
2005/0081601 A1 4/2005 Lawson
2005/0092914 A1 5/2005 Miller et al.
2005/0100478 A1 5/2005 Harvey
2005/0102998 A1 5/2005 van Nieuwstadt et al.
2005/0106741 A1 5/2005 Dijke
2005/0129654 A1 6/2005 Myers
2005/0142966 A1 6/2005 Quincy et al.
2005/0147963 A1 7/2005 Su et al.
2005/0155366 A1 7/2005 Kim et al.
2005/0160789 A1 7/2005 Freyer et al.
2005/0179541 A1 8/2005 Wolfe
2005/0188680 A1 9/2005 Ueda et al.
2005/0194460 A1 9/2005 Selander
2005/0195366 A1 9/2005 Selander et al.
2005/0199041 A1 9/2005 Weber et al.
2005/0199245 A1 9/2005 Brennan
2005/0214950 A1 9/2005 Roeder et al.
2005/0233063 A1 10/2005 Weiler et al.
2005/0233459 A1 10/2005 Melker et al.
2005/0240092 A1 10/2005 Shah et al.
2005/0241297 A1 11/2005 Wang et al.
2005/0242948 A1 11/2005 Tarr
2005/0242968 A1 11/2005 Reid
2005/0247105 A1 11/2005 Dikken et al.
2005/0252197 A1 11/2005 Nieuwstadt et al.
2005/0253709 A1 11/2005 Baker
2005/0257540 A1 11/2005 Choi et al.
2005/0262943 A1 12/2005 Claydon et al.
2005/0263394 A1 12/2005 Lewis et al.
2005/0274390 A1 12/2005 Banerjee et al.
2005/0284158 A1 12/2005 Lee et al.
2006/0000259 A1 1/2006 Rothschild et al.
2006/0000971 A1 1/2006 Jones et al.
2006/0001741 A1 1/2006 Hsu et al.
2006/0005710 A1 1/2006 Uegaki et al.
2006/0015599 A1 1/2006 Li et al.
2006/0024839 A1 2/2006 Petropavlovskikh et al.
2006/0044133 A1 3/2006 Lou
2006/0045849 A1 3/2006 Taghizadeh
2006/0049048 A1 3/2006 Kondo et al.
2006/0059895 A1 3/2006 Pott
2006/0085831 A1 4/2006 Jones et al.
2006/0101808 A1 5/2006 Nakagawa et al.
2006/0108739 A1 5/2006 Lutz
2006/0109136 A1 5/2006 Sumlin et al.
2006/0116811 A1 6/2006 Willard
2006/0117362 A1 6/2006 Jones et al.
2006/0130663 A1 6/2006 Joshi et al.
2006/0146126 A1 7/2006 Guo
2006/0154784 A1 7/2006 Surnilla et al.
2006/0155439 A1 7/2006 Slawinski et al.
2006/0171845 A1 8/2006 Martin et al.
2006/0183243 A1 8/2006 Rohleder
2006/0191319 A1 8/2006 Kurup
2006/0196167 A1 9/2006 Odajima et al.
2006/0199271 A1 9/2006 Lian et al.
2006/0199513 A1 9/2006 Choi et al.
2006/0210442 A1 9/2006 Shibata
2006/0211119 A1 9/2006 Herman et al.
2006/0218895 A1 10/2006 Wickert
2006/0226972 A1 10/2006 Smith
2006/0229009 A1 10/2006 Illing et al.
2006/0237333 A1 10/2006 Planje
2006/0246592 A1 11/2006 Hashmonay
2006/0250236 A1 11/2006 Ackley et al.
2006/0254004 A1 11/2006 Fraenkel
2006/0255931 A1 11/2006 Hartsfield et al.
2006/0258215 A1 11/2006 Lai et al.
2006/0260295 A1 11/2006 Gielen
2006/0263892 A1 11/2006 Withbroe et al.
2006/0272704 A1 12/2006 Fima
2007/0003980 A1 1/2007 Woods et al.
2007/0008099 A1 1/2007 Kimmel et al.
2007/0008104 A1 1/2007 McBain
2007/0017212 A1 1/2007 Yamauchi et al.
2007/0023540 A1 2/2007 Selander
2007/0024455 A1 2/2007 Morris
2007/0028596 A1 2/2007 Takaku et al.
2007/0041865 A1 2/2007 Ayoub et al.
2007/0044457 A1 3/2007 Upadhyay et al.
2007/0049259 A1 3/2007 Onishi et al.
2007/0050095 A1 3/2007 Nelson et al.
2007/0052533 A1 3/2007 Glazer
2007/0053787 A1 3/2007 Roberts et al.
2007/0066215 A1 3/2007 Song et al.
2007/0069882 A1 3/2007 Mahajan
2007/0075844 A1 4/2007 Taylor
2007/0080021 A1 4/2007 Collins

(56) References Cited

U.S. PATENT DOCUMENTS

2007/0084196 A1 4/2007 Surnilla et al.
2007/0085692 A1 4/2007 Grant et al.
2007/0088472 A1 4/2007 Ganzhorn et al.
2007/0095050 A1 5/2007 Asano
2007/0101867 A1 5/2007 Hunter et al.
2007/0103329 A1 5/2007 Lin
2007/0105494 A1 5/2007 Lin
2007/0111655 A1 5/2007 Song et al.
2007/0116607 A1 5/2007 Wang et al.
2007/0120978 A1 5/2007 Jones et al.
2007/0131566 A1 6/2007 Filanovsky et al.
2007/0134133 A1 6/2007 Wenzhi et al.
2007/0134196 A1 6/2007 Park et al.
2007/0137181 A1 6/2007 Upadhyay et al.
2007/0144143 A1 6/2007 Kaneeda et al.
2007/0146150 A1 6/2007 Calabrese et al.
2007/0153985 A1 7/2007 Tsao et al.
2007/0157323 A1 7/2007 Carlson et al.
2007/0163893 A1 7/2007 Filanovsky
2007/0166186 A1 7/2007 Stec
2007/0166585 A1 7/2007 Mench et al.
2007/0167853 A1 7/2007 Melker et al.
2007/0181426 A1 8/2007 Fleischer et al.
2007/0204388 A1 9/2007 Zyskowski et al.
2007/0222627 A1 9/2007 Chen et al.
2007/0229237 A1 10/2007 Kates
2007/0229834 A1 10/2007 Patel et al.
2007/0233360 A1 10/2007 Hill et al.
2007/0234708 A1 10/2007 Jones et al.
2007/0234730 A1 10/2007 Markham et al.
2007/0258849 A1 11/2007 Kent
2007/0261558 A1 11/2007 Ashworth
2007/0264680 A1 11/2007 Allef et al.
2007/0264927 A1 11/2007 Choi et al.
2007/0268367 A1 11/2007 Agmon
2007/0269854 A1 11/2007 Nigretto et al.
2007/0272211 A1 11/2007 Kassner
2007/0272852 A1 11/2007 Miller et al.
2007/0283682 A1 12/2007 Cullen et al.
2007/0298758 A1 12/2007 Verma et al.
2007/0298994 A1 12/2007 Finke et al.
2008/0007397 A1 1/2008 Glazer
2008/0014648 A1 1/2008 Poncelet et al.
2008/0018484 A1 1/2008 Sager
2008/0022756 A1 1/2008 Wilson et al.
2008/0028826 A1 2/2008 Schmitt et al.
2008/0030352 A1 2/2008 Shaw
2008/0034962 A1 2/2008 Kiern
2008/0036618 A1 2/2008 Von Gunten
2008/0049414 A1 2/2008 McKay
2008/0055098 A1 3/2008 Toland
2008/0062674 A1 3/2008 McKay
2008/0085860 A1 4/2008 Bokvist et al.
2008/0092631 A1 4/2008 Griswold
2008/0099333 A1 5/2008 Nair
2008/0110241 A1 5/2008 Rothschild et al.
2008/0129497 A1 6/2008 Woodard et al.
2008/0138051 A1 6/2008 Velazquez et al.
2008/0141754 A1 6/2008 Kates
2008/0143517 A1 6/2008 Goffin
2008/0149665 A1 6/2008 Hafer et al.
2008/0169934 A1 7/2008 Lang et al.
2008/0173817 A1 7/2008 Goldstein et al.
2008/0180260 A1 7/2008 Shirlee
2008/0180261 A1 7/2008 Shirlee
2008/0182506 A1 7/2008 Jackson et al.
2008/0191863 A1 8/2008 Boling et al.
2008/0224848 A1 9/2008 Meyer
2008/0224856 A1 9/2008 Verma et al.
2008/0231468 A1 9/2008 Myllymaki
2008/0242219 A1 10/2008 Wright
2008/0258903 A1 10/2008 Le et al.
2008/0258904 A1 10/2008 Moss
2008/0271439 A1 11/2008 Londos
2008/0280551 A1 11/2008 Ashworth
2008/0289962 A1 11/2008 Prohaska et al.
2008/0292495 A1 11/2008 Frechen et al.
2008/0302360 A1 12/2008 Chambers
2008/0303678 A1 12/2008 McCredy
2008/0312786 A1 12/2008 Day
2009/0001191 A1 1/2009 Gutovic
2009/0005917 A1 1/2009 Hole
2009/0019919 A1 1/2009 Derumez
2009/0029403 A1 1/2009 Fleischer et al.
2009/0038555 A1 2/2009 Reese
2009/0045937 A1 2/2009 Zimmerman
2009/0053989 A1 2/2009 Lunde et al.
2009/0058431 A1 3/2009 Dass et al.
2009/0074922 A1 3/2009 Garwood
2009/0089107 A1 4/2009 Angell et al.
2009/0101501 A1 4/2009 Tao et al.
2009/0102679 A1 4/2009 Schoettle
2009/0104072 A1 4/2009 Ando et al.
2009/0117012 A1 5/2009 Bankers et al.
2009/0120449 A1 5/2009 Tindall
2009/0121860 A1 5/2009 Kimmel et al.
2009/0124003 A1 5/2009 Matsunami et al.
2009/0126382 A1 5/2009 Rubino et al.
2009/0134993 A1 5/2009 Ashworth
2009/0139212 A1 6/2009 Miwa
2009/0139459 A1 6/2009 Habacivch et al.
2009/0151425 A1 6/2009 Miwa
2009/0163140 A1 6/2009 Packham et al.
2009/0165440 A1 7/2009 Sawada et al.
2009/0174561 A1 7/2009 Liu et al.
2009/0187111 A1 7/2009 Reilly, Jr. et al.
2009/0192340 A1 7/2009 Culp et al.
2009/0199543 A1 8/2009 Sawada et al.
2009/0212959 A1 8/2009 Suber, III
2009/0228151 A1 9/2009 Wang et al.
2009/0230300 A1 9/2009 Trevejo et al.
2009/0236153 A1 9/2009 Kyung et al.
2009/0239252 A1 9/2009 Trevejo et al.
2009/0246139 A1 10/2009 Woods et al.
2009/0251325 A1 10/2009 Smith et al.
2009/0260987 A1 10/2009 Valdes et al.
2009/0277602 A1 11/2009 Yang
2009/0277603 A1 11/2009 Yang
2009/0292469 A1 11/2009 Son et al.
2009/0309016 A1 12/2009 Almirall et al.
2009/0313971 A1 12/2009 Mueller-Stach et al.
2009/0320559 A1 12/2009 Lemieuvre et al.
2009/0321279 A1 12/2009 Holmen et al.
2009/0323055 A1 12/2009 Cole et al.
2010/0001417 A1 1/2010 D'Amico
2010/0002235 A1 1/2010 Willing et al.
2010/0008820 A1 1/2010 Savikko
2010/0024533 A1 2/2010 Kimura et al.
2010/0068821 A1 3/2010 St. Germain
2010/0069726 A1 3/2010 Levinson
2010/0073162 A1 3/2010 Johnson et al.
2010/0073172 A1 3/2010 Lax
2010/0082274 A1 4/2010 Son et al.
2010/0101214 A1 4/2010 Herman et al.
2010/0105311 A1 4/2010 Meneely, Jr.
2010/0111755 A1 5/2010 Bankers et al.
2010/0117828 A1 5/2010 Goldman et al.
2010/0119408 A1 5/2010 Hafer et al.
2010/0139366 A1 6/2010 Krausch
2010/0148946 A1 6/2010 Strombeck et al.
2010/0152958 A1* 6/2010 McAndrew, III ....... F01N 11/00
701/34.2
2010/0155691 A1 6/2010 Lee et al.
2010/0162790 A1 7/2010 Ziegler et al.
2010/0163429 A1 7/2010 Chiu et al.
2010/0178211 A1 7/2010 Ushijima
2010/0180667 A1 7/2010 Bender et al.
2010/0187332 A1 7/2010 Ushijima
2010/0188082 A1 7/2010 Morich et al.
2010/0191474 A1 7/2010 Haick
2010/0194574 A1 8/2010 Monk et al.
2010/0199373 A1 8/2010 Bringe et al.
2010/0199638 A1 8/2010 Yoshikawa
2010/0201530 A1 8/2010 Wende

(56) References Cited

U.S. PATENT DOCUMENTS

2010/0201531 A1 8/2010 Pakravan et al.
2010/0206039 A1 8/2010 Kates
2010/0211259 A1 8/2010 McClellan
2010/0211290 A1 8/2010 Kidokoro et al.
2010/0218595 A1 9/2010 Dikken et al.
2010/0218683 A1 9/2010 Chung et al.
2010/0219258 A1 9/2010 Starcic
2010/0219259 A1 9/2010 Starcic
2010/0222561 A1 9/2010 Matsunami et al.
2010/0231394 A1 9/2010 Finchum et al.
2010/0235114 A1 9/2010 Levy et al.
2010/0238018 A1 9/2010 Kelly
2010/0248268 A1 9/2010 Woods et al.
2010/0248661 A1 9/2010 Bullock
2010/0256954 A1 10/2010 Castella et al.
2010/0269805 A1 10/2010 Fukuda et al.
2010/0280836 A1 11/2010 Lu et al.
2010/0282245 A1 11/2010 Star et al.
2010/0290948 A1 11/2010 Song
2010/0302048 A1 12/2010 Mahajan
2010/0307231 A1 12/2010 Allard et al.
2010/0313630 A1 12/2010 Grozinger
2010/0315247 A1 12/2010 Tseng
2010/0330515 A1 12/2010 Ueki et al.
2011/0001625 A1 1/2011 Reilly, Jr. et al.
2011/0005207 A1 1/2011 Akihisa et al.
2011/0008212 A1 1/2011 Ichimura
2011/0013189 A1 1/2011 Johansen et al.
2011/0015496 A1 1/2011 Sherman et al.
2011/0015824 A1 1/2011 Ante et al.
2011/0016541 A1 1/2011 Weinstein et al.
2011/0030449 A1 2/2011 Hosono et al.
2011/0046916 A1 2/2011 Yu et al.
2011/0061368 A1 3/2011 Miyata et al.
2011/0063116 A1 3/2011 Lepley et al.
2011/0070158 A1 3/2011 Nutt et al.
2011/0084844 A1 4/2011 Carnation
2011/0088451 A1 4/2011 Holmes
2011/0090050 A1 4/2011 MacFarland
2011/0094457 A1 4/2011 Dee et al.
2011/0094459 A1 4/2011 Dee et al.
2011/0100210 A1 5/2011 Streib et al.
2011/0109464 A1 5/2011 Lepley et al.
2011/0112660 A1 5/2011 Bergmann et al.
2011/0113854 A1 5/2011 Kammerer et al.
2011/0114511 A1 5/2011 Sjong
2011/0142719 A1 6/2011 Goldstein et al.
2011/0144515 A1 6/2011 Bayer et al.
2011/0166769 A1 7/2011 Buechler et al.
2011/0170377 A1 7/2011 Legaspi
2011/0182918 A1 7/2011 Kalnik et al.
2011/0185787 A1 8/2011 Briens et al.
2011/0187542 A1 8/2011 Dittmer et al.
2011/0187543 A1 8/2011 Russo et al.
2011/0200488 A1 8/2011 Cennini et al.
2011/0202260 A1 8/2011 Cunningham et al.
2011/0203349 A1 8/2011 Reese
2011/0212376 A1 9/2011 Carney
2011/0226774 A1 9/2011 Kurz et al.
2011/0226864 A1 9/2011 Kim et al.
2011/0232269 A1 9/2011 Inoue
2011/0233288 A1 9/2011 Doll
2011/0243788 A1 10/2011 Garten
2011/0253359 A1 10/2011 Stockton
2011/0253797 A1 10/2011 Weening et al.
2011/0258992 A1 10/2011 Gonze et al.
2011/0259336 A1 10/2011 Lundeen
2011/0260875 A1 10/2011 Aarts et al.
2011/0271914 A1 11/2011 Richardson et al.
2011/0283770 A1 11/2011 Hok
2011/0284653 A1 11/2011 Butler et al.
2011/0295087 A1 12/2011 Shinoda et al.
2011/0296816 A1 12/2011 Parmentier et al.
2011/0310391 A1 12/2011 Janssen et al.
2011/0312102 A1 12/2011 Jo
2011/0317007 A1 12/2011 Kim
2012/0003746 A1 1/2012 Amisar
2012/0014839 A1 1/2012 Pen
2012/0016252 A1 1/2012 Melker et al.
2012/0031167 A1 2/2012 Chen et al.
2012/0046881 A1 2/2012 Cannon
2012/0047996 A1 3/2012 Reese
2012/0086576 A1 4/2012 Lin
2012/0090385 A1 4/2012 Michel et al.
2012/0091355 A1 4/2012 Rao et al.
2012/0103805 A1 5/2012 Holmen et al.
2012/0112920 A1 5/2012 Ramdeo
2012/0118044 A1 5/2012 Choi et al.
2012/0121511 A1 5/2012 Schmidt et al.
2012/0122079 A1 5/2012 Schmidt et al.
2012/0131905 A1 5/2012 Kwon
2012/0134876 A1 5/2012 Elrod
2012/0150755 A1 6/2012 Kumar et al.
2012/0171776 A1 7/2012 Jayaraman et al.
2012/0179388 A1 7/2012 Kuczynski et al.
2012/0180455 A1 7/2012 Severin et al.
2012/0191288 A1 7/2012 Qi et al.
2012/0210700 A1 8/2012 Sisken et al.
2012/0211515 A1 8/2012 An et al.
2012/0211523 A1 8/2012 An et al.
2012/0219459 A1 8/2012 Nakatani
2012/0222402 A1 9/2012 Keller et al.
2012/0224994 A1 9/2012 Steiner
2012/0230864 A1 9/2012 An et al.
2012/0268268 A1 10/2012 Bargero
2012/0268280 A1 10/2012 Hatch et al.
2012/0288950 A1 11/2012 Zang et al.
2012/0309048 A1 12/2012 Ratcliffe et al.
2012/0325184 A1 12/2012 Janssen et al.
2013/0005414 A1 1/2013 Bindra et al.
2013/0009785 A1 1/2013 Finn et al.
2013/0017120 A1 1/2013 Goldstein et al.
2013/0019653 A1 1/2013 Nakata
2013/0021160 A1 1/2013 Sid
2013/0036811 A1 2/2013 Boult
2013/0047841 A1 2/2013 Zidat
2013/0050466 A1 2/2013 Cetin et al.
2013/0055619 A1 3/2013 Stewart
2013/0056555 A1 3/2013 Yuhki et al.
2013/0059799 A1 3/2013 Liu et al.
2013/0062200 A1 3/2013 Sasaki
2013/0063259 A1 3/2013 Kramer et al.
2013/0066349 A1 3/2013 Fink et al.
2013/0077797 A1 3/2013 Hoy et al.
2013/0081541 A1 4/2013 Hasenoehrl et al.
2013/0090866 A1 4/2013 Ante et al.
2013/0093593 A1 4/2013 Woods
2013/0097999 A1 4/2013 Bouvier et al.
2013/0120788 A1 5/2013 Wang
2013/0123991 A1 5/2013 Richmond
2013/0134342 A1 5/2013 Shiffer
2013/0171733 A1 7/2013 Haick et al.
2013/0175168 A1 7/2013 Nemes
2013/0188544 A1 7/2013 Tiwari et al.
2013/0194089 A1 8/2013 Estrada
2013/0198670 A1 8/2013 Pelletier et al.
2013/0201024 A1 8/2013 Greenwood et al.
2013/0201316 A1 8/2013 Binder et al.
2013/0208114 A1 8/2013 Balsam
2013/0231846 A1 9/2013 Magner et al.
2013/0241727 A1 9/2013 Coulombe
2013/0244336 A1 9/2013 Mayer et al.
2013/0245919 A1 9/2013 Kumar et al.
2013/0263645 A1 10/2013 Jones
2013/0268177 A1 10/2013 Wu et al.
2013/0277389 A1 10/2013 Helf et al.
2013/0286213 A1 10/2013 Cetin et al.
2013/0292484 A1 11/2013 Jackson et al.
2013/0297192 A1 11/2013 Imeroski
2013/0300574 A1 11/2013 Gillette, II
2013/0301674 A1 11/2013 Gillette, II
2013/0304352 A1 11/2013 Macfarlane et al.
2013/0309713 A1 11/2013 Ribble et al.
2013/0316926 A1 11/2013 Caffrey

(56) References Cited

U.S. PATENT DOCUMENTS

2013/0318948 A1 12/2013 Van Marion
2013/0324617 A1 12/2013 Dannenberg et al.
2013/0327141 A1 12/2013 Floyd, Jr. et al.
2013/0340408 A1 12/2013 Narayanaswamy et al.
2014/0017989 A1 1/2014 Ganesan et al.
2014/0022968 A1 1/2014 Apte et al.
2014/0024960 A1 1/2014 Smith et al.
2014/0034284 A1 2/2014 Butler et al.
2014/0044425 A1 2/2014 Beesley
2014/0049642 A1 2/2014 Jiang et al.
2014/0055619 A1 2/2014 Holland et al.
2014/0060452 A1 3/2014 Linssen et al.
2014/0066003 A1 3/2014 Emerson et al.
2014/0066329 A1 3/2014 Hirschowitz et al.
2014/0069420 A1 3/2014 Richter et al.
2014/0074383 A1 3/2014 Frey
2014/0087369 A1 3/2014 Schmidt et al.
2014/0097953 A1 4/2014 Jelveh et al.
2014/0098445 A1 4/2014 Hooper
2014/0102443 A1 4/2014 Chambers
2014/0104067 A1 4/2014 Chien
2014/0127326 A1 5/2014 Sood et al.
2014/0163841 A1 6/2014 Sane
2014/0170194 A1 6/2014 Cetti et al.
2014/0188287 A1 7/2014 Sabata
2014/0202139 A1 7/2014 Qi et al.
2014/0202655 A1 7/2014 Yang
2014/0209192 A1 7/2014 Lawrence
2014/0217292 A1 8/2014 Monros
2014/0225731 A1 8/2014 Gouveia
2014/0238100 A1 8/2014 Londergan et al.
2014/0242562 A1 8/2014 McSterling et al.
2014/0253327 A1 9/2014 Tinaphong et al.
2014/0255258 A1 9/2014 Londos
2014/0266682 A1 9/2014 Gettings et al.
2014/0266747 A1 9/2014 Prendergast
2014/0277927 A1 9/2014 Guo et al.
2014/0278258 A1 9/2014 Shafer
2014/0284222 A1 9/2014 Wanek, Jr. et al.
2014/0284390 A1 9/2014 Teng et al.
2014/0294675 A1 10/2014 Melker et al.
2014/0294796 A1 10/2014 Wilson et al.
2014/0313040 A1 10/2014 Wright, Sr.
2014/0320296 A1 10/2014 Thurber et al.
2014/0322082 A1 10/2014 Hasenoehrl et al.
2014/0333442 A1 11/2014 Carney
2014/0338426 A1 11/2014 Noda et al.
2014/0343822 A1 11/2014 Varney
2014/0349566 A1 11/2014 Lamb et al.
2014/0360213 A1 12/2014 Son et al.
2014/0364330 A1 12/2014 Mershin et al.
2014/0366515 A1 12/2014 Kowalkowski et al.
2014/0367408 A1 12/2014 D'Amico
2014/0368354 A1 12/2014 Skourlis
2014/0375464 A1 12/2014 Caragata
2015/0014167 A1 1/2015 Dziallas et al.
2015/0022340 A1 1/2015 Gettings et al.
2015/0031582 A1 1/2015 Cai et al.
2015/0032019 A1 1/2015 Acker et al.
2015/0034484 A1 2/2015 Nakasone et al.
2015/0041682 A1 2/2015 Cano et al.
2015/0042469 A1 2/2015 Baldocchi et al.
2015/0047339 A1 2/2015 Rollinger et al.
2015/0056912 A1 2/2015 Scipio et al.
2015/0065030 A1 3/2015 Kates
2015/0065437 A1 3/2015 Liu et al.
2015/0077248 A1 3/2015 Eck
2015/0078964 A1 3/2015 Meirav et al.
2015/0080265 A1 3/2015 Elzinga et al.
2015/0090020 A1 4/2015 Takita et al.
2015/0090194 A1 4/2015 Pearce et al.
2015/0098860 A1 4/2015 Aldereguia et al.
2015/0098867 A1 4/2015 Aldereguia et al.
2015/0108241 A1 4/2015 Chase et al.
2015/0136616 A1 5/2015 Friedrich
2015/0140919 A1 5/2015 Zwijack
2015/0147818 A1 5/2015 Kim et al.
2015/0161452 A1 6/2015 McCarthy, II et al.
2015/0170490 A1 6/2015 Shaw
2015/0177202 A1 6/2015 Ozbek et al.
2015/0185192 A1 7/2015 Holmes
2015/0187194 A1 7/2015 Hypolite et al.
2015/0192048 A1 7/2015 Tanioka
2015/0199894 A1 7/2015 Braun et al.
2015/0206151 A1 7/2015 Carney et al.
2015/0211885 A1 7/2015 Rutherford et al.
2015/0212057 A1 7/2015 Darveau
2015/0235539 A1 8/2015 Orvis et al.
2015/0235540 A1 8/2015 Verna et al.
2015/0240772 A1 8/2015 Yamamoto et al.
2015/0250911 A1 9/2015 Bieri et al.
2015/0268210 A1 9/2015 Cristoforo
2015/0271201 A1 9/2015 Ruvio et al.
2015/0273395 A1 10/2015 Catalogna et al.
2015/0275804 A1 10/2015 Takano et al.
2015/0276693 A1 10/2015 Sid
2015/0289782 A1 10/2015 Peverall et al.
2015/0295562 A1 10/2015 Agarwal et al.
2015/0297778 A1 10/2015 Conroy et al.
2015/0302728 A1 10/2015 Gettings et al.
2015/0315967 A1 11/2015 Tuero
2015/0323941 A1 11/2015 Pariseau et al.
2015/0346175 A1 12/2015 Monros
2015/0348220 A1 12/2015 Sharma et al.
2015/0355151 A1 12/2015 Cleary
2015/0364340 A1 12/2015 Ueda
2015/0369774 A1 12/2015 Rabbett
2015/0372832 A1 12/2015 Kortz et al.
2015/0377102 A1 12/2015 Yezerets et al.
2016/0000956 A1 1/2016 Jenkins et al.
2016/0003180 A1 1/2016 McNulty et al.
2016/0003805 A1 1/2016 Ray et al.
2016/0012714 A1 1/2016 Patenaude et al.
2016/0022854 A1 1/2016 Shah
2016/0029693 A1 2/2016 Klein et al.
2016/0032812 A1 2/2016 Lee
2016/0049059 A1 2/2016 Engelmann et al.
2016/0054046 A1 2/2016 Sim
2016/0060355 A1 3/2016 Bhatnagar et al.
2016/0061087 A1 3/2016 Nagaoka
2016/0061476 A1 3/2016 Schultz et al.
2016/0061477 A1 3/2016 Schultz et al.
2016/0061794 A1 3/2016 Schultz et al.
2016/0061795 A1 3/2016 Schultz et al.
2016/0065414 A1 3/2016 Sundermeyer et al.
2016/0066067 A1 3/2016 Schultz et al.
2016/0069580 A1 3/2016 Crisa'
2016/0077071 A1 3/2016 Chancey
2016/0084136 A1 3/2016 Liu et al.
2016/0093187 A1 3/2016 Zhang et al.
2016/0097534 A1 4/2016 De Vries
2016/0097748 A1 4/2016 Hansen et al.
2016/0116913 A1 4/2016 Niles
2016/0123587 A1 5/2016 Ventura
2016/0125714 A1 5/2016 Kates et al.
2016/0133108 A1 5/2016 Bucsa et al.
2016/0144064 A1 5/2016 Santini et al.
2016/0146121 A1 5/2016 Carlson et al.
2016/0146751 A1 5/2016 Nemes
2016/0169851 A1 6/2016 Lee et al.
2016/0178228 A1 6/2016 Shahabdeen
2016/0186636 A1 6/2016 Odendall
2016/0202201 A1 7/2016 Cobianu et al.
2016/0213800 A1 7/2016 Tedesco
2016/0216174 A1 7/2016 Cloudt et al.
2016/0216244 A1 7/2016 Sobel et al.
2016/0223487 A1 8/2016 Okamoto et al.
2016/0225481 A1 8/2016 Yoon et al.
2016/0237732 A1 8/2016 Kerley
2016/0247369 A1 8/2016 Simmons
2016/0253887 A1 9/2016 Webb
2016/0256485 A1 9/2016 Wager et al.
2016/0258919 A1 9/2016 Allyn
2016/0269533 A1 9/2016 Taylor et al.

(56) References Cited

U.S. PATENT DOCUMENTS

2016/0272112 A1 9/2016 DeGrazia et al.
2016/0273437 A1 9/2016 Devarakonda
2016/0279574 A1 9/2016 Devarakonda
2016/0281623 A1 9/2016 Knuebel et al.
2016/0284176 A1 9/2016 Harrington et al.
2016/0319727 A1 11/2016 Nikolaus et al.
2016/0320308 A1 11/2016 Liss
2016/0321879 A1 11/2016 Oh et al.
2016/0321899 A1 11/2016 Mingo
2016/0327298 A1 11/2016 Sinha et al.
2016/0349216 A1 12/2016 Ichimura et al.
2016/0350715 A1 12/2016 Minvielle
2016/0368304 A1 12/2016 Mahbubani et al.
2016/0370255 A1 12/2016 Zahdeh et al.
2016/0370331 A1 12/2016 Nakada et al.
2016/0371969 A1 12/2016 Rossi et al.
2016/0376309 A1 12/2016 Liu et al.
2016/0377583 A1 12/2016 Takahashi
2017/0003179 A1 1/2017 Jin
2017/0003238 A1 1/2017 Salvador et al.
2017/0003246 A1 1/2017 Shuk et al.
2017/0011673 A1 1/2017 Condor
2017/0016906 A1 1/2017 Hirotsu et al.
2017/0018158 A1 1/2017 Sayavong et al.
2017/0045472 A1 2/2017 Zanon et al.
2017/0049597 A1 2/2017 Manne
2017/0051653 A1 2/2017 Martin et al.
2017/0052545 A1 2/2017 Cortez
2017/0056821 A1 3/2017 Beaulieu et al.
2017/0067659 A1 3/2017 Silver et al.
2017/0069190 A1 3/2017 Hansen et al.
2017/0073614 A1 3/2017 Alchenberger et al.
2017/0076403 A1 3/2017 Edwards et al.
2017/0078400 A1 3/2017 Binder et al.
2017/0080373 A1 3/2017 Engelhard
2017/0082305 A1 3/2017 Law
2017/0082574 A1 3/2017 Byun et al.
2017/0089247 A1 3/2017 Liu et al.
2017/0096955 A1 4/2017 Jung
2017/0098121 A1 4/2017 Ur
2017/0101941 A1 4/2017 Gladel et al.
2017/0102337 A1 4/2017 Benson et al.
2017/0106715 A1* 4/2017 Duan ....................... B60H 1/24
2017/0119919 A1 5/2017 Hsiao
2017/0122616 A1 5/2017 Calabro
2017/0130439 A1 5/2017 Kleinsasser et al.
2017/0130986 A1 5/2017 Wang et al.
2017/0140619 A1 5/2017 Russo et al.
2017/0157221 A1 6/2017 Fallon
2017/0175661 A1 6/2017 Kumar et al.
2017/0177815 A1 6/2017 Sundararajan et al.
2017/0184560 A1 6/2017 Crescini et al.
2017/0192399 A1 7/2017 Ramakrishnappa et al.
2017/0193788 A1 7/2017 Kim et al.
2017/0193789 A1 7/2017 Economy et al.
2017/0193798 A1 7/2017 Call et al.
2017/0209338 A1 7/2017 Potucek et al.
2017/0210286 A1 7/2017 Kasin
2017/0216892 A1 8/2017 Campanella et al.
2017/0226282 A1 8/2017 Deb
2017/0227491 A1 8/2017 Johnson et al.
2017/0232130 A1 8/2017 Conroy et al.
2017/0233679 A1 8/2017 Cetti et al.
2017/0234197 A1 8/2017 Dean
2017/0241321 A1 8/2017 Yoo et al.
2017/0241964 A1 8/2017 Vereecken et al.
2017/0242004 A1 8/2017 Hanson et al.
2017/0246334 A1 8/2017 Krishnan et al.
2017/0248541 A1 8/2017 Liu
2017/0261485 A1 9/2017 Panella et al.
2017/0266334 A1 9/2017 Tranzeat et al.
2017/0274737 A1 9/2017 Delaruelle
2017/0284689 A1 10/2017 Steele et al.
2017/0284690 A1 10/2017 Lipanov
2017/0284694 A1 10/2017 Park et al.
2017/0290294 A1 10/2017 Linssen et al.
2017/0311845 A1 11/2017 Cho et al.
2017/0315083 A1 11/2017 Bather et al.
2017/0315103 A1 11/2017 Biswas et al.
2017/0315107 A1 11/2017 Chou et al.
2017/0322167 A1 11/2017 Swager et al.
2017/0322181 A1 11/2017 White et al.
2017/0324936 A1 11/2017 Tran et al.
2017/0328259 A1 11/2017 Uchiyama et al.
2017/0328294 A1 11/2017 Poloni et al.
2017/0328816 A1 11/2017 Remondini
2017/0328877 A1 11/2017 Bajaj
2017/0335781 A1 11/2017 Augusty
2017/0342927 A1 11/2017 Miyamoto et al.
2017/0343501 A1 11/2017 Serban et al.
2017/0343517 A1 11/2017 Le Calve et al.
2017/0343521 A1 11/2017 Chang et al.
2017/0352236 A1 12/2017 Moses
2017/0352243 A1 12/2017 Quanci et al.
2017/0354231 A1 12/2017 Okumura et al.
2017/0363046 A1 12/2017 Dudar et al.
2017/0365151 A1 12/2017 Burleson
2017/0369168 A1 12/2017 Hwang et al.
2017/0370268 A1 12/2017 Meier et al.
2017/0370888 A1 12/2017 Lee et al.
2018/0003644 A1 1/2018 Christiansen
2018/0010994 A1 1/2018 Macomber
2018/0021467 A1 1/2018 Mainland et al.
2018/0027907 A1 2/2018 Singer
2018/0038825 A1 2/2018 Ratto et al.
2018/0040232 A1 2/2018 Wedig et al.
2018/0044258 A1 2/2018 Hahma et al.
2018/0050230 A1 2/2018 Toland
2018/0050330 A1 2/2018 Ishitani
2018/0050575 A1 2/2018 Campbell et al.
2018/0052655 A1 2/2018 Hannibal, III et al.
2018/0053140 A1 2/2018 Baca et al.
2018/0055134 A1 3/2018 Zhang
2018/0055288 A1 3/2018 Rose et al.
2018/0055488 A1 3/2018 Hall et al.
2018/0067091 A1 3/2018 Burkhalter et al.
2018/0073759 A1 3/2018 Zhang et al.
2018/0075724 A1 3/2018 Steiner et al.
2018/0078899 A1 3/2018 Remondini
2018/0078954 A1 3/2018 Gruenbacher et al.
2018/0080846 A1 3/2018 Zhang et al.
2018/0080912 A1 3/2018 Abbott et al.
2018/0087432 A1 3/2018 Odendall
2018/0087460 A1 3/2018 Pathan et al.
2018/0094564 A1 4/2018 Okamoto et al.
2018/0095061 A1 4/2018 Kane et al.
2018/0106755 A1 4/2018 Kayama et al.
2018/0108234 A1 4/2018 Cichon
2018/0110006 A1 4/2018 Kates
2018/0110457 A1 4/2018 Smith et al.
2018/0114430 A1 4/2018 Westmacott et al.
2018/0119973 A1 5/2018 Rothman et al.
2018/0120277 A1 5/2018 Chang et al.
2018/0120278 A1 5/2018 Hoorfar et al.
2018/0125374 A1 5/2018 Hall et al.
2018/0128145 A1 5/2018 Uhrich et al.
2018/0128771 A1 5/2018 Okamoto et al.
2018/0134112 A1 5/2018 Seiferlein et al.
2018/0135541 A1 5/2018 Hsieh et al.
2018/0135542 A1 5/2018 Baek et al.
2018/0136119 A1 5/2018 Pi
2018/0136187 A1 5/2018 Doutt et al.
2018/0141498 A1 5/2018 Savage
2018/0142590 A1 5/2018 Gupta et al.
2018/0142639 A1 5/2018 Miyamoto et al.
2018/0151061 A1 5/2018 Lauren
2018/0156096 A1 6/2018 Mitchell et al.
2018/0158309 A1 6/2018 Steins
2018/0164264 A1 6/2018 Savage
2018/0164273 A1 6/2018 Sieben et al.
2018/0171146 A1 6/2018 Allen et al.
2018/0172652 A1 6/2018 Voutilainen
2018/0178613 A1 6/2018 Zhang et al.
2018/0179979 A1 6/2018 Miyamoto et al.

(56) References Cited

U.S. PATENT DOCUMENTS

2018/0180493 A1 6/2018 Ishiguro et al.
2018/0182218 A1 6/2018 Toland
2018/0186198 A1 7/2018 Zhou et al.
2018/0188152 A1 7/2018 Vercruysse
2018/0188235 A1 7/2018 Ray et al.
2018/0189714 A1 7/2018 Azpitarte et al.
2018/0195988 A1 7/2018 Salvador et al.
2018/0195990 A1 7/2018 Yassine et al.
2018/0199921 A1 7/2018 Hall et al.
2018/0202890 A1 7/2018 Mutch et al.
2018/0202986 A1 7/2018 Knoefler et al.
2018/0204441 A1 7/2018 Zribi et al.
2018/0208637 A1 7/2018 Pfister et al.
2018/0209978 A1 7/2018 Postrel
2018/0211512 A1 7/2018 Zribi et al.
2018/0217131 A1 8/2018 Yu
2018/0223712 A1 8/2018 Ren et al.
2018/0224403 A1 8/2018 Ji et al.
2018/0225956 A1 8/2018 Chen
2018/0230879 A1 8/2018 Saitoh et al.
2018/0231515 A1 8/2018 Voumard
2018/0236119 A1 8/2018 Shah
2018/0245393 A1 8/2018 Ozkan
2018/0249735 A1 9/2018 Espinosa
2018/0249758 A1 9/2018 Derkalousdian et al.
2018/0250430 A1 9/2018 Machovina et al.
2018/0252669 A1 9/2018 Oh et al.
2018/0252701 A1 9/2018 Rhodes et al.
2018/0258821 A1 9/2018 Masubuchi et al.
2018/0260686 A1 9/2018 Tommy et al.
2018/0264156 A1 9/2018 O'Leary et al.
2018/0264299 A1 9/2018 Combe
2018/0266163 A1 9/2018 Combe
2018/0266169 A1 9/2018 Wray et al.
2018/0266977 A1 9/2018 Hashizume
2018/0267017 A1 9/2018 Love
2018/0271406 A1 9/2018 Furusaki et al.
2018/0273890 A1 9/2018 Shkolnikov et al.
2018/0274839 A1 9/2018 Kim et al.
2018/0276983 A1 9/2018 Tani et al.
2018/0282155 A1 10/2018 Haick
2018/0282588 A1 10/2018 Arigo et al.
2018/0283248 A1 10/2018 Upadhyay et al.
2018/0283308 A1 10/2018 Hayashita et al.
2018/0284048 A1 10/2018 Wakana et al.
2018/0285923 A1 10/2018 Fateh
2018/0290104 A1 10/2018 Jong
2018/0292286 A1 10/2018 Dittberner et al.
2018/0292309 A1 10/2018 Prasad
2018/0292374 A1 10/2018 Dittberner et al.
2018/0292520 A1 10/2018 Bermudez et al.
2018/0296650 A1 10/2018 Fallon
2018/0296719 A1 10/2018 Lane et al.
2018/0299150 A1 10/2018 Ajax et al.
2018/0299151 A1 10/2018 Ajax et al.
2018/0299156 A1 10/2018 Ajax et al.
2018/0299159 A1 10/2018 Ajax et al.
2018/0303963 A1 10/2018 Park et al.
2018/0305010 A1 10/2018 Baracaldo Angel et al.
2018/0305734 A1 10/2018 Sato et al.
2018/0308340 A1 10/2018 Thiyagarajah et al.
2018/0312562 A1 11/2018 Zhang et al.
2018/0318189 A1 11/2018 Hatt et al.
2018/0320646 A1 11/2018 Naclerio
2018/0320916 A1 11/2018 Vincitore et al.
2018/0322405 A1 11/2018 Fadell et al.
2018/0335409 A1 11/2018 Kao et al.
2018/0335413 A1 11/2018 Jouper
2018/0346130 A1 12/2018 Jouper
2018/0350220 A1 12/2018 Gonzales
2018/0353891 A1 12/2018 Cho et al.
2018/0356357 A1 12/2018 Samarao
2018/0356383 A1 12/2018 Phelipot et al.
2018/0357871 A1 12/2018 Siminoff
2018/0362579 A1 12/2018 Wilson et al.
2018/0363577 A1 12/2018 Ulrey et al.
2018/0369442 A1 12/2018 Kelsen
2018/0369847 A1 12/2018 Kihm et al.
2018/0372011 A1 12/2018 Hagari
2018/0372330 A1 12/2018 Ronda et al.
2018/0372637 A1 12/2018 He et al.
2018/0375820 A1 12/2018 Smith et al.
2019/0001015 A1 1/2019 Fiedler et al.
2019/0002952 A1 1/2019 Rodenrys
2019/0003480 A1 1/2019 Hall et al.
2019/0004021 A1 1/2019 Yu
2019/0005811 A1 1/2019 Saia et al.
2019/0011336 A1 1/2019 Mou et al.
2019/0011390 A1 1/2019 Mou et al.
2019/0011391 A1 1/2019 Mou et al.
2019/0011392 A1 1/2019 Mou et al.
2019/0011394 A1 1/2019 Mou et al.
2019/0011949 A1 1/2019 Mou et al.
2019/0017427 A1 1/2019 Dudar
2019/0017453 A1 1/2019 Dudar
2019/0018378 A1 1/2019 Varikooty et al.
2019/0019033 A1 1/2019 Chang et al.
2019/0022132 A1 1/2019 Wager et al.
2019/0025243 A1 1/2019 Yu et al.
2019/0025246 A1 1/2019 Liu et al.
2019/0025264 A1 1/2019 Peng et al.
2019/0033170 A1 1/2019 Dudar
2019/0033177 A1 1/2019 Mou et al.
2019/0033253 A1 1/2019 Yu et al.
2019/0033278 A1 1/2019 Mou et al.
2019/0033280 A1 1/2019 Mou et al.
2019/0033290 A1 1/2019 Koo et al.
2019/0041370 A1 2/2019 Gao et al.
2019/0041371 A1 2/2019 Dinsmore
2019/0051639 A1 2/2019 Hussain et al.
2019/0056125 A1 2/2019 Mou et al.
2019/0056292 A1 2/2019 Mou et al.
2019/0056366 A1 2/2019 Mou et al.
2019/0056367 A1 2/2019 Mou et al.
2019/0056368 A1 2/2019 Mou et al.
2019/0056369 A1 2/2019 Mou et al.
2019/0056766 A1 2/2019 Mou et al.
2019/0059725 A1 2/2019 Greiner
2019/0060821 A1 2/2019 Mou et al.
2019/0061466 A1 2/2019 MacNeille et al.
2019/0063421 A1 2/2019 Mou et al.
2019/0063678 A1 2/2019 Ganiger et al.
2019/0063762 A1 2/2019 Lee et al.
2019/0064104 A1 2/2019 Mou et al.
2019/0064134 A1 2/2019 Mou et al.
2019/0066483 A1 2/2019 Darling et al.
2019/0066488 A1 2/2019 Locke et al.
2019/0069516 A1 3/2019 Pearce et al.
2019/0070086 A1 3/2019 Cetti et al.
2019/0070547 A1 3/2019 Sappok et al.
2019/0072020 A1 3/2019 Hagiwara et al.
2019/0082737 A1 3/2019 Smith et al.
2019/0086410 A1 3/2019 Wright et al.
2019/0095078 A1 3/2019 Marshall et al.
2019/0097833 A1 3/2019 Doerner et al.
2019/0101033 A1 4/2019 Yoda et al.
2019/0101302 A1 4/2019 Rainone et al.
2019/0101501 A1 4/2019 Sahu et al.
2019/0101515 A1 4/2019 Konieczka et al.
2019/0105250 A1 4/2019 Singer et al.
2019/0105960 A1 4/2019 Dudar
2019/0106458 A1 4/2019 Liu et al.
2019/0106639 A1 4/2019 Rovani, Jr. et al.
2019/0107081 A1 4/2019 Dudar
2019/0108738 A1 4/2019 Al Hajjaj
2019/0108739 A1 4/2019 Wedig et al.
2019/0112330 A1 4/2019 Wright et al.
2019/0112993 A1 4/2019 Noh et al.
2019/0113491 A1 4/2019 Xie et al.
2019/0113494 A1 4/2019 Desjardins
2019/0114671 A1 4/2019 Briggs et al.
2019/0114891 A1 4/2019 Eck
2019/0114904 A1 4/2019 Subramanian
2019/0117815 A1 4/2019 Wei et al.

(56) References Cited

U.S. PATENT DOCUMENTS

2019/0120101 A1 4/2019 Dadam et al.
2019/0124194 A1 4/2019 Stolte
2019/0128780 A1 5/2019 Pilon et al.
2019/0130718 A1 5/2019 Alpert
2019/0135270 A1 5/2019 Dudar
2019/0135271 A1 5/2019 Garcia
2019/0135552 A1 5/2019 Martono et al.
2019/0137464 A1 5/2019 Kasper et al.
2019/0137476 A1 5/2019 Davis et al.
2019/0137480 A1 5/2019 Arregui San Martin et al.
2019/0142326 A1 5/2019 Mills
2019/0142329 A1 5/2019 Mills
2019/0144353 A1 5/2019 Wang et al.
2019/0145644 A1 5/2019 Karamanos et al.
2019/0152995 A1 5/2019 Gunasekaran et al.
2019/0154285 A1 5/2019 Pham et al.
2019/0154571 A1 5/2019 Kuczynski et al.
2019/0154645 A1 5/2019 Kim et al.
2019/0156940 A1 5/2019 Jackson
2019/0160195 A1 5/2019 Kelsen
2019/0160425 A1 5/2019 Beaulieu et al.
2019/0160907 A1 5/2019 Velazquez et al.
2019/0162154 A1 5/2019 Pompea et al.
2019/0162159 A1 5/2019 Dudar
2019/0166413 A1 5/2019 Klinger et al.
2019/0167152 A1 6/2019 Weda et al.
2019/0167831 A1 6/2019 Chan et al.
2019/0168711 A1 6/2019 Oesterling et al.
2019/0169916 A1 6/2019 Morgan et al.
2019/0170061 A1 6/2019 Dudar
2019/0170690 A1 6/2019 Qiu et al.
2019/0170691 A1 6/2019 Hsi et al.
2019/0172332 A1 6/2019 Kraz et al.
2019/0172333 A1 6/2019 Combe
2019/0176810 A1 6/2019 Dudar
2019/0178187 A1 6/2019 Smith et al.
2019/0180596 A1 6/2019 Glasgow et al.
2019/0183887 A1 6/2019 Koo et al.
2019/0186392 A1 6/2019 Dudar et al.
2019/0187035 A1 6/2019 Mou et al.
2019/0187120 A1 6/2019 Russell et al.
2019/0195112 A1 6/2019 Negishi et al.
2019/0195160 A1 6/2019 Negishi et al.
2019/0195464 A1 6/2019 Dong et al.
2019/0195828 A1 6/2019 Knoefler et al.
2019/0195845 A1 6/2019 Kim
2019/0195848 A1 6/2019 Mou et al.
2019/0195849 A1 6/2019 Mou et al.
2019/0195850 A1 6/2019 Mou et al.
2019/0197856 A1 6/2019 Gracin
2019/0197858 A1 6/2019 Moses
2019/0197868 A1 6/2019 Guerin
2019/0197876 A1 6/2019 Mullins et al.
2019/0197878 A1 6/2019 Rubio Corredera
2019/0200206 A1 6/2019 Rubio Corredera
2019/0203256 A1 7/2019 Koo et al.
2019/0203300 A1 7/2019 Darling et al.
2019/0203668 A1 7/2019 Dudar et al.
2019/0203959 A1 7/2019 Aleti
2019/0203960 A1 7/2019 Hoyda et al.
2019/0204279 A1 7/2019 Luo
2019/0204282 A1 7/2019 Gong et al.
2019/0209022 A1 7/2019 Sobol et al.
2019/0211736 A1 7/2019 Reitmeier et al.
2019/0211768 A1 7/2019 Dudar
2019/0212012 A1 7/2019 Le
2019/0212242 A1 7/2019 Mou et al.
2019/0213867 A1 7/2019 Tani et al.
2019/0219540 A1 7/2019 Mohanty et al.
2019/0221095 A1 7/2019 Bonnard et al.
2019/0221101 A1 7/2019 Golob
2019/0221108 A1 7/2019 Harris et al.
2019/0225632 A1 7/2019 Braddock-Wilking et al.
2019/0225659 A1 7/2019 Takahashi et al.
2019/0227015 A1 7/2019 Kuczynski et al.
2019/0227042 A1 7/2019 Hashizume et al.
2019/0227044 A1 7/2019 Ando et al.
2019/0227053 A1 7/2019 Rinberg et al.
2019/0230402 A1 7/2019 Fox
2019/0231267 A1 8/2019 Oren et al.
2019/0232951 A1 8/2019 Dudar
2019/0234326 A1 8/2019 Dudar
2019/0234521 A1 8/2019 Halbheer et al.
2019/0234838 A1 8/2019 Mou et al.
2019/0234839 A1 8/2019 Mou et al.
2019/0234840 A1 8/2019 Mou et al.
2019/0234851 A1 8/2019 Mou et al.
2019/0234895 A1 8/2019 Smilanich et al.
2019/0236678 A1 8/2019 Wilkinson et al.
2019/0239564 A1 8/2019 Utley et al.
2019/0242599 A1 8/2019 Sakai et al.
2019/0249622 A1 8/2019 Dudar et al.
2019/0250133 A1 8/2019 Shao et al.
2019/0250136 A1 8/2019 Kim et al.
2019/0250148 A1 8/2019 Matsunami
2019/0251767 A1 8/2019 Makita et al.
2019/0256082 A1 8/2019 Eloy et al.
2019/0257143 A1 8/2019 Nagel et al.
2019/0257235 A1 8/2019 Van Nieuwstadt et al.
2019/0257236 A1 8/2019 Pfister et al.
2019/0257241 A1 8/2019 Heinken
2019/0257543 A1 8/2019 Martin
2019/0258278 A1 8/2019 Zokaei et al.
2019/0263226 A1 8/2019 Gruenbeck et al.
2019/0264628 A1 8/2019 Dudar
2019/0265132 A1 8/2019 Mou et al.
2019/0266860 A1 8/2019 Lakshmipathy et al.
2019/0266871 A1 8/2019 Verna et al.
2019/0268458 A1 8/2019 DeBates et al.
2019/0271254 A1 9/2019 Frobert et al.
2019/0271685 A1 9/2019 Haick et al.
2019/0273817 A1 9/2019 Ueno et al.
2019/0275465 A1 9/2019 Shirasawa et al.
2019/0276602 A1 9/2019 De Castro et al.
2019/0277522 A1 9/2019 Soyyigit
2019/0277731 A1 9/2019 Hur et al.
2019/0283529 A1* 9/2019 Macneille .......... B60H 1/00771
2019/0285020 A1 9/2019 Dudar et al.
2019/0289803 A1 9/2019 Gagne et al.
2019/0292600 A1 9/2019 Spira et al.
2019/0292969 A1 9/2019 Van Nieuwstadt et al.
2019/0293008 A1 9/2019 Wodausch et al.
2019/0293288 A1 9/2019 Deyoung et al.
2019/0293628 A1 9/2019 Hanson et al.
2019/0301761 A1 10/2019 Scheja et al.
2019/0302072 A1 10/2019 Mou et al.
2019/0302073 A1 10/2019 Mou et al.
2019/0302075 A1 10/2019 Mou et al.
2019/0302076 A1 10/2019 Mou et al.
2019/0304280 A1 10/2019 Bajaj et al.
2019/0309671 A1 10/2019 Rajagopal et al.
2019/0310097 A1 10/2019 Makita et al.
2019/0311595 A1 10/2019 Lacy
2019/0311598 A1 10/2019 Johnston
2019/0313944 A1 10/2019 Sun et al.
2019/0315003 A1 10/2019 Iwanami
2019/0316538 A1 10/2019 Martin et al.
2019/0317073 A1 10/2019 Horvath
2019/0317079 A1 10/2019 Trenholm et al.
2019/0318598 A1 10/2019 Aponte Luis
2019/0319316 A1 10/2019 Fifield
2019/0323441 A1 10/2019 Yuan et al.
2019/0323985 A1 10/2019 Xiao et al.
2019/0324004 A1 10/2019 Feinstein et al.
2019/0328924 A1 10/2019 Peterson et al.
2019/0331038 A1 10/2019 Brahma et al.
2019/0331044 A1 10/2019 Minaz et al.
2019/0331062 A1 10/2019 Dudar et al.
2019/0331068 A1 10/2019 Badawy et al.
2019/0331359 A1 10/2019 Sakaguchi et al.
2019/0331558 A1 10/2019 Mou et al.
2019/0331582 A1 10/2019 Mou et al.
2019/0331619 A1 10/2019 Choi et al.
2019/0334740 A1 10/2019 Mohiuddin et al.

(56) References Cited

U.S. PATENT DOCUMENTS

2019/0336374 A1 11/2019 McClain
2019/0338354 A1 11/2019 Gonzales, Jr.
2019/0339279 A1 11/2019 Duhamel et al.
2019/0340913 A1 11/2019 Downs et al.
2019/0342948 A1 11/2019 Louveau et al.
2019/0342973 A1 11/2019 Schiffer et al.
2019/0346401 A1 11/2019 Kralicek et al.
2019/0346417 A1 11/2019 Benefield
2019/0347924 A1 11/2019 Trundle et al.
2019/0353418 A1 11/2019 Akinci et al.
2019/0355234 A1 11/2019 Kim
2019/0357763 A1 11/2019 Malkar et al.
2019/0359056 A1 11/2019 Wilson et al.
2019/0360413 A1 11/2019 Uhrich et al.
2019/0360434 A1 11/2019 Dudar et al.
2019/0360963 A1 11/2019 Shuk et al.
2019/0360985 A1 11/2019 Hong
2019/0365572 A1 12/2019 Park et al.
2019/0365941 A1 12/2019 Elrod
2019/0367963 A1 12/2019 Yoshikawa et al.
2019/0369073 A1 12/2019 Gafsou
2019/0369139 A1 12/2019 Mohtashami et al.
2019/0371137 A1 12/2019 Fortin et al.
2019/0375395 A1 12/2019 Jentz et al.
2019/0376433 A1 12/2019 Wiebenga et al.
2019/0376877 A1 12/2019 Mou et al.
2019/0376903 A1 12/2019 Kurata et al.
2019/0381996 A1 12/2019 Kaneko et al.
2019/0383557 A1 12/2019 Jensen et al.
2019/0383772 A1 12/2019 Kuroki et al.
2019/0383779 A1 12/2019 Bruchet et al.
2019/0387375 A1 12/2019 Gao
2019/0391082 A1 12/2019 Yoon
2019/0393699 A1 12/2019 Shastri et al.
2020/0000369 A1 1/2020 Tiemann et al.
2020/0002399 A1 1/2020 Pfister et al.
2020/0003142 A1 1/2020 Pachner et al.
2020/0003143 A1 1/2020 Dudar
2020/0003144 A1 1/2020 Faied
2020/0003774 A1 1/2020 Hanson et al.
2020/0005059 A1 1/2020 Yamada et al.
2020/0005617 A1 1/2020 Janscha et al.
2020/0008395 A1 1/2020 Mischley
2020/0011560 A1 1/2020 Minamida et al.
2020/0012883 A1 1/2020 Kuo et al.
2020/0013273 A1 1/2020 Souloglou
2020/0016564 A1 1/2020 Surwade et al.
2020/0018714 A1 1/2020 Carr
2020/0019168 A1 1/2020 Guzman et al.
2020/0020220 A1 1/2020 Stefanski et al.
2020/0024406 A1 1/2020 Zhao et al.
2020/0025717 A1 1/2020 Manginell et al.
2020/0025734 A1 1/2020 Amin et al.
2020/0025735 A1 1/2020 Bardoni et al.
2020/0025737 A1 1/2020 Al Madani et al.
2020/0027322 A1 1/2020 Mundra et al.
2020/0029858 A1 1/2020 Reddy
2020/0033020 A1 1/2020 Fujii et al.
2020/0033279 A1 1/2020 Hur et al.
2020/0033900 A1 1/2020 Allen et al.
2020/0036310 A1 1/2020 Sarder et al.
2020/0049043 A1 2/2020 Nose et al.
2020/0049048 A1 2/2020 Franz et al.
2020/0049091 A1 2/2020 Dai et al.
2022/0054966 A1* 2/2022 Varughese ......... B01D 46/0049
2022/0055439 A1* 2/2022 Varughese ......... B60H 1/00028
2022/0055440 A1* 2/2022 Varughese ............... B60N 2/56
2022/0055441 A1* 2/2022 Varughese ......... G06Q 30/0251
2022/0055456 A1* 2/2022 Varughese ............... B60H 3/06
2022/0055457 A1* 2/2022 Varughese ............. B60H 1/008
2022/0056824 A1* 2/2022 Varughese ......... G01N 33/0047
2022/0058930 A1* 2/2022 Varughese ............ G01N 15/06
2022/0059119 A1* 2/2022 Varughese ............ G06Q 50/22
2022/0185060 A1* 6/2022 Feldman ............ B60H 1/00771
2022/0196507 A1* 6/2022 Subrahmanyam ...... G01M 3/20
2023/0067927 A1* 3/2023 Zhang .................. G01N 1/2205

FOREIGN PATENT DOCUMENTS

CA 2272116 A1 11/2000
CA 2307443 A1 11/2000
CA 2379540 A1 12/2000
CA 2326848 A1 3/2001
CA 2384742 A1 3/2001
CA 2287028 A1 4/2001
CA 2389708 A1 5/2001
CA 2389730 A1 5/2001
CA 2298355 A1 8/2001
CA 2298359 A1 8/2001
CA 2397790 A1 8/2001
CA 2402379 A1 8/2001
CA 2402371 A1 9/2001
CA 2402870 A1 9/2001
CA 2314237 A1 1/2002
CA 2416084 A1 2/2002
CA 2421772 A1 3/2002
CA 2373374 A1 8/2002
CA 2442581 A1 10/2002
CA 2429854 A1 11/2002
CA 2353759 A1 1/2003
CA 2381871 A1 2/2003
CA 2369720 A1 7/2003
CA 2310279 C 8/2003
CA 2484770 A1 11/2003
CA 2488451 A1 12/2003
CA 2489309 A1 12/2003
CA 2437420 A1 2/2004
CA 2498864 A1 4/2004
CA 2504452 A1 5/2004
CA 2452464 A1 6/2004
CA 2507044 A1 6/2004
CA 2316535 C 7/2004
CA 2507300 A1 7/2004
CA 2360616 C 8/2004
CA 2511379 A1 8/2004
CA 2515144 A1 8/2004
CA 2423512 A1 9/2004
CA 2523602 A1 11/2004
CA 2496025 A1 1/2005
CA 2535419 A1 2/2005
CA 2499198 A1 9/2005
CA 2418612 C 12/2005
CA 2502031 A1 12/2005
CA 2540709 A1 12/2005
CA 2566606 A1 12/2005
CA 2403417 C 1/2006
CA 2360595 C 2/2006
CA 2395563 C 3/2006
CA 2529880 A1 4/2006
CA 2338006 C 5/2006
CA 2353033 C 5/2006
CA 2593716 A1 8/2006
CA 2597762 A1 8/2006
CA 2500116 A1 9/2006
CA 2600438 A1 9/2006
CA 2601405 A1 9/2006
CA 2274572 C 10/2006
CA 2603956 A1 10/2006
CA 2400109 C 11/2006
CA 2606664 A1 11/2006
CA 2609759 A1 12/2006
CA 2433314 C 3/2007
CA 2453224 C 3/2007
CA 2623003 A1 3/2007
CA 2630577 A1 6/2007
CA 2573284 A1 7/2007
CA 2635682 A1 7/2007
CA 2449549 C 8/2007
CA 2526148 C 8/2007
CA 2633826 A1 8/2007
CA 2583447 A1 9/2007
CA 2582967 A1 10/2007

(56) References Cited

FOREIGN PATENT DOCUMENTS

| | | | |
|---|---|---|---|
| CA | 2587814 | A1 | 11/2007 |
| CA | 2651482 | A1 | 11/2007 |
| CA | 2450172 | C | 1/2008 |
| CA | 2660623 | A1 | 2/2008 |
| CA | 2341065 | C | 5/2008 |
| CA | 2452124 | C | 5/2008 |
| CA | 2679597 | A1 | 6/2008 |
| CA | 2616362 | A1 | 7/2008 |
| CA | 2446710 | C | 8/2008 |
| CA | 2515250 | C | 9/2008 |
| CA | 2692948 | A1 | 9/2008 |
| CA | 2446315 | C | 10/2008 |
| CA | 2478112 | C | 11/2008 |
| CA | 2725319 | A1 | 11/2008 |
| CA | 2687494 | A1 | 12/2008 |
| CA | 2448849 | C | 1/2009 |
| CA | 2452465 | C | 1/2009 |
| CA | 2440357 | C | 2/2009 |
| CA | 2694918 | A1 | 2/2009 |
| CA | 2696044 | A1 | 2/2009 |
| CA | 2604184 | A1 | 4/2009 |
| CA | 2374987 | C | 6/2009 |
| CA | 2715403 | A1 | 8/2009 |
| CA | 2370835 | C | 9/2009 |
| CA | 2417149 | C | 9/2009 |
| CA | 2525523 | C | 9/2009 |
| CA | 2511519 | C | 10/2009 |
| CA | 2572422 | C | 10/2009 |
| CA | 2720633 | A1 | 10/2009 |
| CA | 2444072 | C | 12/2009 |
| CA | 2480915 | C | 12/2009 |
| CA | 2727617 | A1 | 12/2009 |
| CA | 2769663 | A1 | 2/2010 |
| CA | 2703218 | A1 | 4/2010 |
| CA | 2419110 | C | 6/2010 |
| CA | 2419124 | C | 6/2010 |
| CA | 2483684 | C | 7/2010 |
| CA | 2750019 | A1 | 7/2010 |
| CA | 2750292 | A1 | 7/2010 |
| CA | 2751223 | A1 | 8/2010 |
| CA | 2749597 | A1 | 9/2010 |
| CA | 2767496 | A1 | 9/2010 |
| CA | 2669861 | A1 | 10/2010 |
| CA | 2757541 | A1 | 10/2010 |
| CA | 2668302 | A1 | 12/2010 |
| CA | 2388591 | C | 1/2011 |
| CA | 2401046 | C | 1/2011 |
| CA | 2769266 | A1 | 2/2011 |
| CA | 2772744 | A1 | 3/2011 |
| CA | 2477722 | C | 4/2011 |
| CA | 2529669 | C | 4/2011 |
| CA | 2777622 | A1 | 4/2011 |
| CA | 2777623 | A1 | 4/2011 |
| CA | 2777624 | A1 | 4/2011 |
| CA | 2777625 | A1 | 4/2011 |
| CA | 2466324 | C | 5/2011 |
| CA | 2604264 | C | 6/2011 |
| CA | 2787303 | A1 | 7/2011 |
| CA | 2413279 | C | 8/2011 |
| CA | 2385599 | C | 9/2011 |
| CA | 2791937 | A1 | 9/2011 |
| CA | 2794130 | A1 | 10/2011 |
| CA | 2794388 | A1 | 10/2011 |
| CA | 2473735 | C | 11/2011 |
| CA | 2491490 | C | 12/2011 |
| CA | 2703594 | C | 1/2012 |
| CA | 2375021 | C | 2/2012 |
| CA | 2810678 | A1 | 3/2012 |
| CA | 2811394 | A1 | 3/2012 |
| CA | 2471897 | C | 4/2012 |
| CA | 2813721 | A1 | 4/2012 |
| CA | 2758665 | A1 | 5/2012 |
| CA | 2761030 | A1 | 6/2012 |
| CA | 2698926 | C | 8/2012 |
| CA | 2746893 | C | 8/2012 |
| CA | 2563790 | C | 10/2012 |
| CA | 2486221 | C | 12/2012 |
| CA | 2583455 | C | 12/2012 |
| CA | 2731162 | C | 12/2012 |
| CA | 2838505 | A1 | 12/2012 |
| CA | 2548252 | C | 1/2013 |
| CA | 2840209 | A1 | 1/2013 |
| CA | 2648068 | C | 2/2013 |
| CA | 2709084 | C | 2/2013 |
| CA | 2564393 | C | 3/2013 |
| CA | 2588074 | C | 3/2013 |
| CA | 2753400 | A1 | 3/2013 |
| CA | 2789481 | A1 | 3/2013 |
| CA | 2847348 | A1 | 3/2013 |
| CA | 2847886 | A1 | 3/2013 |
| CA | 2665677 | C | 4/2013 |
| CA | 2666662 | C | 4/2013 |
| CA | 2571080 | C | 5/2013 |
| CA | 2616631 | C | 5/2013 |
| CA | 2854677 | A1 | 5/2013 |
| CA | 2858550 | A1 | 6/2013 |
| CA | 2536375 | C | 7/2013 |
| CA | 2541756 | C | 7/2013 |
| CA | 2734770 | C | 7/2013 |
| CA | 2802306 | A1 | 7/2013 |
| CA | 2679927 | C | 8/2013 |
| CA | 2863835 | A1 | 8/2013 |
| CA | 2867491 | A1 | 9/2013 |
| CA | 2470115 | C | 10/2013 |
| CA | 2887367 | A1 | 11/2013 |
| CA | 2584498 | C | 12/2013 |
| CA | 2820237 | A1 | 1/2014 |
| CA | 2879131 | A1 | 1/2014 |
| CA | 2789248 | A1 | 3/2014 |
| CA | 2816340 | C | 3/2014 |
| CA | 2827173 | A1 | 3/2014 |
| CA | 2359625 | C | 4/2014 |
| CA | 2390261 | C | 4/2014 |
| CA | 2730527 | C | 4/2014 |
| CA | 2575998 | C | 5/2014 |
| CA | 2833846 | A1 | 5/2014 |
| CA | 2889843 | A1 | 5/2014 |
| CA | 2801978 | A1 | 7/2014 |
| CA | 2803125 | A1 | 7/2014 |
| CA | 2814256 | C | 7/2014 |
| CA | 2899195 | A1 | 9/2014 |
| CA | 2904262 | A1 | 9/2014 |
| CA | 2905091 | A1 | 9/2014 |
| CA | 2906458 | A1 | 9/2014 |
| CA | 2906963 | A1 | 9/2014 |
| CA | 2699171 | C | 10/2014 |
| CA | 2909892 | A1 | 10/2014 |
| CA | 2918594 | A1 | 11/2014 |
| CA | 2914259 | A1 | 12/2014 |
| CA | 2916204 | A1 | 12/2014 |
| CA | 2679102 | C | 1/2015 |
| CA | 2918680 | A1 | 1/2015 |
| CA | 3033768 | A1 | 1/2015 |
| CA | 2803152 | C | 2/2015 |
| CA | 2861749 | A1 | 3/2015 |
| CA | 2866032 | A1 | 4/2015 |
| CA | 2925542 | A1 | 4/2015 |
| CA | 2926442 | A1 | 4/2015 |
| CA | 2926453 | A1 | 4/2015 |
| CA | 2926811 | A1 | 4/2015 |
| CA | 2964002 | A1 | 4/2015 |
| CA | 2633326 | C | 5/2015 |
| CA | 2870508 | A1 | 5/2015 |
| CA | 2932408 | A1 | 6/2015 |
| CA | 2938039 | A1 | 7/2015 |
| CA | 2889380 | A1 | 10/2015 |
| CA | 2946448 | A1 | 10/2015 |
| CA | 2951690 | A1 | 12/2015 |
| CA | 2456621 | C | 1/2016 |
| CA | 2896120 | A1 | 1/2016 |
| CA | 2608943 | C | 2/2016 |
| CA | 2674528 | C | 2/2016 |
| CA | 2958077 | A1 | 2/2016 |
| CA | 2770150 | C | 3/2016 |

(56) References Cited

FOREIGN PATENT DOCUMENTS

| | | | | | |
|---|---|---|---|---|---|
| CA | 2814372 | C | | 3/2016 | |
| CA | 2734783 | C | | 4/2016 | |
| CA | 2963635 | A1 | | 4/2016 | |
| CA | 2963780 | A1 | | 4/2016 | |
| CA | 2964416 | A1 | | 4/2016 | |
| CA | 2794670 | C | | 5/2016 | |
| CA | 2965455 | A1 | | 5/2016 | |
| CA | 2966524 | A1 | | 5/2016 | |
| CA | 2641889 | C | | 6/2016 | |
| CA | 2789869 | C | | 6/2016 | |
| CA | 2707457 | C | | 7/2016 | |
| CA | 2670457 | C | | 8/2016 | |
| CA | 2887929 | A1 | | 9/2016 | |
| CA | 2923265 | A1 | | 9/2016 | |
| CA | 2978703 | A1 | | 9/2016 | |
| CA | 2918662 | C | | 11/2016 | |
| CA | 2928212 | A1 | | 11/2016 | |
| CA | 2983380 | A1 | | 11/2016 | |
| CA | 2558851 | C | | 12/2016 | |
| CA | 2663126 | C | | 12/2016 | |
| CA | 2986845 | A1 | | 12/2016 | |
| CA | 2989000 | A1 | | 12/2016 | |
| CA | 2935406 | A1 | | 1/2017 | |
| CA | 2935820 | A1 | | 1/2017 | |
| CA | 2991087 | A1 | | 1/2017 | |
| CA | 2945501 | A1 | | 4/2017 | |
| CA | 3000566 | A1 | | 4/2017 | |
| CA | 2645534 | C | | 5/2017 | |
| CA | 2950795 | A1 | | 6/2017 | |
| CA | 3008800 | A1 | | 6/2017 | |
| CA | 2884660 | C | | 7/2017 | |
| CA | 2952364 | A1 | | 7/2017 | |
| CA | 3009143 | A1 | | 7/2017 | |
| CA | 2921709 | A1 | | 8/2017 | |
| CA | 3019528 | A1 | | 10/2017 | |
| CA | 2625286 | C | | 11/2017 | |
| CA | 2804068 | C | | 11/2017 | |
| CA | 2809419 | C | | 11/2017 | |
| CA | 2966817 | A1 | | 11/2017 | |
| CA | 3026146 | A1 | | 12/2017 | |
| CA | 3026379 | A1 | | 12/2017 | |
| CA | 2976874 | A1 | | 2/2018 | |
| CA | 2859140 | C | | 4/2018 | |
| CA | 3032714 | A1 | | 4/2018 | |
| CA | 2764045 | C | | 5/2018 | |
| CA | 2817135 | C | | 5/2018 | |
| CA | 2947079 | A1 | | 5/2018 | |
| CA | 3046342 | A1 | | 6/2018 | |
| CA | 2853284 | C | | 8/2018 | |
| CA | 2994589 | A1 | | 8/2018 | |
| CA | 2963648 | A1 | | 10/2018 | |
| CA | 3002086 | A1 | | 10/2018 | |
| CA | 3060412 | A1 | | 10/2018 | |
| CA | 3061928 | A1 | | 11/2018 | |
| CA | 3009858 | A1 | | 12/2018 | |
| CA | 3063741 | A1 | | 12/2018 | |
| CA | 3064886 | A1 | * | 12/2018 | |
| CA | 2827187 | C | | 1/2019 | |
| CA | 2844108 | C | | 1/2019 | |
| CA | 2895089 | C | | 2/2019 | |
| CA | 2949211 | C | | 2/2019 | |
| CA | 2953117 | C | | 2/2019 | |
| CA | 3013693 | A1 | | 2/2019 | |
| CA | 3056670 | A1 | | 2/2019 | |
| CA | 2890523 | C | | 4/2019 | |
| CA | 2918683 | C | | 4/2019 | |
| CA | 3020553 | A1 | | 4/2019 | |
| CA | 3024061 | A1 | | 5/2019 | |
| CA | 3030730 | A1 | | 7/2019 | |
| CA | 2993966 | A1 | | 8/2019 | |
| CA | 2788495 | C | | 9/2019 | |
| CA | 2872239 | C | | 9/2019 | |
| CA | 3004073 | A1 | | 11/2019 | |
| CA | 2943993 | C | | 2/2020 | |
| CA | 2907132 | C | | 6/2020 | |
| CA | 2863441 | C | | 7/2020 | |
| CA | 2877128 | C | | 7/2020 | |
| CA | 2841288 | C | | 10/2020 | |
| CA | 2956623 | C | | 10/2020 | |
| CA | 2929504 | C | | 11/2020 | |
| CN | 103629783 | A | * | 3/2014 | |
| CN | 106585317 | A | * | 4/2017 | |
| CN | 107379919 | A | * | 11/2017 | |
| CN | 108318081 | A | * | 7/2018 | ............ G01D 21/02 |
| CN | 108519463 | A | * | 9/2018 | |
| CN | 207923830 | U | * | 9/2018 | |
| CN | 209979592 | U | * | 1/2020 | |
| CN | 210051754 | U | * | 2/2020 | |
| CN | 215493007 | U | * | 1/2022 | |
| CN | 217954383 | U | * | 12/2022 | |
| CN | 115684080 | A | * | 2/2023 | |
| FR | 3105105 | A1 | * | 6/2021 | |
| FR | 3111098 | A1 | * | 12/2021 | |
| MX | PA01013256 | A | | 7/2002 | |
| MX | PA02004467 | A | | 9/2002 | |
| MX | PA02004618 | A | | 9/2002 | |
| MX | PA03005234 | A | | 11/2003 | |
| MX | PA02001134 | A | | 4/2004 | |
| MX | PA03009556 | A | | 12/2004 | |
| MX | PA04011283 | A | | 2/2005 | |
| MX | PA03009997 | A | | 4/2005 | |
| MX | PA03007340 | A | | 10/2005 | |
| MX | PA04007528 | A | | 1/2006 | |
| MX | PA06003733 | A | | 6/2006 | |
| MX | 2011001916 | A | | 8/2011 | |
| MX | 2012002602 | A | | 7/2012 | |
| MX | 2011013405 | A | | 10/2012 | |
| MX | 2014009852 | A | | 10/2014 | |
| MX | 2014012086 | A | | 11/2014 | |
| MX | 2015004232 | A | | 6/2015 | |
| MX | 2015001896 | A | | 8/2015 | |
| MX | 2015003835 | A | | 2/2016 | |
| MX | 338943 | B | | 5/2016 | |
| MX | 2015017943 | A | | 5/2016 | |
| MX | 340191 | B | | 6/2016 | |
| MX | 2016006252 | A | | 2/2017 | |
| MX | 2017001652 | A | | 4/2017 | |
| MX | 347634 | B | | 5/2017 | |
| MX | 350020 | B | | 8/2017 | |
| MX | 350527 | B | | 9/2017 | |
| MX | 2017015691 | A | | 4/2018 | |
| MX | 2017006324 | A | | 8/2018 | |
| MX | 2018001801 | A | | 11/2018 | |
| MX | 361392 | B | | 12/2018 | |
| MX | 2018014848 | A | | 4/2019 | |
| MX | 365571 | B | | 5/2019 | |
| MX | 2017015162 | A | | 5/2019 | |
| MX | 2019002299 | A | | 7/2019 | |
| TW | 202207174 | A | * | 2/2022 | |
| WO | WO-2017005084 | A1 | * | 1/2017 | .............. B60H 1/22 |
| WO | WO-2017138873 | A1 | | 8/2017 | |
| WO | WO-2017165220 | A1 | | 9/2017 | |
| WO | WO-2017186519 | A1 | | 11/2017 | |
| WO | WO-2017189747 | A1 | | 11/2017 | |
| WO | WO-2017203131 | A1 | | 11/2017 | |
| WO | WO-2017211521 | A1 | | 12/2017 | |
| WO | WO-2017216440 | A1 | | 12/2017 | |
| WO | WO-2017216496 | A1 | | 12/2017 | |
| WO | WO-2018013039 | A1 | | 1/2018 | |
| WO | WO-2018013764 | A1 | | 1/2018 | |
| WO | WO-2018029230 | A1 | | 2/2018 | |
| WO | WO-2018035540 | A1 | | 2/2018 | |
| WO | WO-2018041502 | A1 | | 3/2018 | |
| WO | WO-2018041637 | A1 | | 3/2018 | |
| WO | WO-2018046037 | A1 | | 3/2018 | |
| WO | WO-2018046845 | A1 | | 3/2018 | |
| WO | WO-2018054912 | A1 | | 3/2018 | |
| WO | WO-2018065141 | A1 | | 4/2018 | |
| WO | WO-2018084039 | A1 | | 5/2018 | |
| WO | WO-2018084830 | A1 | * | 5/2018 | |
| WO | WO-2018096894 | A1 | | 5/2018 | |
| WO | WO-2018097246 | A1 | | 5/2018 | |
| WO | WO-2018102583 | A1 | | 6/2018 | |
| WO | WO-2018104425 | A1 | | 6/2018 | |

(56) References Cited

FOREIGN PATENT DOCUMENTS

WO WO-2018111761 A1 6/2018
WO WO-2018115620 A1 6/2018
WO WO-2018122556 A1 7/2018
WO WO-2018128272 A1 7/2018
WO WO-2018132007 A1 7/2018
WO WO-2018132560 A1 7/2018
WO WO-2018132746 A1 7/2018
WO WO-2018133302 A1 7/2018
WO WO-2018135550 A1 7/2018
WO WO-2018136263 A1 7/2018
WO WO-2018139899 A1 8/2018
WO WO-2018140330 A1 8/2018
WO WO-2018141620 A1 8/2018
WO WO-2018142162 A1 8/2018
WO WO-2018142961 A1 8/2018
WO WO-2018143256 A1 8/2018
WO WO-2018145706 A1 8/2018
WO WO-2018148740 A1 8/2018
WO WO-2018154567 A1 8/2018
WO WO-2018154614 A2 8/2018
WO WO-2018155260 A1 8/2018
WO WO-2018156001 A1 8/2018
WO WO-2018156002 A1 8/2018
WO WO-2018156003 A1 8/2018
WO WO-2018158083 A1 9/2018
WO WO-2018159164 A1 9/2018
WO WO-2018159165 A1 9/2018
WO WO-2018159518 A1 9/2018
WO WO-2018160668 A1 9/2018
WO WO-2018160835 A1 9/2018
WO WO-2018162638 A1 9/2018
WO WO-2018168672 A1 9/2018
WO WO-2018170154 A1 9/2018
WO WO-2018170187 A1 9/2018
WO WO-2018173060 A1 9/2018
WO WO-2018174823 A1 9/2018
WO WO-2018177699 A1 10/2018
WO WO-2018182037 A1 10/2018
WO WO-2018182323 A1 10/2018
WO WO-2018182324 A1 10/2018
WO WO-2018183215 A1 10/2018
WO WO-2018183506 A1 10/2018
WO WO-2018183675 A1 10/2018
WO WO-2018184162 A1 10/2018
WO WO-2018187266 A1 10/2018
WO WO-2018188941 A1 10/2018
WO WO-2018189926 A1 10/2018
WO WO-2018190003 A1 10/2018
WO WO-2018191044 A1 10/2018
WO WO-2018191688 A2 10/2018
WO WO-2018191699 A1 10/2018
WO WO-2018191716 A1 10/2018
WO WO-2018194650 A1 10/2018
WO WO-2018194943 A1 10/2018
WO WO-2018198869 A1 11/2018
WO WO-2018201135 A1 11/2018
WO WO-2018202004 A1 11/2018
WO WO-2018202416 A1 11/2018
WO WO-2018202975 A2 11/2018
WO WO-2018202977 A2 11/2018
WO WO-2018206385 A1 11/2018
WO WO-2018207879 A1 11/2018
WO WO-2018207997 A1 11/2018
WO WO-2018209943 A1 11/2018
WO WO-2018211126 A1 11/2018
WO WO-2018211642 A1 11/2018
WO WO-2018212423 A1 11/2018
WO WO-2018213435 A1 11/2018
WO WO-2018214861 A1 11/2018
WO WO-2018215220 A1 11/2018
WO WO-2018215430 A1 11/2018
WO WO-2018215505 A1 11/2018
WO WO-2018216192 A1 11/2018
WO WO-2018216848 A1 11/2018
WO WO-2018218090 A1 11/2018
WO WO-2018218868 A1 12/2018
WO WO-2018218869 A1 12/2018
WO WO-2018218870 A1 12/2018
WO WO-2018220830 A1 12/2018
WO WO-2018221889 A1 12/2018
WO WO-2018222789 A1 12/2018
WO WO-2018222905 A1 12/2018
WO WO-2018222980 A1 12/2018
WO WO-2018224373 A1 12/2018
WO WO-2018225058 A1 12/2018
WO WO-2018230766 A1 12/2018
WO WO-2018231850 A1 12/2018
WO WO-2018235073 A1 12/2018
WO WO-2018235148 A1 12/2018
WO WO-2018236026 A1 12/2018
WO WO-2019003181 A1 1/2019
WO WO-2019006584 A1 1/2019
WO WO-2019008089 A1 1/2019
WO WO-2019021275 A1 1/2019
WO WO-2019023294 A1 1/2019
WO WO-2019025662 A1 2/2019
WO WO-2019025769 A1 2/2019
WO WO-2019027328 A1 2/2019
WO WO-2019027701 A1 2/2019
WO WO-2019028106 A1 2/2019
WO WO-2019028429 A1 2/2019
WO WO-2019032336 A1 2/2019
WO WO-2019034606 A1 2/2019
WO WO-2019034949 A1 2/2019
WO WO-2019035476 A1 2/2019
WO WO-2019035950 A1 2/2019
WO WO-2019036889 A1 2/2019
WO WO-2019036958 A1 2/2019
WO WO-2019037665 A1 2/2019
WO WO-2019037983 A1 2/2019
WO WO-2019040002 A1 2/2019
WO WO-2019040937 A1 2/2019
WO WO-2019041488 A1 3/2019
WO WO-2019046182 A1 3/2019
WO WO-2019046970 A1 3/2019
WO WO-2019051826 A1 3/2019
WO WO-2019051893 A1 3/2019
WO WO-2019052037 A1 3/2019
WO WO-2019053259 A1 3/2019
WO WO-2019053700 A2 3/2019
WO WO-2019054649 A1 3/2019
WO WO-2019054650 A1 3/2019
WO WO-2019055876 A2 3/2019
WO WO-2019056159 A1 3/2019
WO WO-2019056323 A1 3/2019
WO WO-2019059276 A1 3/2019
WO WO-2019060950 A1 4/2019
WO WO-2019061825 A1 4/2019
WO WO-2019067454 A1 4/2019
WO WO-2019068851 A1 4/2019
WO WO-2019069893 A1 4/2019
WO WO-2019072352 A2 4/2019
WO WO-2019072730 A1 4/2019
WO WO-2019073280 A1 4/2019
WO WO-2019074526 A1 4/2019
WO WO-2019075110 A1 4/2019
WO WO-2019075365 A1 4/2019
WO WO-2019076418 A1 4/2019
WO WO-2019077478 A1 4/2019
WO WO-2019077558 A1 4/2019
WO WO-2019079039 A1 4/2019
WO WO-2019080784 A1 5/2019
WO WO-2019082836 A1 5/2019
WO WO-2019085369 A1 5/2019
WO WO-2019086082 A1 5/2019
WO WO-2019088839 A1 5/2019
WO WO-2019090549 A1 5/2019
WO WO-2019093162 A1 5/2019
WO WO-2019095790 A1 5/2019
WO WO-2019096568 A1 5/2019
WO WO-2019097534 A1 5/2019
WO WO-2019097634 A1 5/2019
WO WO-2019098432 A1 5/2019
WO WO-2019098977 A2 5/2019

(56) References Cited

FOREIGN PATENT DOCUMENTS

WO WO-2019099387 A1 5/2019
WO WO-2019099425 A1 5/2019
WO WO-2019099431 A1 5/2019
WO WO-2019101812 A2 5/2019
WO WO-2019102654 A1 5/2019
WO WO-2019102660 A1 5/2019
WO WO-2019104130 A1 5/2019
WO WO-2019105859 A1 6/2019
WO WO-2019106379 A2 6/2019
WO WO-2019107370 A1 6/2019
WO WO-2019107965 A1 6/2019
WO WO-2019110155 A1 6/2019
WO WO-2019111262 A1 6/2019
WO WO-2019111471 A1 6/2019
WO WO-2019111850 A1 6/2019
WO WO-2019114052 A1 6/2019
WO WO-2019116543 A1 6/2019
WO WO-2019117321 A1 6/2019
WO WO-2019122889 A1 6/2019
WO WO-2019123864 A1 6/2019
WO WO-2019123865 A1 6/2019
WO WO-2019124625 A1 6/2019
WO WO-2019124993 A1 6/2019
WO WO-2019126181 A1 6/2019
WO WO-2019126811 A1 6/2019
WO WO-2019128203 A1 7/2019
WO WO-2019129028 A1 7/2019
WO WO-2019130255 A1 7/2019
WO WO-2019131789 A1 7/2019
WO WO-2019132269 A1 7/2019
WO WO-2019134955 A1 7/2019
WO WO-2019136110 A1 7/2019
WO WO-2019137604 A1 7/2019
WO WO-2019140543 A1 7/2019
WO WO-2019146971 A1 8/2019
WO WO-2019147537 A1 8/2019
WO WO-2019149230 A1 8/2019
WO WO-2019149231 A1 8/2019
WO WO-2019149232 A1 8/2019
WO WO-2019149233 A1 8/2019
WO WO-2019149234 A1 8/2019
WO WO-2019149235 A1 8/2019
WO WO-2019150182 A1 8/2019
WO WO-2019150735 A1 8/2019
WO WO-2019152047 A1 8/2019
WO WO-2019152832 A1 8/2019
WO WO-2019156229 A1 8/2019
WO WO-2019157302 A1 8/2019
WO WO-2019157784 A1 8/2019
WO WO-2019158433 A1 8/2019
WO WO-2019162949 A1 8/2019
WO WO-2019162960 A1 8/2019
WO WO-2019163966 A1 8/2019
WO WO-2019165422 A1 8/2019
WO WO-2019168427 A1 9/2019
WO WO-2019169803 A1 9/2019
WO WO-2019172251 A1 9/2019
WO WO-2019172859 A1 9/2019
WO WO-2019179699 A1 9/2019
WO WO-2019180985 A1 9/2019
WO WO-2019182114 A1 9/2019
WO WO-2019185107 A1 10/2019
WO WO-2019185764 A1 10/2019
WO WO-2019186527 A1 10/2019
WO WO-2019187671 A1 10/2019
WO WO-2019188408 A1 10/2019
WO WO-2019189128 A1 10/2019
WO WO-2019189964 A1 10/2019
WO WO-2019195764 A1 10/2019
WO WO-2019198648 A1 10/2019
WO WO-2019200021 A1 10/2019
WO WO-2019204779 A1 10/2019
WO WO-2019204785 A1 10/2019
WO WO-2019204788 A1 10/2019
WO WO-2019204789 A1 10/2019
WO WO-2019204790 A1 10/2019
WO WO-2019206541 A1 10/2019
WO WO-2019206610 A1 10/2019
WO WO-2019207888 A1 10/2019
WO WO-2019210718 A1 11/2019
WO WO-2019210719 A1 11/2019
WO WO-2019210720 A1 11/2019
WO WO-2019213280 A1 11/2019
WO WO-2019213439 A1 11/2019
WO WO-2019213998 A1 11/2019
WO WO-2019214433 A1 11/2019
WO WO-2019214821 A1 11/2019
WO WO-2019216755 A1 11/2019
WO WO-2019217191 A1 11/2019
WO WO-2019217267 A1 11/2019
WO WO-2019218395 A1 11/2019
WO WO-2019222202 A1 11/2019
WO WO-2019222964 A1 11/2019
WO WO-2019224542 A1 11/2019
WO WO-2019224628 A1 11/2019
WO WO-2019224865 A1 11/2019
WO WO-2019225894 A1 11/2019
WO WO-2019226357 A1 11/2019
WO WO-2019227388 A1 12/2019
WO WO-2019228617 A1 12/2019
WO WO-2019231199 A1 12/2019
WO WO-2019232014 A1 12/2019
WO WO-2019234978 A1 12/2019
WO WO-2019236032 A2 12/2019
WO WO-2019236974 A1 12/2019
WO WO-2019239025 A1 12/2019
WO WO-2019239360 A1 12/2019
WO WO-2019239855 A1 12/2019
WO WO-2019240100 A1 12/2019
WO WO-2019241126 A1 12/2019
WO WO-2019243361 A1 12/2019
WO WO-2020002667 A1 1/2020
WO WO-2020003532 A1 1/2020
WO WO-2020004959 A1 1/2020
WO WO-2020005874 A1 1/2020
WO WO-2020010026 A1 1/2020
WO WO-2020010921 A1 1/2020
WO WO-2020012002 A1 1/2020
WO WO-2020012162 A1 1/2020
WO WO-2020012800 A1 1/2020
WO WO-2020174462 A1 * 9/2020 ........... B60H 1/0073
WO WO-2022023958 A1 * 2/2022
WO WO-2022105899 A1 * 5/2022

* cited by examiner

| Measurement combination | Diagnosis |
|---|---|
| Measured odor (VOCs) is characteristic of domestic pets. PM sensor sees increase in concentration of particles sized 2.5-10μm | Pet(s) in passenger cabin |
| Measured odor (VOCs) is characteristic of cigarette smoke. PM sensor sees increase in concentration of particles sized 4μm and smaller. | Cigarette smoking in passenger cabin |
| Measured odor (VOCs) is characteristic of marijuana smoke. PM sensor sees increase in concentration of particles sized 4μm and smaller. | Marijuana smoking in passenger cabin |

FIG. 7

| Measurement combination | Diagnosis |
| --- | --- |
| Smell (VOC) profile matches nitric oxide (PM may be irrelevant) | catalytic converter issue |
| Measured smell (VOC) matches profile of heated/vaporized ethyl glycol (PM may be irrelevant) | Engine coolant leak |
| Smell (VOC) profile matches profile of heated/vaporized engine oil. PM sensor sees increase in concentration of particles <1μm. | Engine oil leak |
| Measured smell (VOC) matches profile of overheated/melting EPDM/poly/etc. (PM may be irrelevant) | belt or hose rubbing |
| Measured smell (VOC) matches profile of overheated clutch (PM may be irrelevant) | Overheating clutch |
| Measured smell (VOC) matches profile of overheated brake pads/brake fluid/etc. (PM may be irrelevant) | Brake issue |
| Measured smell (VOC) matches profile of overheated overloaded vehicle, battery failure/fault. (PM may be irrelevant) | Overloaded vehicle, battery failure/fault |

FIG. 8

| Measurement combination | Remaining oil life |
|---|---|
| Nodes 10-20 = Average 2.50<br>Nodes 20-32 = Average 4.50<br>Nodes 45-55 = Average 7.00 | 85 percent |
| Nodes 10-20 = Average 2.75<br>Nodes 20-32 = Average 4.75<br>Nodes 45-55 = Average 7.00 | 75 percent |
| Nodes 10-20 = Average 3.00<br>Nodes 20-32 = Average 5.00<br>Nodes 45-55 = Average 7.25 | 50 percent |
| Nodes 10-20 = Average 3.50<br>Nodes 20-32 = Average 5.50<br>Nodes 45-55 = Average 7.50 | 35 percent |
| Nodes 10-20 = Average 3.75<br>Nodes 20-32 = Average 5.75<br>Nodes 45-55 = Average 7.50 | 25 percent |
| Nodes 10-20 = Average 4.00<br>Nodes 20-32 = Average 6.00<br>Nodes 45-55 = Average 7.75 | 10 percent |
| . . . | . . . |

FIG. 10

FIG. 12
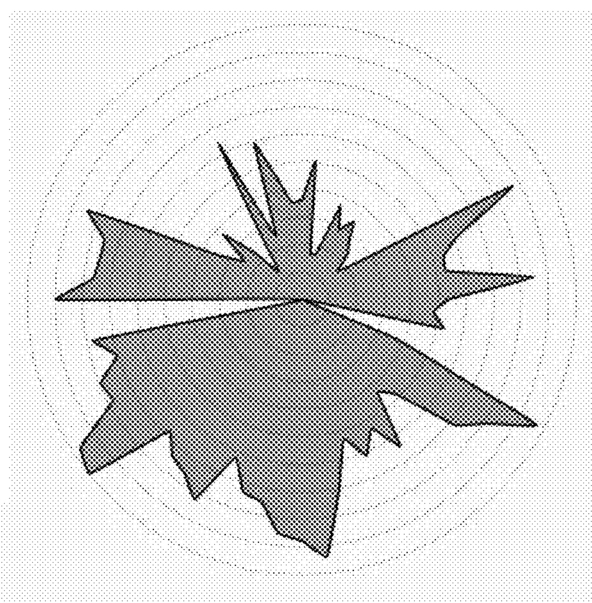
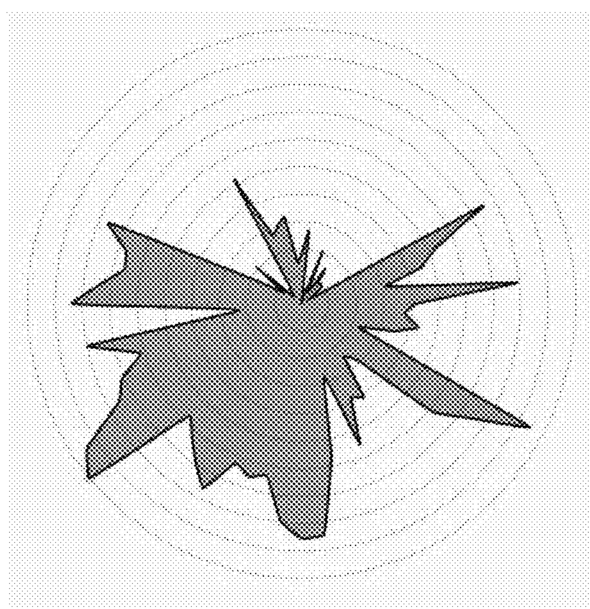
FIG. 11

DIAGNOSTIC SYSTEMS AND METHODS OF VEHICLES USING OLFACTION

CROSS-REFERENCE TO RELATED APPLICATIONS

This application claims the benefit of U.S. Provisional Application No. 63/067,922, filed on Aug. 20, 2020. The entire disclosure of the application referenced above is incorporated herein by reference.

FIELD

The present disclosure relates to vehicles and more particularly to diagnostic systems and methods using olfaction sensors.

BACKGROUND

This section provides background information related to the present disclosure which is not necessarily prior art.

Vehicles have been recalled due to carbon monoxide entering their passenger cabins and for other reasons. Humans may be overcome by carbon monoxide and lose consciousness.

There may be numerous other situations where chemicals could be present within a passenger cabin of a vehicle. For example, a user may bring an aerosol can in to the passenger cabin of a vehicle and forget to take it out. Due to heat or cold, the aerosol can could emit its contents into the passenger cabin. One or more users could enter the vehicle later and breathe the contents without knowledge.

Electric vehicles include one or more batteries that contain chemicals, such as lithium. The batteries may be located under the passenger cabin and, under some circumstances, can rupture and emit chemicals. Some chemicals that may be present within a passenger cabin of a vehicle may be odorless and colorless.

SUMMARY

In a feature, a vehicle system is described and includes: at least one of: a particulate matter sensor configured to measure an amount of particulate within a passenger cabin of a vehicle; and a volatile organic compounds (VOC) sensor configured to measure an amount of VOCs within the passenger cabin of the vehicle; and a control module configured to, based on at least one of the amount of particulate and the amount of VOCs within the passenger cabin of the vehicle, diagnose at least one of: a characteristic of the vehicle; presence of a chemical in the passenger cabin of the vehicle; occurrence of an event within the passenger cabin of the vehicle; and a remaining life of engine oil of the vehicle.

In further features, the control module is configured to store the diagnosis in memory of the vehicle.

In further features, the control module is configured to transmit the diagnosis to a remote device.

In further features, the control module is configured to transmit the diagnosis to the remote device via a wireless transceiver of the vehicle.

In further features, the control module is configured to transmit the diagnosis to the remote device via a wired connection between the remote device and a port of the vehicle.

In further features, the control module is configured to, based on the at least one of the amount of particulate and the amount of VOCs within the passenger cabin of the vehicle, diagnose a characteristic of the vehicle.

In further features, the characteristic includes a fault of a catalytic converter.

In further features, the characteristic includes an engine coolant leak.

In further features, the characteristic includes an engine oil leak.

In further features, the characteristic includes rubbing of a belt or a hose.

In further features, the characteristic includes overheating of a clutch.

In further features, the characteristic includes a fault associated with one or more brakes.

In further features, the characteristic includes overloading of the vehicle.

In further features, the characteristic includes a fault associated with a battery of the vehicle.

In further features, the control module is configured to make the diagnosis further based on at least one of a baseline amount of particulate from before the diagnosis and a baseline amount of VOCs within the passenger cabin of the vehicle from before the diagnosis.

In further features, the control module is configured to, based on the at least one of the amount of particulate and the amount of VOCs within the passenger cabin of the vehicle, diagnose the occurrence of an event within a passenger cabin of the vehicle.

In further features, the event is one of smoking, presence of an animal, and presence of food.

In further features, the control module is configured to, based on the at least one of the amount of particulate and the amount of VOCs within the passenger cabin of the vehicle, diagnose the presence of a chemical in the passenger cabin of the vehicle.

In further features, the control module is configured to, based on the at least one of the amount of particulate and the amount of VOCs within the passenger cabin of the vehicle, diagnose the remaining life of engine oil of the vehicle.

In a feature, a method is disclosed and includes: at least one of: measuring an amount of particulate within a passenger cabin of a vehicle; and measuring an amount of a volatile organic compounds (VOCs) within the passenger cabin of the vehicle; and based on at least one of the amount of particulate and the amount of VOCs within the passenger cabin of the vehicle, diagnosing at least one of: a characteristic of the vehicle; presence of a chemical in the passenger cabin of the vehicle; occurrence of an event within the passenger cabin of the vehicle; and a remaining life of engine oil of the vehicle.

Further areas of applicability of the present disclosure will become apparent from the detailed description, the claims and the drawings. The detailed description and specific examples are intended for purposes of illustration only and are not intended to limit the scope of the disclosure.

DRAWINGS

The drawings described herein are for illustrative purposes only of selected embodiments and not all possible implementations, and are not intended to limit the scope of the present disclosure.

Figure 3:
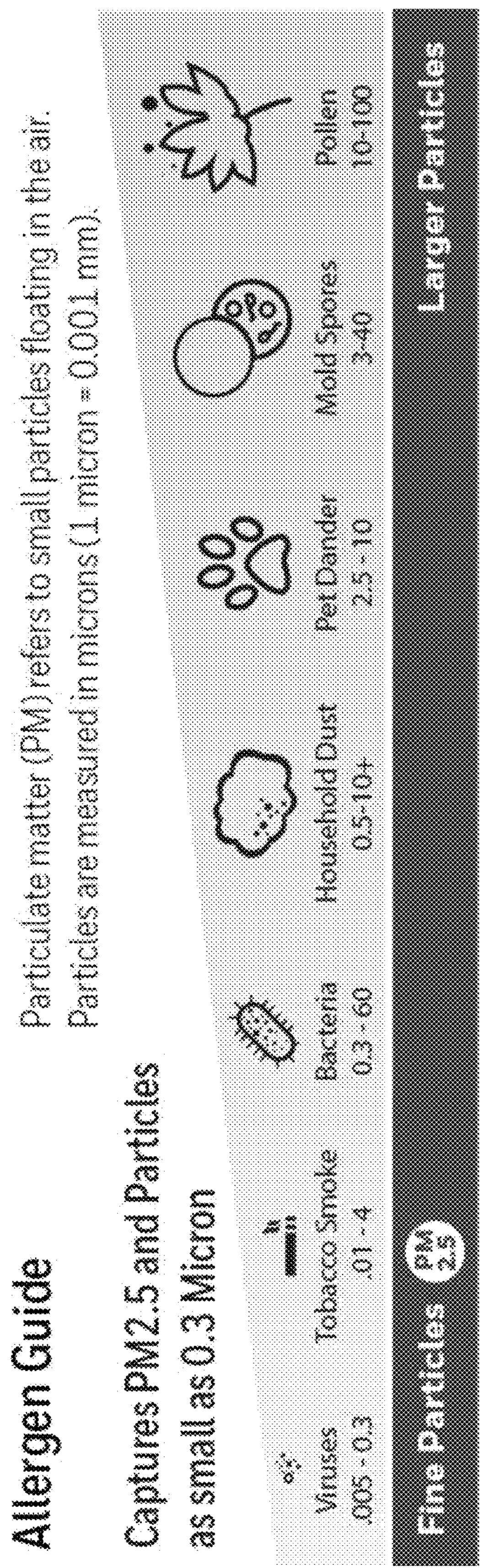
Figure 4:
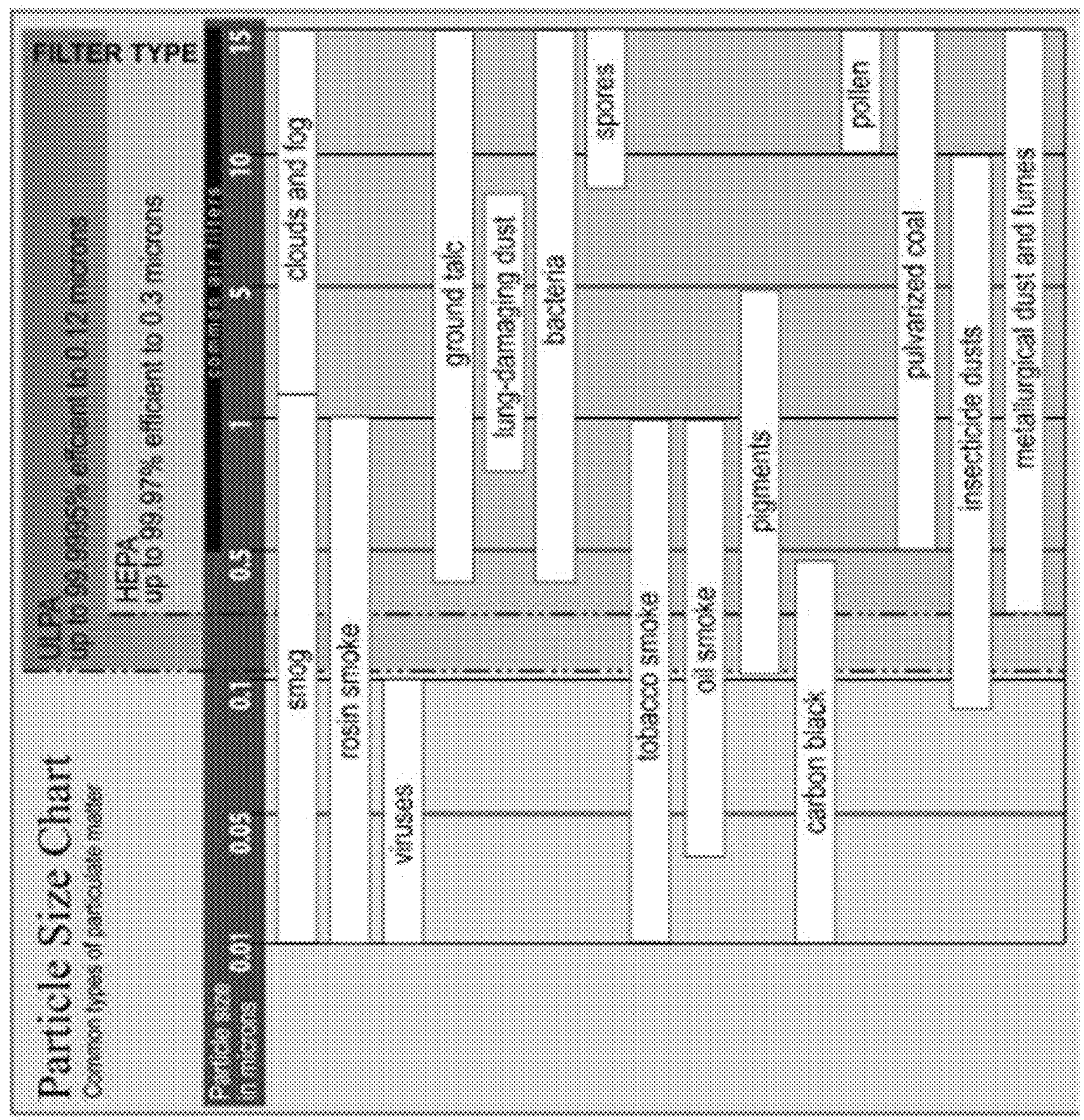

FIGS. 3 and 4 include example illustrations of how different airborne items vary by size for various types of particulates.

Figure 5:
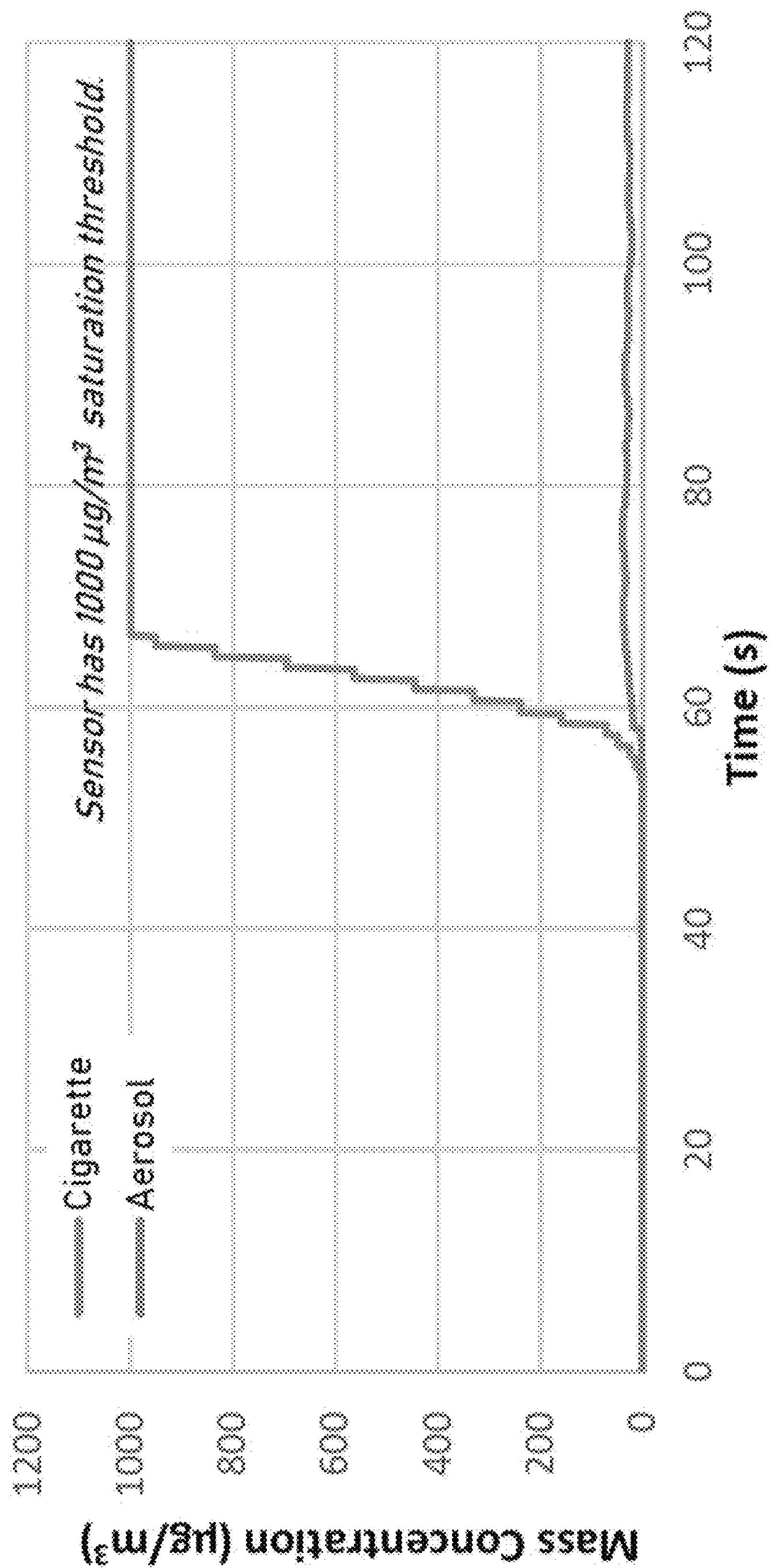

FIG. 5 includes example graphs illustrating cigarette smoking and aerosol particulate profiles over time.

Figure 6:
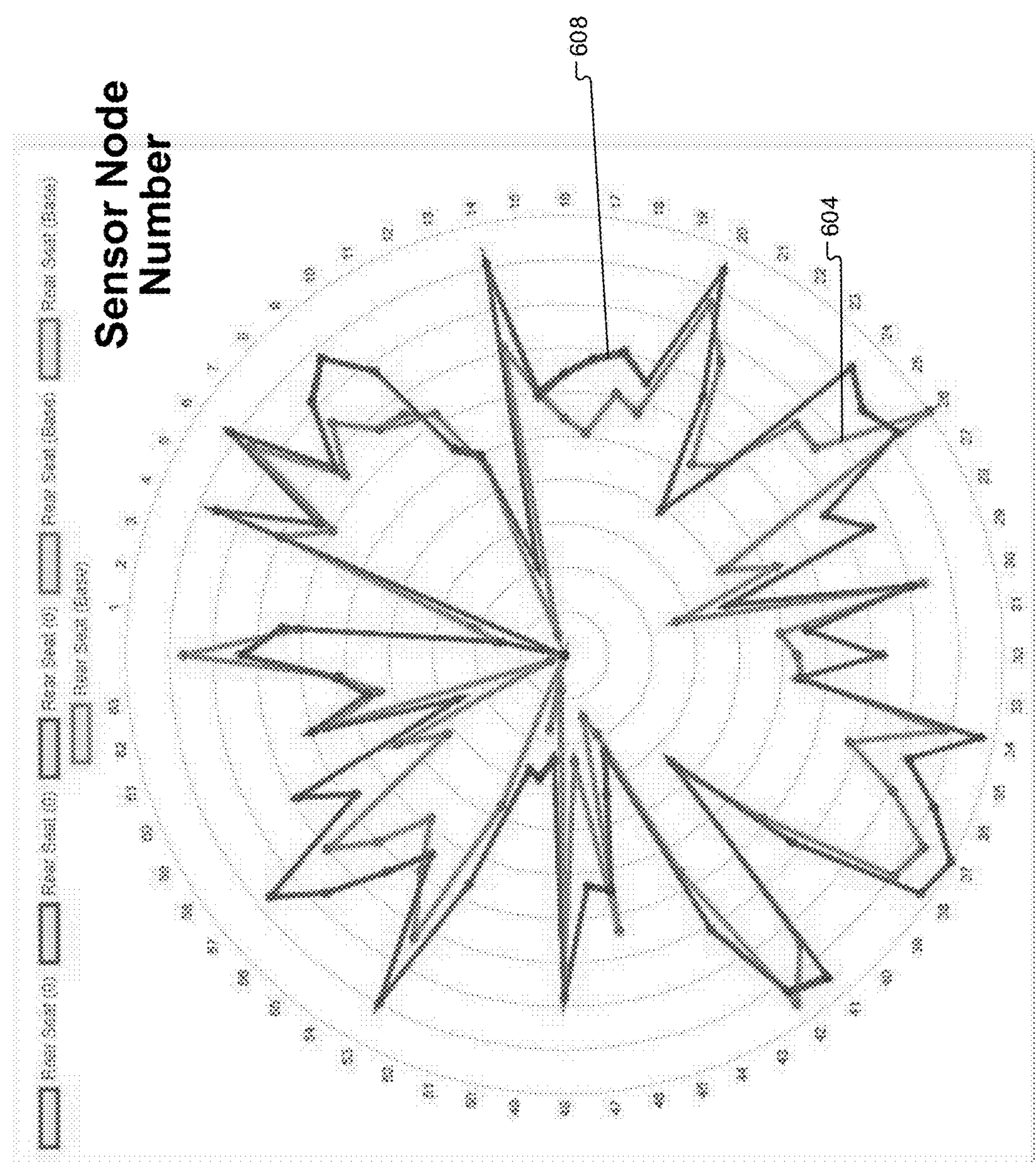

FIG. 6 includes an example radius graph at various sensor nodes of VOCs and particulate measured at a seat at the corresponding times.

FIG. 7 includes an example table including conditions that may be associated with different types of events within the passenger cabin.

FIG. 8 includes an example table including conditions that may be associated with different types of vehicle characteristics.

Figure 9:
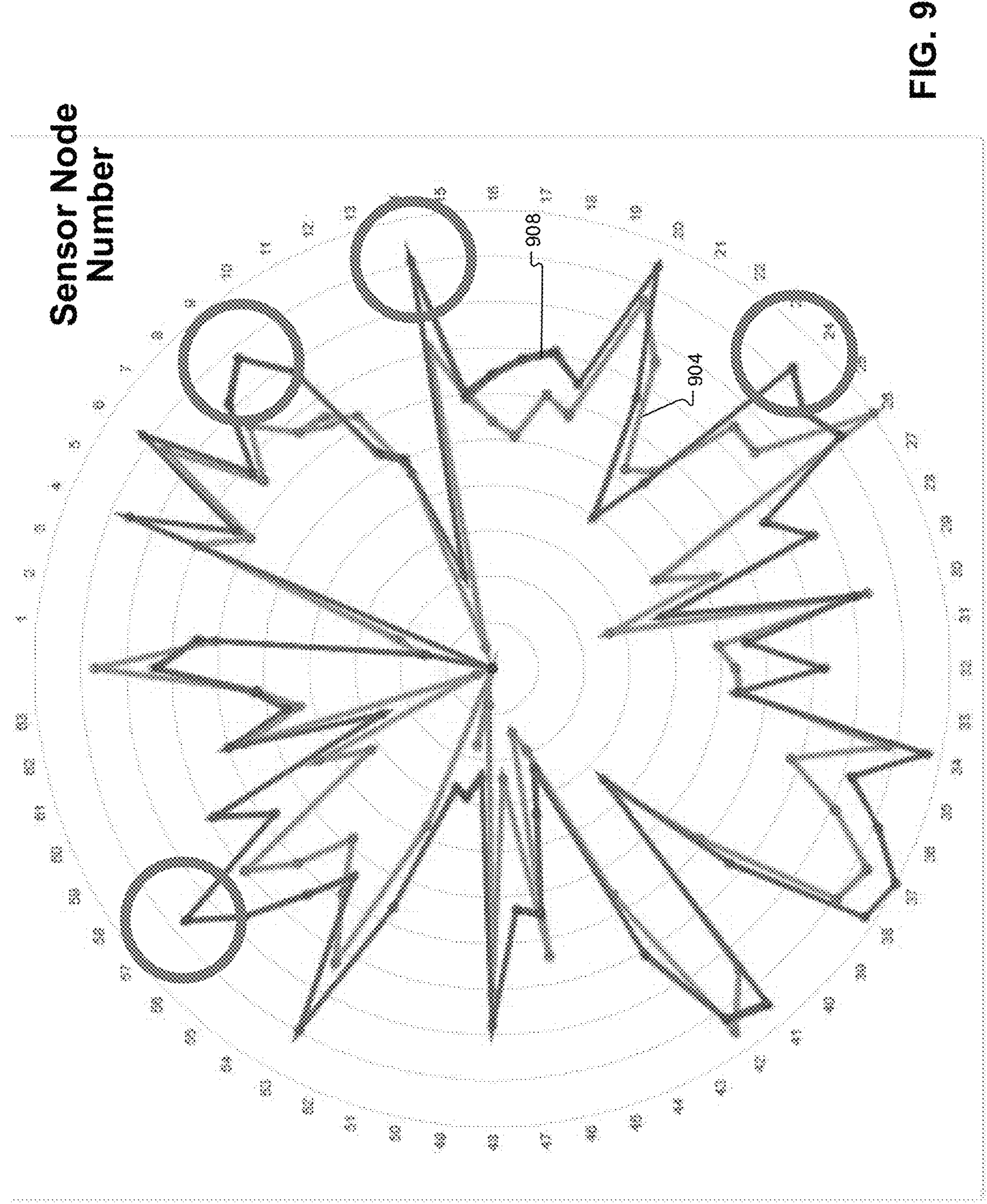

FIG. 9 includes an example radius graph of magnitudes of one or more different measurements/nodes measured at a seat.

FIG. 10 includes an example table including measurements associated with different oil characteristics.

FIGS. 11 and 12 include example graphs for 85% remaining oil life and 10% remaining oil life, respectively.

Figure 13:
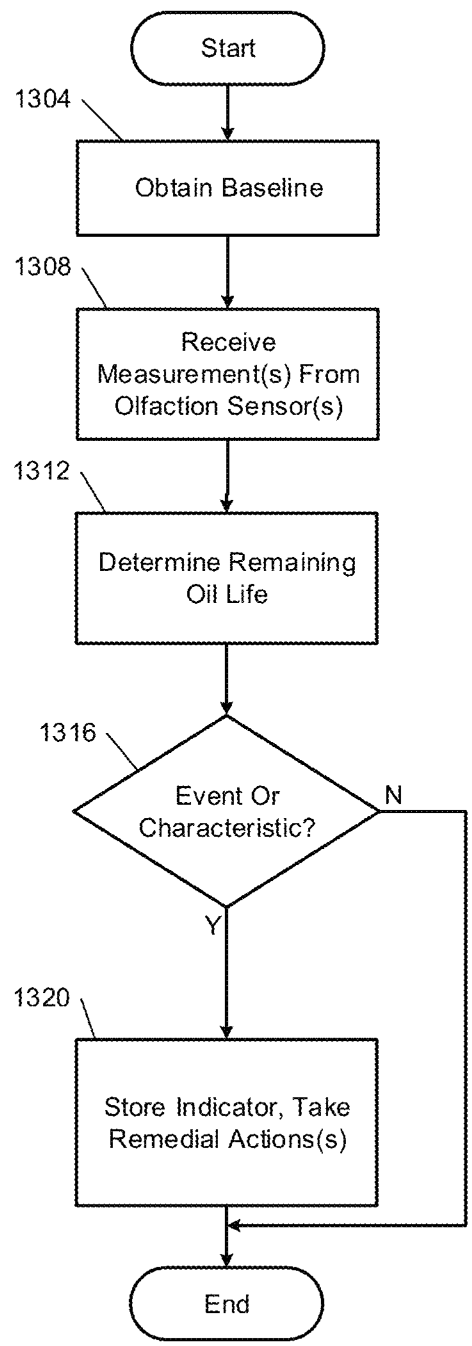

FIG. 13 is a flowchart depicting an example method of diagnosing conditions and events within a passenger cabin of a vehicle.

Corresponding reference numerals indicate corresponding parts throughout the several views of the drawings.

DETAILED DESCRIPTION

Example embodiments will now be described more fully with reference to the accompanying drawings.

Figure 1:
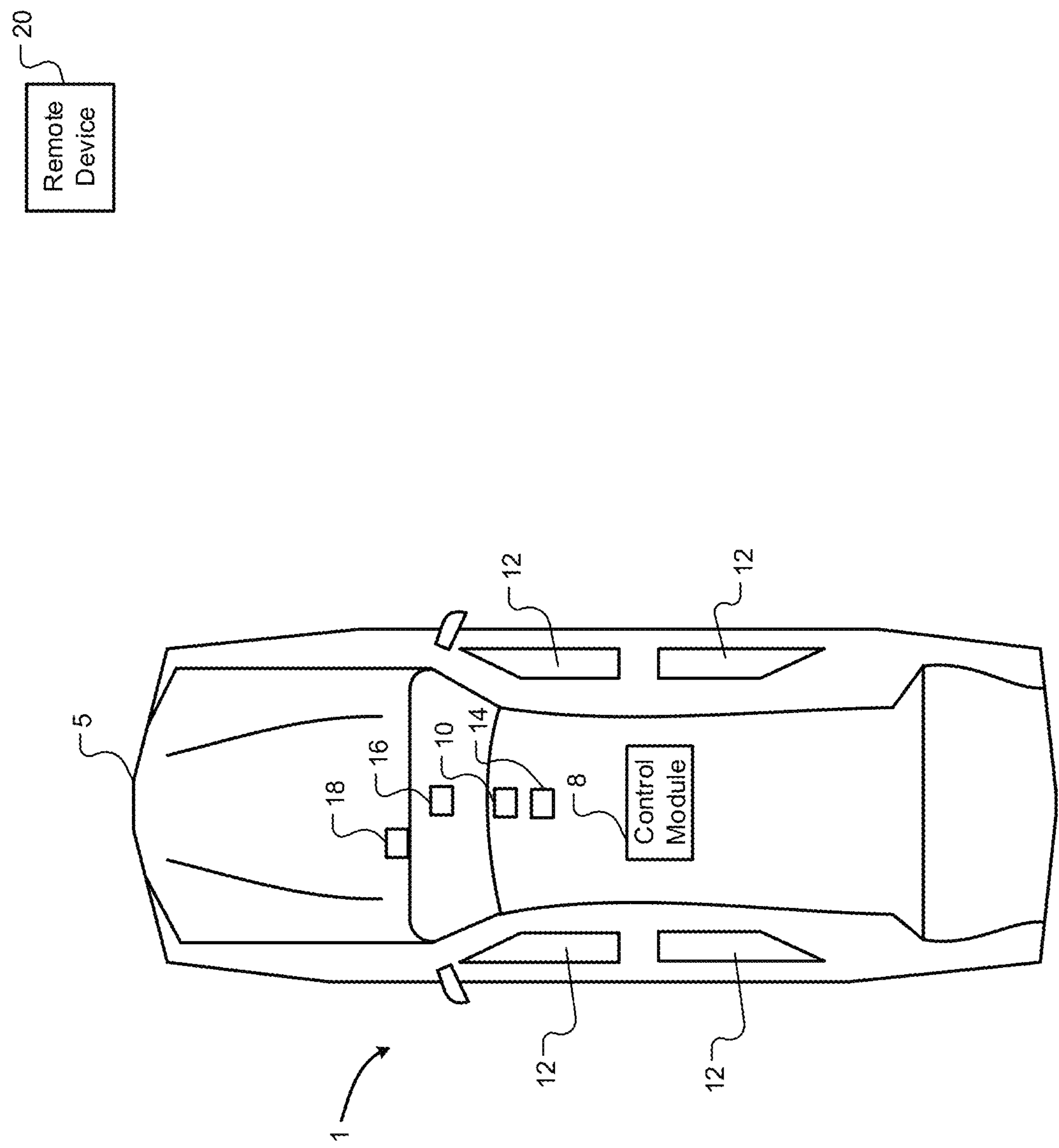
FIG. 1 is a functional block diagram of an example vehicle system.

FIG. 1 includes a functional block diagram including an example vehicle 5. The vehicle 5 includes a control module 8 and one or more olfaction sensors, such as olfaction sensor 10. Examples of olfaction sensors in vehicles include, for example, particulate matter sensors, carbon monoxide (or other carbon oxide) sensors, volatile organic compound (VOC) sensors, and other types of sensors. The vehicle 5 may include one or more different types of olfaction sensors.

The olfaction sensor(s) are each configured to measure an amount of one or more chemical within a passenger cabin of the vehicle 5. For example, the vehicle 5 may include a particulate matter sensor configured to measure one or more amounts (e.g., concentrations or mass flow rates) of particulate of one or more different sizes in air within the passenger cabin. Additionally or alternatively, the vehicle 5 may include a carbon monoxide sensor configured to measure an amount (e.g., concentration) of carbon monoxide in air within the passenger cabin. Additionally or alternatively, the vehicle 5 may include a VOC sensor configured to measure an amount (e.g., concentration) of VOCs within the passenger cabin.

The control module 8 may receive the measurements from the olfaction sensor(s) and take one or more remedial actions based on the measurements. For example, when one or more amount of one or more chemicals (e.g., particulate, carbon monoxide, VOCs) measured by one or more olfaction sensors is/are greater than one or more respective predetermined amount/s (e.g., of particulate matter, carbon monoxide, or VOCs, respectively), the control module 8 may take one or more remedial actions. The predetermined amount/s is/are greater than zero.

For example, the control module 8 may open one or more windows 12 of the vehicle 5 when the amount of a chemical is greater than the predetermined amount. Additionally or alternatively, the control module 8 may generate an alert within the vehicle 5 when the amount of a chemical is greater than the predetermined amount. For example, the control module 8 may generate or display a visual alert, such as via a visual indicator 14 that is visible within the passenger cabin of the vehicle 5. The visual indicator 14 may be, for example, one or more indicator lights, a display, or another suitable type of visual indicator. Additionally or alternatively, the control module 8 may output an audible alert, such as via one or more speakers. Additionally or alternatively, the control module 8 may output a tactile alert, such as via turning on one or more vibrating devices, such as located in one or more seats, in a steering wheel, or in another suitable location.

Additionally or alternatively, the control module 8 may turn on a heating ventilation and air conditioning (HVAC) system 16 of the vehicle 5 when the amount of a chemical is greater than the predetermined amount. The control module 8 may, for example, turn on a blower of the HVAC system 16 and control one or more actuators of the HVAC system 16 to recirculate air from within the passenger cabin to outside of the passenger cabin.

Additionally or alternatively, the control module 8 may store an indicator in memory of the vehicle when the amount of a chemical is greater than the predetermined amount. The indicator may indicate that the amount of the chemical was greater than the predetermined amount. The control module 8 may also store a time stamp (e.g., including a date and a time of the occurrence) with the indicator.

Additionally or alternatively, the control module 8 may transmit an indicator to a remote device 20, such as of a fleet operator, when the amount of a chemical is greater than the predetermined amount. The control module 8 may transmit the indicator via one or more communication networks, such as a cellular communication network, a satellite communication network, a Wi-Fi communication network, or another suitable type of communication network.

Figure 2:
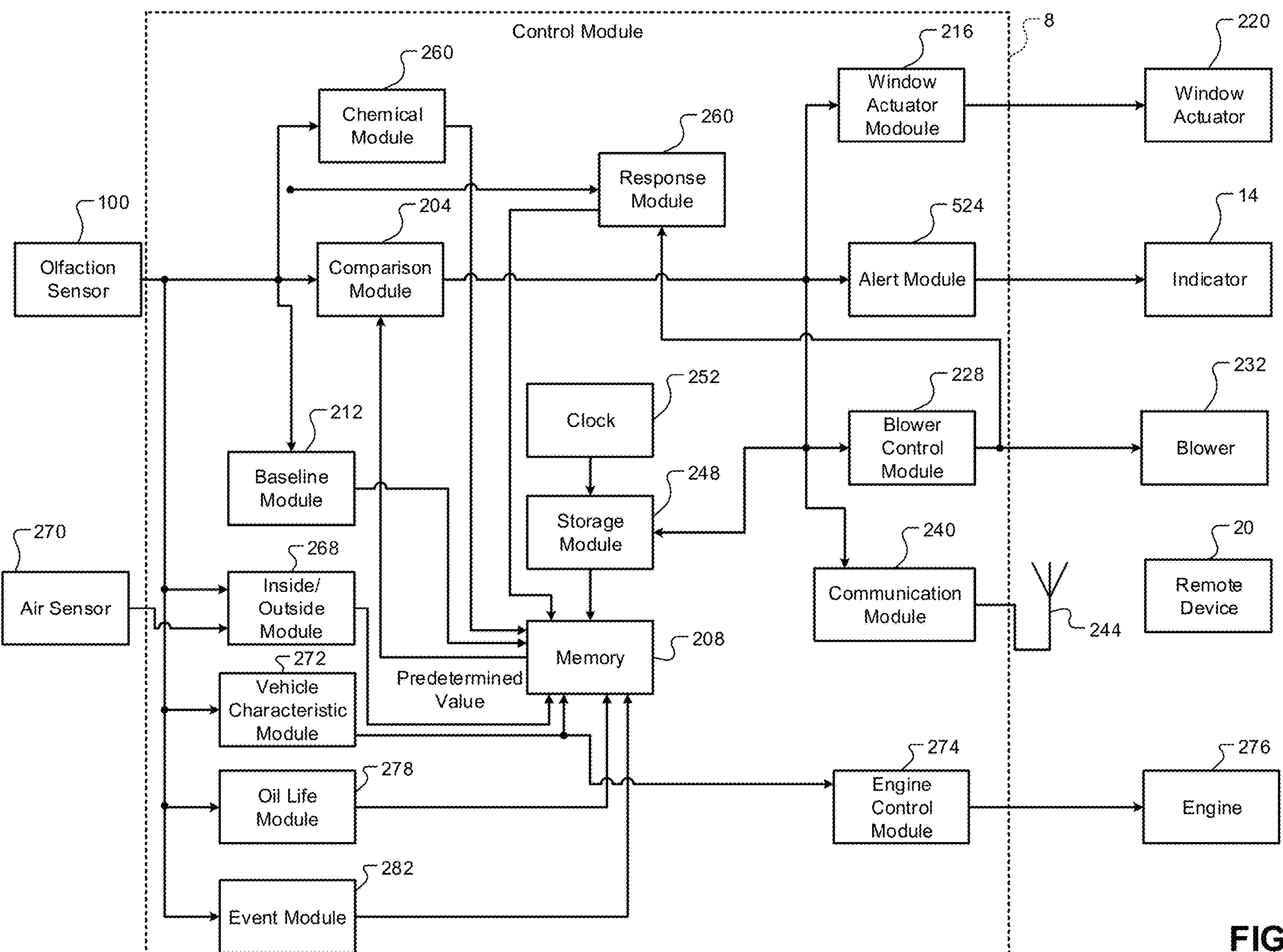
FIG. 2 is a functional block diagram of an example implementation of a control system.

FIG. 2 is a functional block diagram of an example implementation of a control system. As discussed above, one or more olfaction sensors may be included, such as at least one of a VOC sensor, a particulate matter sensor, and a carbon monoxide sensor. The olfaction sensor 100 of FIG. 2 may be a VOC sensor, a particulate matter sensor, or a carbon monoxide sensor. In various implementations, the olfaction sensor 100 may include two or more of a VOC sensor, a particulate matter sensor, and a carbon monoxide sensor.

A comparison module 204 compares a measurement from the olfaction sensor 100 with a predetermined value and generates an output signal based on the comparison. The measurement may be, for example, an amount of particulate, an amount of VOCs, or an amount of carbon monoxide. The comparison module 204 may set the output signal to the first state when the measurement is less than the predetermined value and set the output signal to a second state when the measurement is greater than or equal to the predetermined value.

The comparison module 204 may obtain the predetermined value from memory 208. The predetermined value is greater than zero and may be a fixed predetermined value. Alternatively, the predetermined value may be variable. For example, a baseline module 212 may determine a baseline value and set the predetermined value to the baseline value. The baseline module 212 may set the baseline value, for example, based or equal to an average of the measurements from the olfaction sensor 100 taken over a predetermined period, such as a week or a month. An average may be determined by summing the measurements and dividing by the number of measurements summed.

One or more remedial actions may be taken when the output signal of the comparison module 204 is in the second state. For example, a window actuator module 216 controls actuation (opening and closing) of one or more window actuators, such as window actuator 220, of the vehicle. The window actuator 220 opens (e.g., lowers) and closes (e.g., raises) a window of the vehicle. The window actuator module 216 may control one or more window actuators to open one, more than one, or all of the windows of the vehicle when the output signal of the comparison module 204 is in the second state. Opening the window(s) may include, for example, opening the window(s) to a partially open position further than the window(s) is/are presently open or opening the window(s) to a fully open position.

Additionally or alternatively, an alert module 224 may generate an alert (e.g., visually the visual indicator 14, audibly via one or more speakers, and/or haptically via one or more vibrating devices) when the output signal of the comparison module 204 is in the second state. Additionally or alternatively, a blower control module 228 may turn on a blower 232 of the HVAC system when the output signal of the comparison module 204 is in the second state.

Additionally or alternatively, a communication module 240 may wirelessly transmit an indicator to the remote device 20 via one or more antennas 244 when the output signal of the comparison module 204 is in the second state. Additionally or alternatively, a storage module 248 may store an indicator in the memory 508 when the output signal of the comparison module 204 is in the second state. The indicator may indicate that the amount of the chemical was greater than the predetermined value. The storage module 248 may also store a time stamp (e.g., including a date and a time of the occurrence) with the indicator. A clock 252 may track the date and time.

As discussed above, the vehicle 5 can include a particulate matter sensor configured to measure an amount (e.g., concentration) of one or more different chemicals within a passenger cabin of the vehicle. A chemical module 260 may determine the type of chemical, for example, based on a size of the particulate matter measured by the particulate matter sensor. For example, the chemical module 260 may determine the type of the chemical using a lookup table that relates sizes of particulate to types of chemicals. The lookup table (or database) may include sizes of various types of particulates.

The particulate matter sensor may periodically (e.g., every predetermined period) sample the air within the passenger cabin and measure the amount of particulate of different sizes in the sample. When a known gas (or chemical), such as carbon monoxide, cigarette smoke, etc. is detected by the chemical module 260, one or more remedial actions may be taken, such as described above. Examples of the remedial actions include opening one or more windows, outputting one or more indicators, turning on the blower 232 or operating the blower 232 at a faster speed, and transmitting an indicator to the remote device 20.

Further, the particulate sensor may be connected to a communication bus of the vehicle. When a known gas (or chemical) is detected, the chemical module 260 may store the occurrence of the gas (or chemical) in the memory 208. The occurrence may be transmitted wirelessly, such as via a communication module 240 of the vehicle 5. If the vehicle 5 is a fleet vehicle, the occurrence may be transmitted to a remote device (e.g., 20) of an operator or operator of the fleet.

FIGS. 3 and 4 include example illustrations of how different airborne items (e.g., gases, chemicals, etc.) vary by size for various types of particulates.

In various implementations, the chemical module 260 may determine the type of chemical within the passenger cabin, for example, using a profile of the sizes and amounts (of each size) of particulate using the lookup table. For example, a first particulate profile (including a first amount of particulate of a first size, a second amount of particulate of a second size, etc.) may be determined by the control module 8 to be indicative of cigarette smoke using the lookup table. A second particulate profile (including a third amount of particulate of a third size, a fourth amount of particulate of a fourth size, etc.) may be determined by the control module 8 to be indicative of carbon monoxide using the lookup table. FIG. 5 includes example graphs illustrating cigarette smoking and aerosol particulate profiles over time. As shown, cigarette smoke can be distinguished from other airborne items.

Additionally or alternatively, the control module 8 may determine the type of chemical within the passenger cabin, for example, using a rate of change of one or more amounts of one or more different sizes of particulate using the lookup table. For example, a first rate of change of a first size of particulate may be determined by the control module 8 to be indicative of cigarette smoke using the lookup table. A second rate of change of a second size of particulate may be determined by the control module 8 to be indicative of carbon monoxide using the lookup table. FIG. 5 also illustrates example rates of change for cigarette smoking and aerosol. As shown, cigarette smoke can be distinguished from other airborne items.

The response measured by the particulate sensor to the one or more remedial actions (e.g., opening of the window (s) 12), turning on of the HVAC system 16, etc.) may be used by the control module 8 to determine the type of chemical present within the passenger cabin. For example, cigarette smoke may take a longer period to decrease within the passenger cabin than another type of chemical. A response module 264 may therefore determine that the chemical is cigarette smoke when the particulate measured by the particulate sensor decreases slowly (e.g., at approximately a first predetermined rate) after the one or more remedial actions (e.g., opening of the window(s) 12), turning on of the HVAC system 16 such as the blower 232, etc.) have been taken. The response module 264 may store the determination in the memory 208 and/or take one or more of the remedial actions discussed above in response to the determination.

An inside/outside module 268 may determine whether a chemical within the passenger cabin originated from (a) outside of the passenger cabin or (b) within the passenger cabin. For example, the inside/outside module 268 may receive measurements from an air sensor 270 configured to measure an amount of one or more components of fresh air outside of the vehicle and the olfaction sensor 100. The air sensor 270 may measure the amount, for example, as fresh air is drawn from outside of the vehicle into the passenger cabin (e.g., via the HVAC system 16). The air sensor 270 may measure, for example, one or more amounts of one or more sizes of particulate in the fresh air.

The inside/outside module 268 may determine and indicate that the chemical originated from outside of the passenger cabin when the measurements from the air sensor 270 are indicative of the same chemical detected within the passenger cabin using the olfaction sensor 100. For example, the inside/outside module 268 may determine that the chemical originated from outside of the passenger cabin when the measurements (e.g., profile) of the air sensor 270 are approximately equal to or correspond to the measurements of the olfaction sensor 270 (e.g., particulate and/or VOCs) measuring air within the passenger cabin. If the measurements from the air sensor 270 are not approximately equal to or do not correspond to the measurements of the olfaction sensor 100 measuring air within the passenger cabin, the inside/outside module 268 may determine and indicate that the chemical originated from within the passenger cabin. This may allow the inside/outside module 268 to distinguish between chemical generating events (e.g., cigarette smoking) that occurred outside of the vehicle from chemical generating events that occurred within the passenger cabin. The inside/outside module 268 may store an indicator in the memory 208 indicative of whether the chemical originated from inside of the passenger cabin or outside of the passenger cabin. One or more other remedial actions may be taken based on whether the chemical originated from within the passenger cabin or outside of the passenger cabin. Examples of the remedial actions include opening one or more windows, outputting one or more indicators, turning on the blower 232 or operating the blower 232 at a faster speed, and transmitting an indicator to the remote device 20.

A vehicle characteristic module 272 may diagnose one or more characteristics of the vehicle 5 based on measurements from one or more of the olfaction sensors, such as the particulate matter sensor and the VOC sensor. For example, the vehicle characteristic module 272 may include a stored lookup table of combinations of particulate measurements and VOC measurements to vehicle characteristics. As an example, using the lookup table, the vehicle characteristic module 272 may determine that a catalytic converter of the vehicle 5 is not properly converting engine exhaust when the particulate matter and VOC sensors provide a first combination of particulate and VOC measurements indicative of the catalytic converter not properly converting engine exhaust. Using the lookup table, the vehicle characteristic module 272 may determine that the vehicle 5 is leaking engine coolant when the particulate matter and VOC sensors provide a second combination of particulate and VOC measurements indicative of an engine coolant leak. Using the lookup table, the vehicle characteristic module 272 may determine that the vehicle 5 is leaking engine oil when the particulate matter and VOC sensors provide a third combination of particulate and VOC measurements indicative of an engine oil leak.

Using the lookup table, the vehicle characteristic module 272 may determine that the vehicle 5 has a belt or hose rubbing against a moving (e.g., rotating) component (e.g., a pulley) when the particulate matter and VOC sensors provide a fourth combination of particulate and VOC measurements indicative of a belt or hose rubbing against a moving component. Using the lookup table, the vehicle characteristic module 272 may determine that the vehicle 5 has an overheating clutch when the particulate matter and VOC sensors provide a fifth combination of particulate and VOC measurements indicative of an overheating clutch. Using the lookup table, the vehicle characteristic module 272 may determine that the vehicle 5 has an issue (e.g., faulty or failing) with one or more brakes (e.g., mechanical, emergency, etc.) when the particulate matter and VOC sensors provide a sixth combination of particulate and VOC measurements indicative of an issue with brakes.

An example lookup table and some possible particulate and VOC combinations is provided below.

| Measurement combination | Diagnosis |
| --- | --- |
| PM1 and VOC1 | Catalytic converter issue |
| PM2 and VOC2 | Engine coolant leak |
| PM3 and VOC3 | Engine oil leak |
| PM4 and VOC4 | belt or hose rubbing |
| PM5 and VOC5 | Overheating clutch |
| PM6 and VOC6 | Brake issue |
| . . . | . . . |

FIG. 6 includes an example radius graph (at 0-63 sensor nodes in this example) of VOCs and particulate matter measured at a seat (a rear seat in this example) within the passenger cabin at corresponding sensor nodes. Trace 604 tracks the amount of VOCs and particulate at the seat before a vehicle condition occurs (baseline). Trace 608 tracks the amount of VOCs and particulate at the seat over time and compares the measurement to baseline trace 604. As illustrated, the measurements between the baseline (before the vehicle condition occurs) 604 and the measurements after the vehicle condition has occurred allow the vehicle characteristic module 272 to identify the presence of the vehicle condition. In various implementations, the chemical module 260 may diagnose a type of chemical or condition (e.g., pets, food, type of food, etc.) within the passenger cabin similarly. In the example of food, measurements between the baseline (before the condition occurs) and the measurements after the vehicle condition has occurred may allow the chemical module 260 to distinguish between types of events within the passenger cabin and even between types of food present in the passenger cabin.

FIG. 7 includes an example table including conditions that may be associated with different types of events within the passenger cabin. While example events are provided, the present application is also applicable to other events.

Using the lookup table, the vehicle characteristic module 272 may determine that the vehicle 5 is overloaded (i.e., has a load over a predetermined load rating of the vehicle 5) when the particulate matter and VOC sensors provide a seventh combination of particulate and VOC measurements indicative of the vehicle 5 being overloaded. In various implementations, an engine control module 274 may adjust one or more operating parameters of an internal combustion engine 276 of the vehicle 5 when the vehicle 5 is overloaded.

In various implementations, the vehicle characteristic module 272 may use a response in exhaust VOCs to differentiate between possible vehicle characteristics. Using the lookup table, the vehicle characteristic module 272 may determine that a battery of the vehicle (e.g., an electric vehicle or a hybrid vehicle) has an issue (e.g., failure or fault) when the particulate matter and VOC sensors provide an eighth combination of particulate and VOC measurements indicative of an issue in the battery.

The vehicle characteristic module 272 may store an indicator in the memory 208 indicative of the vehicle characteristic. One or more other remedial actions may be taken based on the vehicle characteristic. Examples of the remedial actions include opening one or more windows, outputting one or more indicators, turning on the blower 232 or operating the blower 232 at a faster speed, and transmitting an indicator of the vehicle condition to the remote device 20.

FIG. 8 includes an example table including conditions that may be associated with different types of vehicle characteristics. While example vehicle characteristics are provided, the present application is also applicable to other vehicle characteristics.

An oil life module 278 may determine an oil life of engine oil of the vehicle 5 based on measurements from one or more of the olfaction sensors, such as the particulate matter sensor and the VOC sensor. For example, the oil life module 278 may include a stored lookup table of combinations of particulate measurements and VOC measurements to engine oil life values (e.g., percentages of new, where 100% corresponds to new engine oil).

As an example, using the lookup table, the oil life module 278 may determine that the engine oil has an 85 percent life when the particulate matter and VOC sensors provide a first combination of particulate and VOC measurements indicative of the oil having an 85 percent remaining life. Using the lookup table, the oil life module 278 may determine that the engine oil has a 75 percent life when the particulate matter and VOC sensors provide a second combination of particulate and VOC measurements indicative of the oil having a 75 percent remaining life.

Using the lookup table, the oil life module 278 may determine that the engine oil has a 50 percent life when the particulate matter and VOC sensors provide a third combination of particulate and VOC measurements indicative of the oil having a 50 percent remaining life. Using the lookup table, the oil life module 278 may determine that the engine oil has a 30 percent life when the particulate matter and VOC sensors provide a fourth combination of particulate and VOC measurements indicative of the oil having a 30 percent remaining life. Using the lookup table, the oil life module 278 may determine that the engine oil has a 10 percent life when the particulate matter and VOC sensors provide a fifth combination of particulate and VOC measurements indicative of the oil having a 10 percent remaining life. While the examples of 85 percent, 75 percent, 50 percent, 30 percent, and 10 percent have been provided, other percentages and combinations of particulate and VOC measurements may be used.

The oil life module 278 may also determine an oil life of engine oil of the vehicle 5 based on measurements from one or more of the olfaction sensors, such as the particulate matter sensor and the VOC sensor. For example, the vehicle 5 may include a stored lookup table of combinations of particulate measurements and VOC measurements to engine oil life values (e.g., percentages of new, where 100% corresponds to new engine oil).

An example lookup table and some possible particulate and VOC combinations is provided below.

| Measurement combination | Remaining oil life |
| --- | --- |
| PM1 and VOC1 | 85 percent |
| PM2 and VOC2 | 75 percent |
| PM3 and VOC3 | 50 percent |
| PM4 and VOC4 | 35 percent |
| PM5 and VOC5 | 25 percent |
| PM6 and VOC6 | 10 percent |
| . . . | . . . |

FIG. 9 includes an example radius graph of magnitudes of one or more different measurements/nodes (e.g., VOCs and/or particulate matter) measured at a seat within the passenger cabin. Each node may be based on an amount of one or more different VOCs and/or one or more sizes of particulate. For example, a node may correspond to an amount of a VOC and/or a size of particulate.

Trace 904 corresponds to new oil, while trace 908 tracks used oil. As illustrated, the measurements between the new and used oil allow the vehicle oil life module 278 to identify the presence of age and remaining life of the oil. For example, differences between peaks at nodes 9, 14, 24, and 57 may be used to determine the age and remaining life of the oil.

FIG. 10 includes an example table including measurements associated with different oil characteristics. While example oil characteristics and life are provided, the present application is also applicable to other characteristics and remaining life.

The oil life module 278 may store an indicator of the oil life or remaining oil life in the memory 208. One or more other remedial actions may be taken based on the oil life or the remaining oil life. Examples of the remedial actions include outputting one or more indicators, and transmitting an indicator of the vehicle condition to the remote device 20. For example, the alert module 524 may output one or more indicators when the remaining oil life is less than a predetermined value (e.g., 5 percent or another suitable value).

FIGS. 11 and 12 include example graphs for 85% remaining oil life and 10% remaining oil life, respectively.

An event module 282 may determine whether one or more different types of events occurred previously within the passenger cabin based on measurements from one or more of the olfaction sensors, such as the particulate matter sensor and the VOC sensor. For example, the event module 282 may include a stored lookup table of combinations of particulate measurements and VOC measurements to previous events within the passenger cabin of the vehicle.

For example, using the lookup table, the event module 282 may determine that a pet has been allowed in the passenger cabin of the vehicle when the particulate matter and VOC sensors provide a first combination of particulate and VOC measurements indicative of one or more pets being present in the passenger cabin. Using the lookup table, the event module 282 may determine that cigarettes have been smoked in the passenger cabin when the particulate matter and VOC sensors provide a second combination of particulate and VOC measurements indicative of previous cigarette smoking. Using the lookup table, the event module 282 may determine that marijuana has been smoked in the passenger cabin when the particulate matter and VOC sensors provide a second combination of particulate and VOC measurements indicative of previous marijuana smoking.

An example lookup table and some possible particulate and VOC combinations is provided below. As discussed above, FIG. 7 includes an example illustration of a table including different combinations of particulate and VOC that can be used to diagnose different types of events occurred within the passenger cabin.

| Measurement combination | Diagnosis |
| --- | --- |
| PM1 and VOC1 | Pet(s) in passenger cabin |
| PM2 and VOC2 | Cigarette smoking in passenger cabin |
| PM3 and VOC3 | Marijuana smoking in passenger cabin |
| . . . | . . . |

In various implementations, the control module 8 may be implemented separately from the vehicle 5. The control module 8 may remote from the vehicle 5 and configured to electrically connect to a port of the vehicle 5, such as an on board diagnostic (OBD) port or another suitable type of port. In various implementations, the remote device 20 may electrically connect with the control module 8 of the vehicle 5 by wire via the port and receive one or more diagnoses of the control module 8 via the wired connection.

FIG. 13 is a flowchart depicting an example method of diagnosing conditions and events within the passenger cabin of the vehicle. Control begins with 1304 where the control module 8 receives baseline measurements (e.g., VOCs and/or particulate) from within the passenger cabin. The baseline measurements may be stored in the memory 208 and obtained, for example, when the vehicle 5 was new or one or more previous trips of the vehicle.

At 1308, the control module 8 receives present measurements from the olfaction sensor 100, such as the amounts of one or more VOCs and/or the amount of one or more sizes of particulate matter. At 1312, the control module 8 may determine the remaining life of the engine oil based on the present measurements and the baselines. In various implementations 1312 may be omitted as it may not be necessary for 1316.

At 1316, the control module 8 determines whether one or more conditions or events or one or more vehicle characteristics are present, as discussed above. If 1316 is true, the control module 1320 may store an indicator of the conditions or events or one or more vehicle characteristics in the memory 208 at 1320. In various implementations, the control module 1320 may take one or more remedial actions, such as discussed above. While the example of ending is provided, control may return to 1304.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

In this application, including the definitions below, the terms "module" and "system" may refer to, be part of, or include circuits or circuitry that may include processor hardware (shared, dedicated, or group) that executes code and memory hardware (shared, dedicated, or group) that stores code executed by the processor hardware. The code is configured to provide the features of the modules and systems described herein. In addition, in this application the terms "module" and "system" may be replaced with the term "circuit." The term "memory hardware" may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as JavaScript Object Notation (JSON), hypertext markup language (HTML) or extensible markup language (XML); (ii) assembly code; (iii) object code generated from source code by a compiler; (iv) source code for execution by an interpreter; (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A vehicle system, comprising:

at least one of:

a particulate matter sensor configured to measure an amount of particulate within a passenger cabin of a vehicle; and a volatile organic compounds (VOC) sensor configured to measure an amount of VOCs within the passenger cabin of the vehicle; and a control module configured to, based on at least one of the amount of particulate and the amount of VOCs within the passenger cabin of the vehicle, diagnose a characteristic of the vehicle;

wherein the characteristic includes at least one of:

a fault of a catalytic converter;

engine coolant leak;

an engine oil leak;

rubbing of a belt or a hose;

overheating of a clutch;

a fault associated with one or more brakes; and overloading of the vehicle.

2. The vehicle system of claim 1 wherein the control module is configured to store the diagnosis in memory of the vehicle.

3. The vehicle system of claim 1 wherein the control module is configured to transmit the diagnosis to a remote device.

4. The vehicle system of claim 3 wherein the control module is configured to transmit the diagnosis to the remote device via a wireless transceiver of the vehicle.

5. The vehicle system of claim 3 wherein the control module is configured to transmit the diagnosis to the remote device via a wired connection between the remote device and a port of the vehicle.

6. The vehicle system of claim 1 wherein the control module is further configured to, based on the at least one of the amount of particulate and the amount of VOCs within the passenger cabin of the vehicle, diagnose at least one of:

presence of a chemical in the passenger cabin of the vehicle;

occurrence of an event within the passenger cabin of the vehicle; and a remaining life of engine oil of the vehicle.

7. The vehicle system of claim 1 wherein the control module is configured to make the diagnosis further based on at least one of a baseline amount of particulate from before the diagnosis and a baseline amount of VOCs within the passenger cabin of the vehicle from before the diagnosis.

8. The vehicle system of claim 6 wherein the control module is configured to, based on the at least one of the amount of particulate and the amount of VOCs within the passenger cabin of the vehicle, diagnose the occurrence of an event within a passenger cabin of the vehicle.

9. The vehicle system of claim 8 wherein the event is one of smoking, presence of an animal, and presence of food.

10. The vehicle system of claim 6 wherein the control module is configured to, based on the at least one of the amount of particulate and the amount of VOCs within the passenger cabin of the vehicle, diagnose the presence of a chemical in the passenger cabin of the vehicle.

11. The vehicle system of claim 6 wherein the control module is configured to, based on the at least one of the amount of particulate and the amount of VOCs within the passenger cabin of the vehicle, diagnose the remaining life of engine oil of the vehicle.

12. A method comprising:

at least one of:

measuring an amount of particulate within a passenger cabin of a vehicle; and measuring an amount of a volatile organic compounds (VOCs) within the passenger cabin of the vehicle; and based on at least one of the amount of particulate and the amount of VOCs within the passenger cabin of the vehicle, diagnosing at least one of:

a characteristic of the vehicle;

presence of a chemical in the passenger cabin of the vehicle;

occurrence of an event within the passenger cabin of the vehicle; and a remaining life of engine oil of the vehicle, wherein the diagnosing includes, based on the at least one of the amount of particulate and the amount of VOCs within the passenger cabin of the vehicle, diagnosing a characteristic of the vehicle, and wherein the characteristic includes at least one of:

a fault of a catalytic converter;

engine coolant leak;

an engine oil leak;

rubbing of a belt or a hose;

overheating of a clutch;

a fault associated with one or more brakes; and overloading of the vehicle.

13. A vehicle system, comprising:

at least one of:

a particulate matter sensor configured to measure an amount of particulate within a passenger cabin of a vehicle; and a volatile organic compounds (VOC) sensor configured to measure an amount of VOCs within the passenger cabin of the vehicle; and a control module configured to, based on at least one of the amount of particulate and the amount of VOCs within the passenger cabin of the vehicle, diagnose a characteristic of the vehicle, wherein the characteristic includes a fault in a battery of the vehicle.

* * * * *